(12) United States Patent
Cheung

(10) Patent No.: US 9,248,203 B2
(45) Date of Patent: Feb. 2, 2016

(54) FLUORESCENT IMAGING WITH SUBSTITUTED CYANINE DYES

(75) Inventor: Lael Cheung, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 548 days.

(21) Appl. No.: 13/602,054

(22) Filed: Aug. 31, 2012

(65) Prior Publication Data

US 2013/0039860 A1 Feb. 14, 2013

Related U.S. Application Data

(63) Continuation of application No. PCT/US2011/057178, filed on Oct. 20, 2011.

(60) Provisional application No. 61/405,158, filed on Oct. 20, 2010, provisional application No. 61/405,161, filed on Oct. 20, 2010.

(51) Int. Cl.
| | |
|---|---|
| *A61K 49/00* | (2006.01) |
| *C09B 23/01* | (2006.01) |
| *C09B 23/08* | (2006.01) |
| *C09B 69/00* | (2006.01) |
| *G01N 33/574* | (2006.01) |
| *G01N 33/58* | (2006.01) |
| *C07D 471/04* | (2006.01) |
| *C07F 9/6561* | (2006.01) |
| *C07K 19/00* | (2006.01) |
| *C08B 37/08* | (2006.01) |

(52) U.S. Cl.
CPC ......... *A61K 49/0058* (2013.01); *A61K 49/0032* (2013.01); *A61K 49/0052* (2013.01); *C07D 471/04* (2013.01); *C07F 9/6561* (2013.01); *C07K 19/00* (2013.01); *C08B 37/0072* (2013.01); *C09B 23/0008* (2013.01); *C09B 23/0016* (2013.01); *C09B 23/0025* (2013.01); *C09B 23/0066* (2013.01); *C09B 23/083* (2013.01); *C09B 23/086* (2013.01); *C09B 69/00* (2013.01); *G01N 33/574* (2013.01); *G01N 33/58* (2013.01); *G01N 33/582* (2013.01)

(58) Field of Classification Search
CPC ....... A61K 49/00; C07C 24/00; C09B 23/087
USPC .................................................. 424/9.1, 9.6
See application file for complete search history.

(56) References Cited

U.S. PATENT DOCUMENTS

| | | |
|---|---|---|
| 3,723,419 A | 3/1973 | Mee et al. |
| 3,864,644 A | 2/1975 | Lincoln et al. |
| 4,011,086 A | 3/1977 | Simson |
| 4,264,694 A | 4/1981 | Pu et al. |
| 4,871,656 A | 10/1989 | Parton et al. |
| 5,453,505 A | 9/1995 | Lee et al. |
| 5,571,388 A | 11/1996 | Patonay et al. |
| 5,639,874 A | 6/1997 | Middendorf et al. |
| 5,831,098 A | 11/1998 | Ollmann, Jr. |

(Continued)

FOREIGN PATENT DOCUMENTS

| | | |
|---|---|---|
| DE | 4445065 A1 | 6/1996 |
| EP | 0 341 958 A2 | 11/1989 |

(Continued)

OTHER PUBLICATIONS

Berezin et al., "Ratiometric Analysis of Fluorescence Lifetime for Probing Binding Sites in /albumin with Near-Infrared Fluorescent Molecular Probes," Photochemistry and Photobiology, 2007, vol. 83, pp. 1371-1378.

(Continued)

*Primary Examiner* — Michael G Hartley
*Assistant Examiner* — Jagadishwar Samala
(74) *Attorney, Agent, or Firm* — Kilpatrick Townsend & Stockton LLP

(57) ABSTRACT

Compounds and methods are disclosed that are useful for noninvasive imaging in the near-infrared spectral range. The cyanine compounds of Formula I are presented:

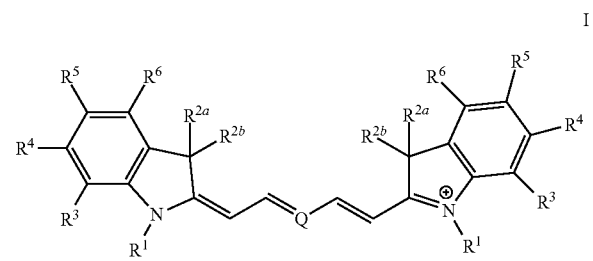

wherein
Q is a portion of a polymethine bridge:

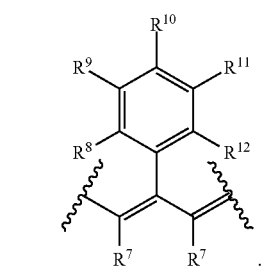

Also included are bioconjugates of the compounds of Formula I, methods of labeling biomolecules with the compounds, and methods of imaging.

25 Claims, 9 Drawing Sheets

(56) References Cited

U.S. PATENT DOCUMENTS

| | | | |
|---|---|---|---|
| 6,048,982 | A | 4/2000 | Waggoner |
| 6,083,485 | A | 7/2000 | Licha et al. |
| 6,086,737 | A | 7/2000 | Patonay et al. |
| 6,136,612 | A | 10/2000 | Della Ciana et al. |
| 6,180,085 | B1 | 1/2001 | Achilefu et al. |
| 6,217,848 | B1 | 4/2001 | Achilefu et al. |
| 6,258,340 | B1 | 7/2001 | Licha et al. |
| 6,287,662 | B1 | 9/2001 | Takagishi et al. |
| 6,395,257 | B1 | 5/2002 | Achilefu et al. |
| 6,534,041 | B1 | 3/2003 | Licha et al. |
| 6,673,334 | B1 | 1/2004 | Achilefu et al. |
| 6,706,254 | B2 | 3/2004 | Achilefu et al. |
| 6,716,994 | B1 | 4/2004 | Menchen et al. |
| 6,747,159 | B2 | 6/2004 | Caputo et al. |
| 6,761,878 | B2 | 7/2004 | Achilefu et al. |
| 6,913,743 | B2 | 7/2005 | Licha et al. |
| 6,926,885 | B2 | 8/2005 | Licha et al. |
| 6,949,635 | B1 | 9/2005 | Kumar et al. |
| 6,974,873 | B2 | 12/2005 | Leung et al. |
| 6,977,305 | B2 | 12/2005 | Leung et al. |
| 7,025,949 | B2 | 4/2006 | Licha et al. |
| 7,128,896 | B2 | 10/2006 | Achilefu et al. |
| 7,172,907 | B2 | 2/2007 | Chen et al. |
| 7,175,831 | B2 | 2/2007 | Achilefu et al. |
| 7,201,892 | B2 | 4/2007 | Achilefu et al. |
| 7,252,815 | B2 | 8/2007 | Achilefu et al. |
| 7,445,767 | B2 | 11/2008 | Licha et al. |
| 7,807,619 | B2 | 10/2010 | Bertozzi et al. |
| 7,910,335 | B2 | 3/2011 | Salic et al. |
| 8,569,506 | B2 | 10/2013 | Leung et al. |
| 2001/0055567 | A1 | 12/2001 | Licha et al. |
| 2002/0022004 | A1 | 2/2002 | Licha et al. |
| 2002/0156288 | A1 | 10/2002 | Caputo et al. |
| 2003/0026763 | A1 | 2/2003 | Licha et al. |
| 2003/0113755 | A1 | 6/2003 | Nishigaki et al. |
| 2003/0170179 | A1 | 9/2003 | Licha et al. |
| 2003/0180221 | A1 | 9/2003 | Miwa et al. |
| 2003/0185756 | A1 | 10/2003 | Achilefu et al. |
| 2004/0014981 | A1 | 1/2004 | Lugade et al. |
| 2004/0234454 | A1 | 11/2004 | Achilefu et al. |
| 2004/0241095 | A1 | 12/2004 | Achilefu et al. |
| 2004/0253182 | A1 | 12/2004 | Achilefu et al. |
| 2005/0031542 | A1 | 2/2005 | Achilefu et al. |
| 2005/0106106 | A1 | 5/2005 | Licha et al. |
| 2005/0169844 | A1 | 8/2005 | Licha et al. |
| 2005/0226815 | A1 | 10/2005 | Kawakami et al. |
| 2005/0271592 | A1 | 12/2005 | Achilefu et al. |
| 2005/0281741 | A1 | 12/2005 | Achilefu et al. |
| 2006/0009638 | A1 | 1/2006 | Lindsey et al. |
| 2006/0165598 | A1 | 7/2006 | Licha et al. |
| 2006/0165599 | A1 | 7/2006 | Licha et al. |
| 2006/0216760 | A1 | 9/2006 | Dieterich et al. |
| 2006/0223076 | A1 | 10/2006 | Diwu et al. |
| 2007/0021621 | A1 | 1/2007 | Reddington |
| 2007/0090331 | A1 | 4/2007 | Seo et al. |
| 2007/0128115 | A1 | 6/2007 | Achilefu et al. |
| 2007/0140962 | A1 | 6/2007 | Achilefu et al. |
| 2007/0178511 | A1 | 8/2007 | Leung et al. |
| 2007/0232805 | A1 | 10/2007 | Leung et al. |
| 2008/0267878 | A1 | 10/2008 | Robillard et al. |
| 2009/0035809 | A1 | 2/2009 | Leung et al. |
| 2009/0305410 | A1 | 12/2009 | Mao et al. |
| 2010/0210854 | A1 | 8/2010 | Popik et al. |
| 2010/0215748 | A1 | 8/2010 | Ladet et al. |
| 2010/0234450 | A1 | 9/2010 | Schultz et al. |
| 2010/0297250 | A1 | 11/2010 | Boons et al. |
| 2011/0118142 | A1 | 5/2011 | Clarke et al. |
| 2011/0118484 | A1 | 5/2011 | Bernardin et al. |
| 2012/0028290 | A1* | 2/2012 | Salic ................................ 435/29 |
| 2012/0288871 | A1 | 11/2012 | Leung et al. |

FOREIGN PATENT DOCUMENTS

| | | |
|---|---|---|
| EP | 1221465 A1 | 7/2002 |
| EP | 0796111 B1 | 4/2003 |
| EP | 1181940 B1 | 12/2004 |
| EP | 1815870 A1 | 8/2007 |
| FR | 2921838 A1 | 4/2009 |
| JP | 10 071766 A | 3/1998 |
| JP | 11-73679 A | 3/1999 |
| JP | 2002 109794 A | 4/2002 |
| JP | 2005 120026 A | 5/2005 |
| WO | 97/13490 A2 | 4/1997 |
| WO | 97/13810 A1 | 4/1997 |
| WO | 97/47538 A2 | 10/1998 |
| WO | 98/53940 A1 | 12/1998 |
| WO | 01/49790 A2 | 7/2001 |
| WO | 02/24815 A1 | 3/2002 |
| WO | WO-02/24815 * | 3/2002 |
| WO | 02/26891 A1 | 4/2002 |
| WO | 03/074091 A2 | 9/2003 |
| WO | 2004/065491 A1 | 8/2004 |
| WO | 2007/028118 A2 | 3/2007 |
| WO | 2007/028163 A2 | 3/2007 |
| WO | 2007/088129 A2 | 8/2007 |
| WO | WO 2010/039548 | 4/2010 |
| WO | 2010/121163 A2 | 10/2010 |
| WO | WO 2011/028507 | 3/2011 |

OTHER PUBLICATIONS

Berezin et al., Biophysical Journal, 2007, 93, 2892-2899.

Flanagan et al., "Near-Infrared Heavy-Atom-Modified fluorescent Dyes for Base-Calling in DNA-Sequencing Applications using Temporal Discrimination," Analytical Chemistry, 1998, vol. 70, No. 13, pp. 2676-2684.

Lee et al., JOC, 2008, 73(2), 723-725.

Lee et al., JOC, 2006, 71(20), 7862-7865.

International Search Report, Mailing date Feb. 2, 2012, PCT application No. PCT/US2011/057178, 3 pages.

Chang et al., "Copper-free click chemistry in living animals," PNAS, 2010, vol. 107, pp. 1821-1826.

Kolb et al., "Click Chemistry: Diverse Chemical Function from a Few Good Reactions," Angew. Chemie., 2001, vol. 40, pp. 2004-2021.

Moses et al., "The growing application of click chemistry," Chem. Soc. Rev., 2007, vol. 36, pp. 1249-1262.

* cited by examiner

Absorption and Emission of Compound 11 in PBS

Absorption and Emission of Compound 16 in PBS 0.2 µg/ml dilution. Spectral results are normalized to IRDye® 800CW.

0.2 ng/ml dilution. Spectral results are normalized to IRDye® 800CW.

FIG. 8A
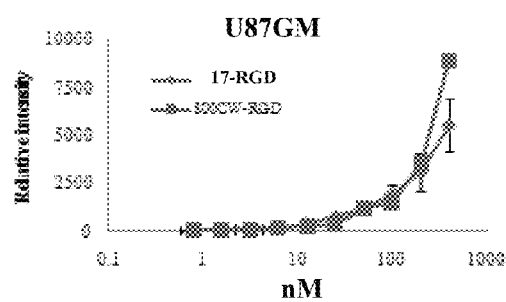
FIG. 8B
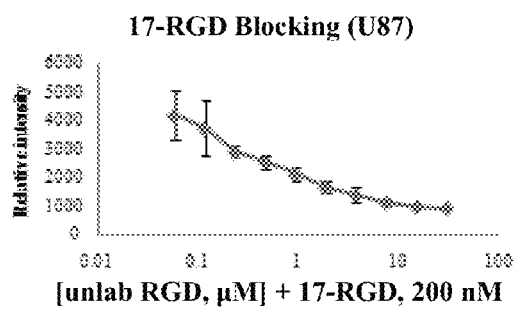
FIG. 8

FIG. 9A
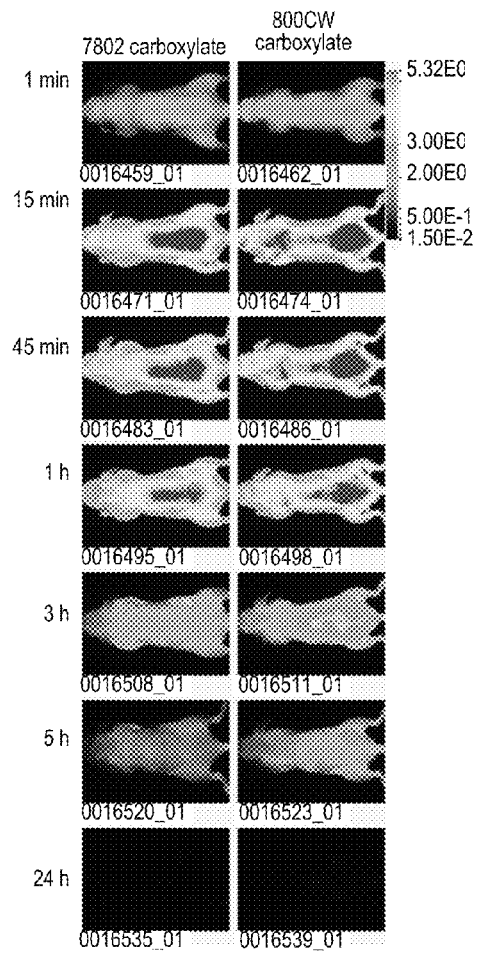
FIG. 9B
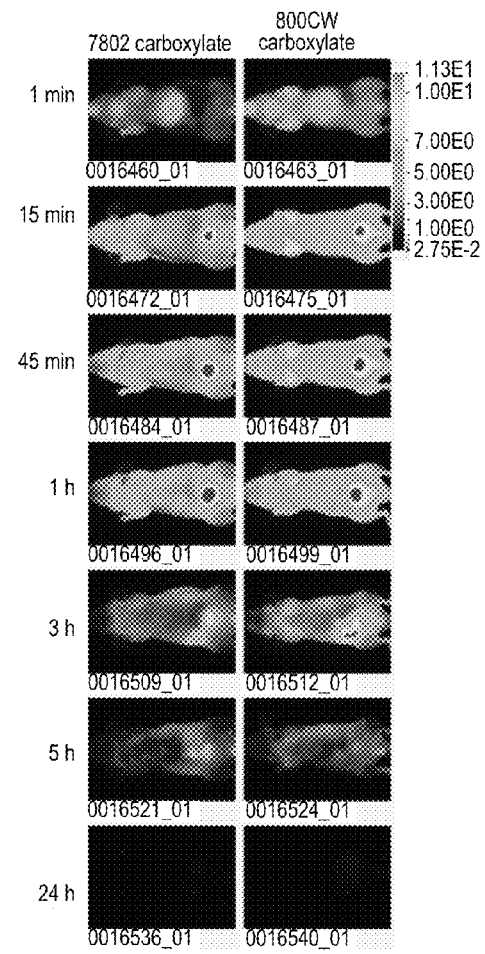
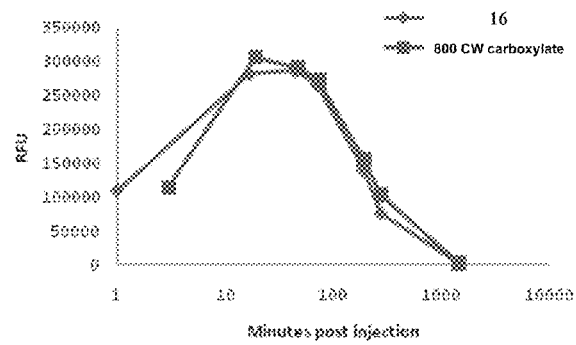
FIG 9C

FLUORESCENT IMAGING WITH SUBSTITUTED CYANINE DYES

CROSS-REFERENCES TO RELATED APPLICATIONS

This application is a continuation of PCT/US2011/057178, filed Oct. 20, 2011, which application claims priority to U.S. Provisional Patent Application Nos. 61/405,158 and 61/405,161 (both filed Oct. 20, 2010), each of which is hereby incorporated by reference for all purposes.

BACKGROUND OF THE INVENTION

Cyanine dyes have been widely used for labeling ligands or biomolecules for a variety of applications such as DNA sequencing. (See, for example, U.S. Pat. No. 5,571,388 for exemplary methods of identifying strands of DNA by means of cyanine dyes). More recently, they have been used for optical imaging of dye-labeled biomolecules, either in vivo or in vitro. (See, for example, U.S. Pat. No. 7,597,878.) Scientists favor using cyanine dyes in biological applications because, among other reasons, many of these dyes fluoresce in the near-infrared (NIR) region of the spectrum (600-1000 nm). This makes cyanine dyes less susceptible to interference from autofluorescence of biomolecules.

Other advantages of cyanine dyes include, for example: 1) cyanine dyes strongly absorb and fluoresce light; 2) many cyanine dyes do not rapidly bleach under a fluorescence microscope; 3) cyanine dye derivatives can be made that are effective coupling reagents; 4) many structures and synthetic procedures are available, and the class of dyes is versatile; and 5) cyanine dyes are relatively small (a typical molecular weight is about 1,000 daltons), so they do not cause appreciable steric interference in a way that might reduce the ability of a labeled biomolecule to reach its binding site or carry out its function.

Yet another advantage of cyanine dyes is that structural modifications can be made by those skilled in the art that will shift the absorption and emission curves. This is important in matching dyes to specific detection systems and application environments. Some such modifications may adversely affect the performance of the dyes in other ways. For example, the dye fluorescence may be reduced, or the dye may stack in solution, or bind to other elements in the application system in a non-specific manner. Therefore, additional approaches for modifying the wavelength properties are of significant interest.

Despite their advantages, many of the known cyanine dyes have a number of disadvantages. Some known cyanine dyes are not stable in the presence of certain reagents that are commonly found in bioassays. Such reagents include ammonium hydroxide, dithiothreitol (DTT), primary and secondary amines, and ammonium persulfate (APS). Further, some known cyanine dyes lack the thermal stability and photostability that is necessary for biological applications such as DNA sequencing, Western blotting, in-cell Western immunofluorescence assays, in vitro or in vivo optical imaging, microscopy, and genotyping.

For these reasons, stable cyanine dyes are needed for use in labeling biomolecules as well as in vivo imaging for the diagnosis and prognosis of diseases such as cancer. Such compositions and methods would aid in the analysis of responses to various therapies. The present invention satisfies these and other needs.

BRIEF SUMMARY OF THE INVENTION

The present invention provides compounds, bioconjugates, methods of labeling, and methods of measuring or detecting target molecules non-invasively, thus solving the problems of the above-described art.

As such, in one embodiment, the present invention provides a compound of Formula I:

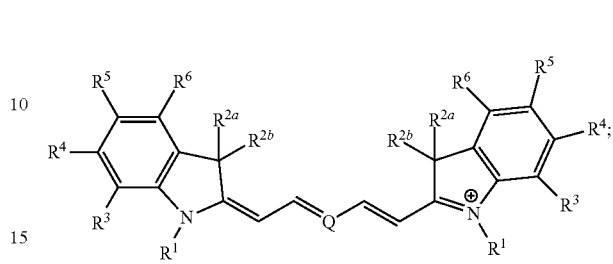

wherein Q is a portion of a polymethine bridge:

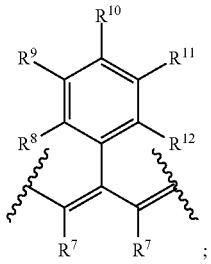

wherein Q is the central portion of a seven-polymethine-carbon polymethine bridge;

each $R^1$ is a member selected from the group consisting of -L-Y—Z and an alkyl that is additionally substituted with from 0 to 1 $R^{14}$ and from 0 to 1 -L-Y—Z; wherein the alkyl is optionally interrupted by at least one heteroatom;

each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 -L-Y—Z; or, alternatively, a $R^{2a}$ and $R^{2b}$ pair, together with the ring carbon to which the $R^{2a}$ and $R^{2b}$ are bonded, join to form either a spirocycloalkyl ring, wherein the spirocycloalkyl ring is additionally substituted with from 0 to 6 $R^{14}$ and from 0 to 1 -L-Y—Z, or an exocyclic alkene, wherein the exocyclic alkene is additionally substituted with from 0 to 2 $R^{14}$ and from 0 to 1 -L-Y—Z;

each $R^3$, $R^4$, $R^5$, and $R^6$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 -L-Y—Z; or, alternatively, a pair of said members that is selected from the group consisting of $R^3$ and $R^4$, $R^4$ and $R^5$, and $R^5$ and $R^6$, together with the pair of atoms to which the pair of said members is bonded, joins to form an aryl ring, wherein the aryl ring is additionally substituted with from 0 to 2 $R^{14}$ and from 0 to 1 -L-Y—Z;

each $R^7$ is a member independently selected from the group consisting of hydrogen and alkyl; wherein the alkyl is additionally substituted with from 0 to 3 $R^{14}$ and from 0 to 1 -L-Y—Z; or, alternatively, both $R^7$, together with the intervening segment of the polyene to which both $R^7$ are bonded, join to form a ring, wherein said ring is selected from the group consisting of a cycloalkyl and a heterocyclyl ring; wherein the ring is additionally substituted with from 0 to 3 $R^{14}$ and from 0 to 1 -L-Y—Z; and wherein the ring is optionally substituted with an exocyclic alkene, wherein the alkene is additionally substituted with from 0 to 2 $R^{14}$ and from 0 to 1 -L-Y—Z;

$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein at least one member selected from the group consisting of $R^8$, $R^9$, and $R^{10}$ is halo;

each $R^{13}$ is a member independently selected from the group of hydroxyl, amino, carboxyl, and alkoxycarbonyl;

each $R^{14}$ is a member independently selected from the group consisting of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the alkyl or alkenyl is additionally substituted with from 0 to 1 $R^{13}$ and from 0 to 1 -L-Y—Z;

each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom;

each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;

each Z is independently selected from the group consisting of -L-R$^{13}$ and -L-R$^{16}$, wherein in an alternative embodiment, —Y—Z is a member selected from the group of —N(Z)$_2$, —N(Z)C(O)Z, and —C(O)N(Z)$_2$, wherein the two Z groups may optionally be linked to form a cycloalkynyl group;

each $R^{15}$ is a member independently selected from the group consisting of alkyl and alkoxycarbonylalkyl; wherein the alkyl is optionally interrupted by at least one heteroatom;

each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, cycloalkynyl, spirocycloalkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester;

and wherein said compound has a balanced charge.

Preferably, said compound has at least one -L-Y—Z group; more preferably, said compound has exactly one -L-Y—Z group.

In another embodiment, the present invention provides a bioconjugate of the Formula II:

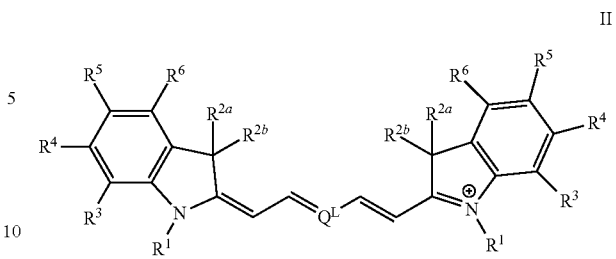

II wherein $Q^L$ is a portion of a polymethine bridge:

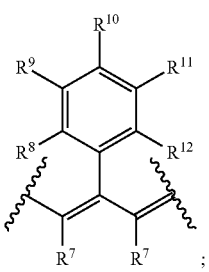

wherein $Q^L$ is the central portion of a seven-polymethine-carbon polymethine bridge;

wherein $R^1$, $R^{2a}$, $R^{2b}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, L, and Y are as previously defined for the compound of Formula I;

each Z is independently selected from the group consisting of -L-R$^{13}$ and -L-R$^L$;

each $R^L$ comprises a linking group and a biomolecule connected thereby, wherein the compound comprises at least one $R^L$, and wherein the compound has a balanced charge. Preferably, the compound comprises exactly one $R^L$.

In yet another embodiment, the present invention provides a method or process for labeling a ligand or biomolecule with a compound of Formula I, the method comprising contacting a ligand or biomolecule with a compound having Formula I to generate the corresponding bioconjugate compound of Formula II.

In still yet another embodiment, the compounds of Formula I or II can be used as in vitro or in vivo optical imaging agents of tissues and organs in various biomedical applications. In one aspect, the present invention provides a method for imaging, the method comprising administering a compound of Formula I or Formula II.

Further aspects, objects, and advantages of the invention will become apparent upon consideration of the detailed description and figures that follow.

BRIEF DESCRIPTION OF THE DRAWINGS

FIG. 8 A) Binding results in U87GM cells with either a 17/RGD conjugate or IRDye® 800CW/RGD. B) Blocking assay in U87GM cells: 17/RGD conjugate (200 nM) addition with a serial dilution of unlabeled RGD (0.06-30 µM).

FIG. 9 Compound 16 and IRDye 800CW carboxylate clearance series shows very little difference between the two dyes, indicating good clearance in vivo: Dorsal (A) or ventral (B) views. A graphical representation of the whole-body core signal from the dorsal view is presented (C).

DETAILED DESCRIPTION OF THE INVENTION

Definitions

Figure 1:
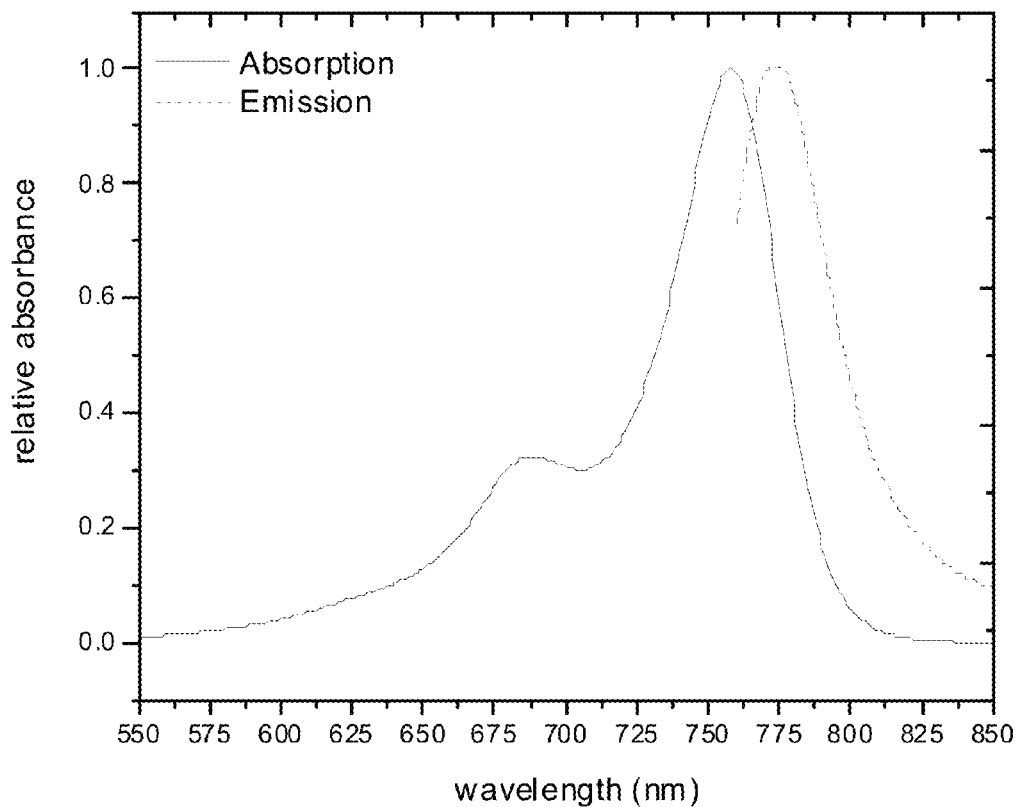
FIG. 1 shows the absorbance and emission spectra of compound 11 in phosphate-buffered saline (PBS). For emission, the y-axis indicates the dye's fluorescence as expressed in arbitrary units.

The terms "a," "an," or "the" as used herein not only include aspects with one member, but also include aspects with more than one member. For example, an embodiment of a method of imaging that comprises using a compound set forth in claim 1 would include an aspect in which the method comprises using two or more compounds set forth in claim 1.

"The term "about" as used herein to modify a numerical value indicates a close range around that explicit value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "about" is applied to describe the beginning of a numerical range, it applies to both ends of the range. Thus, "from about 700 to 850 nm" is equivalent to "from about 700 nm to about 850 nm." When "about" is applied to describe the first value of a set of values, it applies to all values in that set. Thus, "about 680, 700, or 750 nm" is equivalent to "about 680 nm, about 700 nm, or about 750 nm." However, when the modifier "about" is applied to describe only the end of the range or only a later value in the set of values, it applies only to that value or that end of the range. Thus, the range "about 2 to 10" is the same as "about 2 to about 10," but is different from the range "2 to about 10."

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride or mixed anhydride —OC(O)$R^a$ or —OC(N$R^a$)NH$R^b$, wherein $R^a$ and $R^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl. Preferred activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—$OC_4H_4NO_2$), sulfosuccinimidyloxy (—$OC_4H_3NO_2SO_3H$), -1-oxybenzotriazolyl(—$OC_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy). Preferred activated esters include succinimidyloxy and sulfosuccinimidyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double bond. Preferred alkenyl groups have 2 to about 12 carbon atoms. More preferred alkenyl groups contain 2 to about 6 carbon atoms. "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, and the like.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH=CH—, —$CH_2$—CH=CH—, —C($CH_3$)=CH—, —$CH_2$CH=CH$CH_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" as used herein includes an alkyl-O-alkylene-group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene-group wherein alkyl and alkylene are as defined herein. Representative alkoxycarbonylalkyl include methoxycarbonylmethyl, ethoxycarbonylmethyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 10 or 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylsulfonate ester" as used herein includes an alkyl-$SO_3$— group wherein the alkyl group is as defined herein. Preferred alkylsulfonate ester groups are those wherein the alkyl group is lower alkyl. Representative alkylsulfonate ester groups include mesylate ester (i.e., methylsulfonate ester).

An "optionally substituted" alkylsulfonate ester includes an alkylsulfonate ester as defined herein, wherein the aryl group is additionally substituted with from 0 to 3 halo, alkyl, aryl, haloalkyl, or haloaryl groups as defined herein. Preferred optionally substituted alkylsulfonate groups include triflate ester (i.e., trifluoromethylsulfonate ester).

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene-group wherein alkylthio and alkylene are defined herein. Representative alkylthioalkyl groups include methylthiomethyl, ethylthiopropyl, isopropylthioethyl, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amido" as used herein includes a group of formula $Y_1Y_2N$—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2N$—C(O)—), methylamido, dimethylamido, diethylamido, and the like. Preferably, "amido" is an —C(O)NRR' group where R and R' are members independently selected from the group consisting of H and alkyl. More preferably, at least one of R and R' is H.

"Amidoalkyl" as used herein includes an amido-alkylene-group wherein amido and alkylene are defined herein. Representative amidoalkyl groups include amidomethyl, amidoethyl, dimethylamidomethyl, and the like.

"Amino" as used herein includes a group of formula $Y_1Y_2N$— wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, tritylamino, and the like. Preferably, "amino" is an —NRR' group where R and R' are members independently selected from the group consisting of H and alkyl. Preferably, at least one of R and R' is H.

"Aminoalkyl" as used herein includes an amino-alkylene-group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Arylsulfonate ester" as used herein includes an aryl-$SO_3$ group wherein the aryl group is as defined herein. Representative arylsulfonate ester groups include phenylsulfonate ester.

An "optionally substituted" arylsulfonate ester includes an arylsulfonate ester as defined herein, wherein the aryl group is additionally substituted with from 0 to 3 halo, alkyl, aryl, haloalkyl, or haloaryl groups as defined herein. Preferred optionally substituted arylsulfonate esters include tosylate ester (i.e., p-tolylsulfonate ester).

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring of the compounds herein, a cationic counterion (e.g., the cation of a Group I metal such as sodium) must be added to balance the negative charge from additional sulfonato groups. Similarly, anionic counterions must be added to balance any additional cationic groups (e.g., most amino groups under physiological conditions).

"Biomolecule" as used herein includes a natural or synthetic molecule for use in biological systems. Preferred biomolecules include a protein, a peptide, an enzyme substrate, a hormone, an antibody, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragment of RNA, nucleotide triphosphates, acyclo terminator triphosphates, PNA, and the like. More preferred biomolecules include a protein, a peptide, an antibody, an avidin, a streptavidin, and the like. Even more preferred biomolecules include a peptide, an antibody, an avidin, and a streptavidin.

"Carboxy" and "carboxyl" as used herein include a HOC(O)— group (i.e., a carboxylic acid) or a salt thereof.

"Carboxyalkyl" as used herein includes a HOC(O)-alkylene-group wherein alkylene is defined herein. Representative carboxyalkyls include carboxymethyl (i.e., HOC(O)CH$_2$—) and carboxyethyl (i.e., HOC(O)CH$_2$CH$_2$—).

"Cycloalkenyl" as used herein includes a cyclic hydrocarbon group of 4 to about 15 carbon atoms that contains at least one carbon-carbon double. The cycloalkenyl ring may include from 0 to 6 R$^{14}$ substituents and 0 to 2 R$^L$ substituents, and when present, the ring-fused aryl or heteroaryl rings may also include from 0 to 4 R$^{14}$ substituents and 0 to 2 R$^L$ substituents. The R$^{14}$ and R$^L$ substituents are as otherwise defined herein. Preferred alkenyl groups have 5 to about 12 carbon atoms. More preferred alkenyl groups contain 7 to about 14 carbon atoms. Representative cycloalkenyl groups include cyclopentenyl, cyclohexenyl, "Cycloalkynyl" as used herein includes a cyclic hydrocarbon group of 5 to about 15 carbon atoms that contains at least one carbon-carbon triple bond. In a preferred aspect, the cyclic hydrocarbon may optionally be interrupted by a heteroatom (e.g., N, O, S; preferably N) and may include at least one ring-fused aryl or heteroaryl ring (e.g., DBCO or DBCO-1). The cycloalkynyl ring may include from 0 to 6 R$^{14}$ substituents and 0 to 2 R$^L$ substituents, and when present, the ring-fused aryl or heteroaryl rings may also include from 0 to 4 R$^{14}$ substituents and 0 to 2 R$^L$ substituents. The R$^{14}$ and R$^L$ substituents are as otherwise defined herein. In some aspect, the R$^L$ substituent includes a ring-fused heteroaryl group as part of the linking group with the biomolecule (e.g., the reaction of DBCO with an azide-substituted biomolecule). Preferred alkynyl groups have 5 to about 12 carbon atoms. More preferred alkynyl groups contain 7 to about 14 carbon atoms. Representative cycloalkynyl groups include cyclopentynyl, cyclohexynyl, cyclooctynyl, dibenzocyclooctynyl (or DBCO, which includes a nitrogen in the "octyne" ring or DBCO-1), BARAC, DIFO, DIBO, TMDIBO, DIFO3 and the like.

"Cycloalkynylcarbonyl" includes the definition of cycloalkynyl above with an exocylic carbonyl, for example, a dibenzocyclooctynylcarbonyl or C(O)DBCO, which includes a nitrogen in the "octyne" ring and an exocyclic carbonyl group, and the like.

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one sp$^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Cyanine dye" as used herein includes a compound having two substituted or unsubstituted nitrogen-containing heterocyclic rings joined by an unsaturated bridge. Examples include the structures of Formula I.

"Exocyclic alkene" or "exocyclic olefin" as used interchangeably herein includes an alkene having one alkene carbon that is part of a ring and the other alkene carbon not part of the same ring, though it may be included within a second ring. The second alkene carbon can be unsubstituted or substituted. If the second alkene carbon is disubstituted, the substituents can be the same (e.g., 1,1-dimethyl substitution) or different (e.g., 1-methyl-1-(2-ethoxyethyl) substitution). Examples of compounds with exocyclic alkenes include methylenecyclohexane; (E)-1-ethylidene-2,3-dihydro-1H-indene; pentan-3-ylidenecycloheptane; 2-cyclobutylidenepropan-1-ol; and (3-methoxycyclopent-2-enylidene) cyclohexane.

"Geminal" substituents as used herein include two or more substituents that are directly attached to the same atom. An example is 3,3-dimethyl substitution on a cyclohexyl or spirocyclohexyl ring.

"Halo" or "halogen" as used herein includes fluoro, chloro, bromo, or iodo.

"Haloalkyl" as used herein includes an alkyl group wherein the alkyl group includes one or more halo-substituents.

"Haloaryl" as used herein includes an alkyl group wherein the aryl group includes one or more halo-substituents.

"Heptamethine" as used herein includes a polymethine containing seven polymethine carbons. In a preferred embodiment, the heptamethine is substituted at the 4-position.

"Heteroatom" as used herein includes an atom other than carbon or hydrogen. Representative heteroatoms include O, S, and N. The nitrogen or sulphur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —C$_1$-C$_9$ alkylene-O—C$_1$-C$_9$ alkylene-). In some embodiments, a heteroatom is further substituted with an acyl, alkyl, aryl, cycloalkyl, heterocyclyl, or heteroaryl group (e.g., —N(Me)—; —N(Ac)—).

"Heteroaroyl" as used herein includes a heteroaryl-C(O)— group wherein heteroaryl is as defined herein. Representative heteroaroyl groups include thiophenoyl, nicotinoyl, pyrrol-2-ylcarbonyl, pyridinoyl, and the like.

"Heterocycloyl" as used herein includes a heterocyclyl-C(O)— group wherein heterocyclyl is as defined herein. Representative heterocycloyl groups include N-methyl prolinoyl, tetrahydrofuranoyl, and the like.

"Heterocyclyl" as used herein includes a non-aromatic saturated monocyclic or multicyclic ring system of about 3 to about 10 ring atoms, preferably about 5 to about 10 ring atoms, in which one or more of the atoms in the ring system is an element or elements other than carbon, e.g., nitrogen, oxygen or sulfur. Preferred heterocyclyl groups contain about 5 to about 6 ring atoms. A heterocyclyl group optionally comprises at least one sp$^2$-hybridized atom (e.g., a ring incorporating a carbonyl, endocyclic olefin, or exocyclic olefin). The prefix "aza," "oxa," or "thia" before heterocyclyl means that at least a nitrogen, oxygen or sulfur atom respectively is present as a ring atom. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylene" as used herein includes a bivalent heterocyclyl group. Representative cycloalkylenyl groups include 1,2-, 1,3-, or 1,4-piperidinylene as well as 2,3- or 2,4-cis- or trans-piperidinylene.

"Heteroaryl" as used herein includes an aromatic monocyclic or multicyclic ring system of about 5 to about 14 ring atoms, preferably about 5 to about 10 ring atoms, in which at least one of the atoms in the ring system is an element other than carbon, i.e., nitrogen, oxygen or sulfur. Preferred heteroaryls contain about 5 to about 6 ring atoms. The prefix "aza," "oxa," or "thia" before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

"Linking group" as used herein includes the atoms joining a compound of Formula I with a biomolecule. Table 1 includes a list of preferred bonds for linking groups (i.e., Column C); the linking group comprises the resulting bond and optionally can include additional atoms. See also R. Haugland, Molecular Probes Handbook of Fluorescent Probes and Research Chemicals, Molecular Probes, Inc. (1992). In one embodiment, $R^{16}$ represents a linking group precursor before the attachment reaction with a biomolecule, and $R^L$ represents the resultant attachment between the compound of Formula I and the biomolecule (i.e., $R^L$ comprises the linking group and the biomolecule linked thereby). Preferred reactive functionalities include phosphoramidite groups, an activated ester (e.g., an NHS ester), thiocyanate, isothiocyanate, maleimide and iodoacetamide.

"Methine carbon" or "polymethine carbon" as used herein includes a carbon that is directly connecting the two heterocyclic rings by means of the polymethine bridge. In a preferred embodiment, at least one polymethine carbon of a polymethine bridge is additionally substituted with another group such as alkyl, cycloalkyl, or aryl (e.g., —CH=CH—C(Ar)=CH—CH= or =CH—CH=C(Ar)—(CH=CH)$_2$—).

"Oxo" as used herein includes a group of formula >C=O (i.e., a carbonyl group —C(O)—).

"Pentamethine" as used herein includes a polymethine containing five polymethine carbons. In a preferred embodiment, the pentamethine is substituted at the 3-position.

A "photoactivatable moiety" as used herein includes a chemical group or molecule that, upon exposure to light, absorbs a photon to enter an excited state. The excited-state group or molecule undergoes a chemical reaction or series of reactions. Alternatively, the excitation changes the light-emitting properties of the group or molecules (e.g., photoactivatable fluorescent dyes). Examples of photoactivatable moieties include aryl azides, benzophenones (e.g., 4-benzoyloxybenzoic acid as well as its esters and amides), nitroaryl groups (e.g., 5-carboxymethoxy-2-nitrobenzyl (CMNB); α-carboxy-2-nitrobenzyl (CNB); 4,5-dimethoxy-2-nitrobenzyl (DMNB); 1-(4,5-dimethoxy-2-nitrophenyl)ethyl (DMNPE); nitrophenyl (NP); and 1-(2-nitrophenyl)ethyl (NPE) groups), coumarins, diazo groups, photoactivatable fluorescent dyes (e.g., 5-carboxyfluorescein-bis-(5-carboxymethoxy-2-nitrobenzyl)ether, β-alanine-carboxamide, succinimidyl ester), and tetrazoles.

"Polyene" as used herein includes a straight or branched bivalent hydrocarbon chain containing at least two "alkenylene" groups as defined herein that are in conjugation. The polyene is optionally substituted with one or more "alkylene group substituents" as defined herein. A portion of the polyene may be incorporated into a ring (i.e., =C(R)—, wherein R and the terminal bond are linked in a larger ring; or —C($R^1$)=C($R^2$)—, wherein $R^1$ and $R^2$ are linked in a larger ring). Representative polyenes include —CH=CH—CH=CH—, —CH=CH—C(Ar)=CH—CH=C(R)—, —C(R)=CH—CH=C(Ar)-(CH=CH)$_2$—, and the like.

"Polymethine" or "polymethine bridge" as used herein includes the series of conjugated, sp$^2$-hybridized carbons that form the unsaturated bridge directly connecting the two nitrogen-containing heterocyclic rings of a compound of Formula I. In a preferred embodiment, the polymethine has five or seven carbons directly connecting the heterocyclic rings (i.e., pentamethine or heptamethine).

"Phosphoramidityl" as used herein includes a trivalent phosphorous atom bonded to two alkoxy groups and an amino group.

"Spirocycloalkyl" as used herein includes a cycloalkyl in which geminal substituents on a carbon atom are replaced to form a 1,1-substituted ring.

"Sulfonato" as used herein includes an —SO$_3^-$ group, preferably balanced by a cation such as H$^+$, Na$^+$, K$^+$, and the like.

"Sulfonatoalkyl" as used herein includes a sulfonato-alkylene-group wherein sulfonato and alkylene are as defined herein. A more preferred embodiment includes alkylene groups having from 2 to 6 carbon atoms, and a most preferred embodiment includes alkylene groups having 2, 3, or 4 carbons. Representative sulfonatoalkyls include sulfonatomethyl, 3-sulfonatopropyl, 4-sulfonatobutyl, 5-sulfonatopentyl, 6-sulfonatohexyl, and the like.

In general, the unit prefix "u" as used herein is equivalent to "g" or "micro." For example, "ul" is equivalent to "μl" or "microliters."

Cyanine Dye Compounds

In one embodiment, the present invention provides a compound of Formula I:

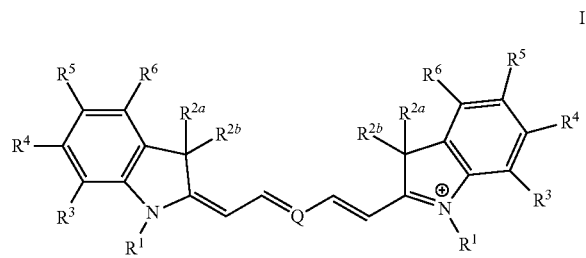

I wherein Q is a three-methine-carbon segment:

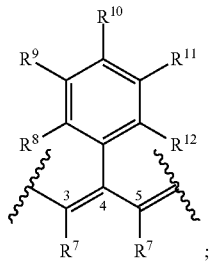

wherein the segment is the central portion of a seven-methine-carbon polymethine bridge.

In a preferred aspect, Q is a portion of a polymethine bridge that is a pentamethine:

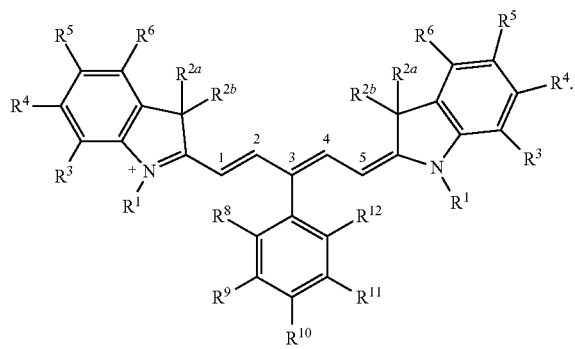

In a second preferred aspect, Q is a portion of a polymethine bridge that is a heptamethine:

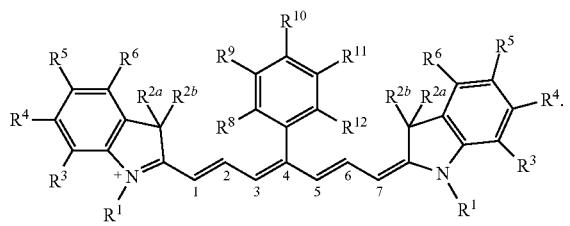

In an alternative preferred aspect, the polymethine bridge is a substituted heptamethine:

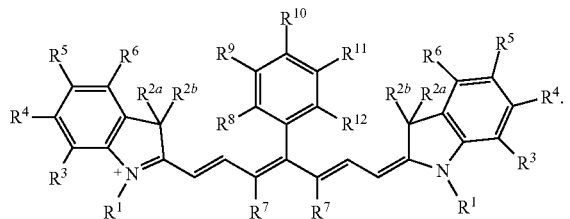

More preferably, the substituted heptamethine includes a cycloalkyl ring:

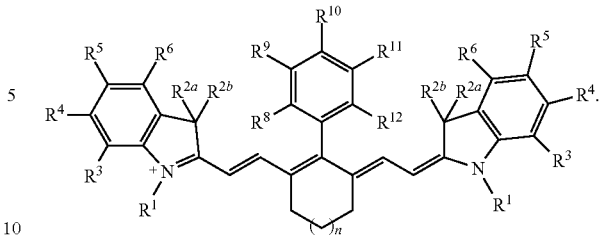

In a preferred aspect, a dye is symmetric. Non-symmetric dyes are often more difficult to synthesize in high purity and yield. (See U.S. Pat. No. 6,747,159 for some advantages of symmetric dyes). However, as set forth in the Examples, some embodiments of the present invention are non-symmetric dyes.

Each $R^1$ is an independently selected alkyl group that is additionally substituted with from 0 to 1 $R^{14}$ and from 0 to 1 -L-Y—Z; wherein the alkyl is optionally interrupted by at least one heteroatom.

In a preferred aspect, $R^1$ is not interrupted by a heteroatom. Alternatively, $R^1$ is interrupted by at least one ether, thioether, substituted amino, or amido group.

In a preferred aspect, $R^1$ is $C_1$-$C_{20}$ alkyl. In a more preferred aspect, $R^1$ is $C_1$-$C_{12}$ or $C_2$-$C_8$ alkyl. In a still more preferred aspect, $R^1$ is 2, 3, or 4.

In another preferred aspect, $R^1$ is $(CH_2)_r SO_3H$ or $(CH_2)_r SO_3^-$; and r is an integer from 1 to 20. In a more preferred aspect, r is 2, 3, or 4.

In still another preferred aspect, $R^1$ is an alkyl group that is additionally substituted with 1 $R^{14}$. In a more preferred aspect, the $R^{14}$ is carboxy or sulfonato. In a still more preferred aspect, $R^{14}$ is sulfonato. In a yet still more preferred aspect, $R^{14}$ is 3-sulfonatopropyl or 4-sulfonatobutyl.

In yet another preferred aspect, $R^1$ is an unbranched alkyl group that is additionally substituted with 1 $R^{14}$. In a more preferred aspect, $R^1$ is an unbranched alkyl group that is substituted with $R^{14}$ at the end of the alkyl group opposite to its attachment point to the cyanine dye heterocyclic nitrogen. In a still more preferred aspect, $R^1$ is 2-sulfonatoethyl, 3-sulfonatopropyl, 4-sulfonatobutyl, or 5-sulfonatopentyl. In a yet still more preferred aspect, $R^1$ is 3-sulfonatopropyl or 4-sulfonatobutyl; more preferably, $R^1$ is 3-sulfonatopropyl.

Each $R^{2a}$ and $R^{2b}$ is a member independently selected from the group consisting of alkyl, alkenyl, hydroxyalkyl, alkoxyalkyl, aminoalkyl, amidoalkyl, alkylthioalkyl, carboxyalkyl, alkoxycarbonylalkyl, or sulfonatoalkyl; wherein a carbon of the member is additionally substituted with from 0 to 1 -L-Y—Z; or, alternatively, a $R^{2a}$ and $R^{2b}$ pair, together with the ring carbon to which the $R^{2a}$ and $R^{2b}$ are bonded, join to form a spirocycloalkyl ring, wherein the spirocycloalkyl ring is additionally substituted with from 0 to 6 $R^{14}$ and from 0 to 1 -L-Y—Z, or an exocyclic alkene, wherein the exocyclic alkene is additionally substituted with from 0 to 2 $R^{14}$ and from 0 to 1 -L-Y—Z.

In a preferred aspect, all $R^{2a}$ are the same substituent. Alternatively, all $R^{2b}$ are the same substituent. More preferably, all $R^{2a}$ are the same substituent, and all $R^{2b}$ are the same substituent.

In another preferred aspect, $R^{2a}$ and $R^{2b}$ are the same. In a more preferred aspect, $R^{2a}$ and $R^{2b}$ are alkyl, alkenyl, aminoalkyl, carboxyalkyl, or sulfonatoalkyl. In a still more preferred aspect, $R^{2a}$ and $R^{2b}$ are alkyl, carboxyalkyl, or sulfonatoalkyl. In a yet still more preferred aspect, $R^{2a}$ and $R^{2b}$ are methyl.

In an alternative aspect, $R^{2a}$ and $R^{2b}$ are different. In a more preferred aspect, $R^{2a}$ is alkyl, and $R^{2b}$ is selected from the group of alkyl, alkenyl, aminoalkyl, carboxyalkyl, or sulfonatoalkyl. In a still more preferred aspect, $R^{2a}$ is alkyl, and $R^{2b}$ is selected from the group of alkyl, carboxyalkyl, or sulfonatoalkyl. Yet still more preferably, $R^{2a}$ is methyl.

In another preferred aspect, $R^{2a}$ and $R^{2b}$, together with the ring carbon to which $R^{2a}$ and $R^{2b}$ are bonded, join to form a spirocycloalkyl ring, wherein the spirocycloalkyl ring is additionally substituted with from 0 to 6 $R^{14}$. In a more preferred aspect, $R^{2a}$ and $R^{2b}$ form a cyclopentyl or sulfonatoalkyl. In a still more preferred aspect, $R^{14}$ is alkyl. In a yet still more preferred aspect, $R^{14}$ is methyl.

In an alternative aspect, $R^{2a}$ and $R^{2b}$, together with the ring carbon to which $R^{2a}$ and $R^{2b}$ are bonded, join to form an exocyclic alkene, wherein the exocyclic alkene is additionally substituted with from 0 to 2 $R^{14}$. In a more preferred aspect, the exocyclic alkene is symmetrically substituted (e.g., unsubstituted; dialkyl; dicyano). Alternatively, the exocyclic alkene is substituted with two $R^{14}$ groups. Still more preferably, the exocyclic alkene's $R^{14}$ substituent is cyano.

In an alternative preferred aspect, $R^{2a}$ and $R^{2b}$, together with the atom to which $R^{2a}$ and $R^{2b}$ are bonded, join to fowl a spirocycloalkyl ring. In a more preferred aspect, $R^{2a}$ and $R^{2b}$ form a cyclopentyl or cyclohexyl ring. In an alternative more preferred aspect, $R^{2a}$ and $R^{2b}$ form a cyclopentyl or cyclohexyl ring additionally substituted with from 0 to 6 $R^{14}$. In a still more preferred aspect, $R^{14}$ is alkyl.

Alternatively and preferably, the spirocycloalkyl ring has at least one pair of geminal $R^{14}$ alkyl substituents. More preferably, these geminal $R^{14}$ substituents are methyl (e.g., 3,3- or 4,4-dimethyl substitution).

Each $R^3$, $R^4$, $R^5$, and $R^6$ is a member independently selected from the group consisting of hydrogen, alkyl, alkenyl, halo, hydroxyl, alkoxy, amino, cyano, carboxyl, alkoxycarbonyl, amido, sulfonato, alkoxyalkyl, carboxyalkyl, alkoxycarbonylalkyl, and sulfonatoalkyl; wherein a carbon of the member is additionally substituted with from 0 to 1 -L-Y—Z; or, alternatively, a pair of said members that is selected from the group consisting of $R^3$ and $R^4$, $R^4$ and $R^5$, and $R^5$ and $R^6$, together with the pair of atoms to which the pair of said members is bonded, joins to form an aryl ring, wherein the aryl ring is additionally substituted with from 0 to 2 $R^{14}$ and from 0 to 1 -L-Y—Z.

In a first aspect, each $R^3$, $R^4$, $R^5$, and $R^6$ is a member independently selected from the group consisting of hydrogen, alkyl, alkenyl, halo, alkoxy, cyano, carboxyl, alkoxycarbonyl, amido, sulfonato, alkoxyalkyl, carboxyalkyl, alkoxycarbonylalkyl, and sulfonatoalkyl. In a preferred aspect, each $R^3$, $R^4$, $R^5$, and $R^6$ is a member independently selected from the group of hydrogen, alkyl, carboxy, carboxyalkyl, sulfanato, and sulfanatoalkyl. In a more preferred embodiment, each $R^3$, $R^4$, $R^5$, and $R^6$ is a member independently selected from the group of hydrogen and sulfanato.

In one aspect, at least one pair of $R^3$, $R^4$, $R^5$, or $R^6$ are the same (i.e., the $R''$ substituent is not independently selected, but is the same as the other $R''$ substituent). This aspect can be combined with other aspects specifying the number or type of dye substituents (e.g., exactly two members of the groups $R^3$, $R^4$, $R^5$, and $R^6$ are hydrogen, and the two members are the pair of $R^4$s). Alternatively, at least two, at least three, or all four pairs of $R^3$, $R^4$, $R^5$, or $R^6$ are the same. More preferably, the dye is symmetric or pseudo-symmetric (i.e., $R^1$, $R^{2a}$, and $R^{2b}$ are also not independently selected).

In an alternative aspect, at least one member of the groups $R^3$, $R^4$, $R^5$, and $R^6$ is hydrogen. Alternatively, exactly one member of the groups $R^3$, $R^4$, $R^5$, and $R^6$ is hydrogen. In a preferred aspect, at least one pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ is hydrogen. Alternatively, exactly two, exactly three, exactly four, exactly five, or exactly six members of the groups $R^3$, $R^4$, $R^5$, and $R^6$ are hydrogen. In another aspect, exactly four members of the groups $R^3$, $R^4$, $R^5$, and $R^6$ are hydrogen. Alternatively, exactly five members of the groups $R^3$, $R^4$, $R^5$, and $R^6$ are hydrogen. In a still more preferred aspect, $R^3$, $R^4$, and $R^6$ are hydrogen.

In another alternative aspect, at least one member of the groups $R^3$, $R^4$, $R^5$, and $R^6$ is sulfonato or sulfonatoalkyl. Alternatively, exactly one substituent selected from the groups $R^3$, $R^4$, $R^5$, and $R^6$ is sulfonato or sulfonatoalkyl. In a preferred aspect, $R^5$ is sulfonato. In still another aspect, both members of a pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ are each a member independently selected from the group of sulfonato or sulfonatoalkyl. Alternatively, exactly two, exactly three, exactly four, exactly five, or exactly six members of the groups $R^3$, $R^4$, $R^5$, and $R^6$ are each a member independently selected from the group of sulfonato or sulfonatoalkyl.

In another alternative aspect, at least one member of the group $R^3$, $R^4$, $R^5$, and $R^6$ is anionic at physiological pH (e.g., sulfonato —$SO_3^-$, carboxy —$CO_2^-$). Alternatively, exactly one member of the group $R^3$, $R^4$, $R^5$, and $R^6$ is anionic at physiological pH. In a preferred aspect, $R^5$ is anionic at physiological pH. In still another aspect, each member of a pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ is anionic at physiological pH. Alternatively, exactly two, exactly three, exactly four, exactly five, or exactly six members of the groups $R^3$, $R^4$, $R^5$, and $R^6$ are anionic at physiological pH. Alternatively, exactly two, exactly three, or exactly four members of the groups $R^3$, $R^4$, $R^5$, and $R^6$ are anionic at physiological pH.

In another alternative aspect, at least one member of the groups $R^3$, $R^4$, $R^5$, and $R^6$ is halo. Alternatively, exactly one substituent selected from the groups $R^3$, $R^4$, $R^5$, and $R^6$ is halo. In still another aspect, both members of a pair of substituents selected from the pairs $R^3$ and $R^4$; $R^3$ and $R^5$; $R^3$ and $R^6$; $R^4$ and $R^5$; $R^4$ and $R^6$; and $R^5$ and $R^6$ are each an independently selected halo. Alternatively, exactly two, exactly three, exactly four, exactly five, or exactly six members of the groups $R^3$, $R^4$, $R^5$, and $R^6$ are each an independently selected halo.

In a second aspect, a pair of members that is selected from the groups of $R^3$ and $R^4$; $R^3$ and $R^5$; $R^3$ and $R^6$; $R^4$ and $R^5$; $R^4$ and $R^6$; and $R^5$ and $R^6$, together with the pair of atoms to which the pair of members is bonded, joins to form an aryl ring (i.e., the aryl ring formed from $R''$ and $R''^{+1}$), wherein the aryl ring is additionally substituted with from 0 to 2 $R^{14}$. In a preferred aspect, the pair of members $R^5$ and $R^6$, together with the pair of atoms to which the pair of members is bonded, joins to form a phenyl ring that is additionally substituted with from 0 to 2 $R^{14}$. In a more preferred aspect, the phenyl ring is additionally substituted with from 1 to 2 $R^{14}$. In a still more preferred aspect, the phenyl ring is additionally substituted with 2 $R^{14}$.

In a preferred aspect, the $R^{14}$ substituents of the aryl ring formed from W and $R''^{+1}$ (e.g., the aryl ring formed from $R^5$ and $R^6$) are carboxy, carboxyalkyl, sulfonato, or sulfonatoalkyl. In a still more preferred aspect, the $R^{14}$ substituents are sulfonato or sulfonatoalkyl. In a yet still more preferred aspect, the benzindolinium $R^{14}$ substituents are sulfonato. In an alternative preferred aspect, the benzindolinium $R^{14}$ substituents are cyano.

Alternatively, in a preferred aspect, the compound has Formula Ia:

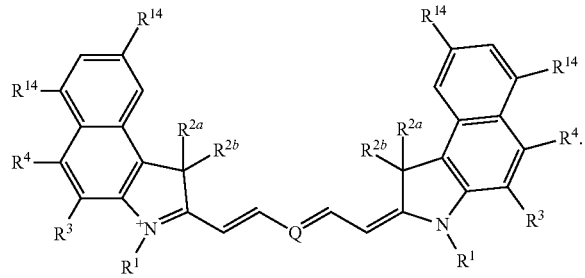

In a more preferred aspect, the aryl ring formed from $R''$ and $R''^{-1}$ is additionally substituted with from 1 to 2 $R^{14}$, and a $R^{14}$ substituent of the aryl ring is attached to a carbon adjacent to the ring junction with the indolinium ring. Alternatively, the aryl ring is additionally substituted with from 1 to 2 $R^{14}$, and a $R^{14}$ substituent of the aryl ring is attached to a carbon non-adjacent to the ring junction with the indolinium ring. Alternatively, the aryl ring is additionally substituted with one adjacent substituent and one non-adjacent substituent (e.g., the compound of Formula Ib).

Alternatively, in a preferred aspect, the compound has Formula Ib:

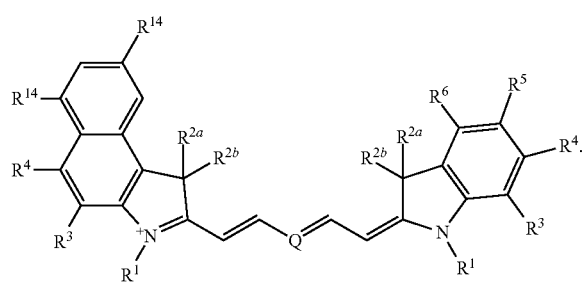

In a still more preferred aspect, the benzindolinium $R^{14}$ substituents of Formula Ia or Ib are carboxy, carboxyalkyl, sulfonato, or sulfonatoalkyl. In a still more preferred aspect, the benzindolinium $R^{14}$ substituents are sulfonato or sulfonatoalkyl. In a yet still more preferred aspect, the benzindolinium $R^{14}$ substituents are sulfonato.

Each $R^7$ is a member selected from the group of hydrogen and alkyl; or, alternatively, both $R^7$, together with the intervening segment of the polyene to which both $R^7$ are bonded, join to form a ring, wherein the ring is selected from the group of a cycloalkyl and a heterocyclyl ring, and wherein the ring is additionally substituted with from 0 to 3 $R^{14}$ and from 0 to 1 -L-Y—Z.

In one aspect, both $R^7$, together with the intervening segment of the polyene to which both $R^7$ are bonded, join to form a ring selected from the group of a five-membered ring and a six-membered ring, wherein the ring is additionally substituted with from 0 to 3 $R^{14}$. In a more preferred aspect, the ring is a six-membered ring (e.g., both $R^7$ combine to form a propylidene linking group). In a still more preferred aspect, the ring is cyclohexyl (i.e., both $R^7$ combine to form a —(CH$_2$)$_3$— linking group). In an alternative more preferred aspect, the ring is a five-membered ring. In another still more preferred aspect, the ring is cyclopentyl (i.e., both $R^7$ combine to form a —(CH$_2$)$_2$— linking group).

$R^8$, $R^9$, $R^{10}$, $R^{11}$ and $R^{12}$ are each a member independently selected from the group consisting of hydrogen, alkyl, alkenyl, halo, alkoxy, sulfonato, hydroxyl, amino, carboxyl, alkoxycarbonyl, cyano, amido, thioacetyl, and -L-Y—Z; wherein at least one member selected from the group consisting of $R^8$, $R^9$, and $R^{10}$ is -halo. More preferably, at least one member selected from the group consisting of $R^8$, $R^9$, and $R^{10}$ is fluoro or chloro.

In one aspect, $R^8$ is halo; more preferably, fluoro or chloro. Preferably, $R^9$, $R^{10}$, $R^{11}$, and $R^{12}$ are each a member independently selected from the group consisting of hydrogen, alkyl, alkoxy, halo, sulfonato, and -L-Y—Z.

In a second aspect, $R^8$ is hydrogen, alkyl, alkoxy, or halo. In another more preferred aspect, $R^8$ is fluoro; alternatively, $R^8$ is chloro.

In an alternative preferred aspect, $R^8$ is hydrogen.

Alternatively, $R^8$ is a carboxyalkyl. Preferably, $R^8$ is a lower alkyl group with a carboxy-substituent. More preferably, $R^8$ is 5-carboxypentyl, 4-carboxybutyl, 3-carboxypropyl, 2-carboxyethyl, or carboxymethyl. Still more preferably, $R^8$ is 5-carboxypentyl or 2-carboxyethyl.

Alternatively, $R^8$ is carboxyl, alkoxycarbonyl, or amido; more preferably, $R^8$ is carboxyl.

In one aspect, $R^{10}$ is halo; more preferably, fluoro or chloro. Preferably, $R^8$, $R^9$, $R^{11}$, and $R^{12}$ are each a member independently selected from the group consisting of hydrogen, alkyl, alkoxy, halo, sulfonato, and -L-Y—Z.

In a second aspect, $R^{10}$ is hydrogen, alkyl, alkoxy, or halo. In another more preferred aspect, $R^{10}$ is fluoro; alternatively, $R^{10}$ is chloro.

In an alternative preferred aspect, $R^{10}$ is hydrogen.

Alternatively, $R^{10}$ is a carboxyalkyl. Preferably, $R^{10}$ is a lower alkyl group with a carboxy-substituent. More preferably, $R^{10}$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl.

Alternatively, $R^{10}$ is carboxyl, alkoxycarbonyl, or amido; more preferably, $R^{10}$ is carboxyl.

In one aspect, $R^9$ is -L-Y—Z. Preferably, $R^8$, $R^{10}$, $R^{14}$, and $R^{12}$ are each a member independently selected from the group consisting of hydrogen, alkyl, alkoxy, halo, sulfonato, and -L-Y—Z.

In a second aspect, $R^9$ is hydrogen, alkyl, alkoxy, or halo. In another more preferred aspect, $R^9$ is fluoro; alternatively, $R^9$ is chloro.

In an alternative preferred aspect, $R^9$ is hydrogen.

Alternatively, $R^9$ is a carboxyalkyl. Preferably, $R^9$ is a lower alkyl group with a carboxy-substituent. More preferably, $R^9$ is 5-carboxypentyl, 4-carboxybutyl, 3-carboxypropyl, 2-carboxyethyl, or carboxymethyl. Still more preferably, $R^{10}$ is 5-carboxypentyl or 2-carboxyethyl.

Alternatively, $R^9$ is carboxyl, alkoxycarbonyl, or amido; more preferably, $R^9$ is carboxyl.

In one aspect, $R^{11}$ and $R^{12}$ are each a member independently selected from the group of hydrogen, alkyl, alkenyl, halo, alkoxy, sulfonato, hydroxyl, amino, carboxyl, alkoxycarbonyl, cyano, amido, thioacetyl, and -L-Y—Z. Preferably, $R^{11}$ and $R^{12}$ are each a member independently selected from the group of hydrogen, alkyl, halo, and sulfonato. More preferably, $R^{11}$ and $R^{12}$ are each a member independently selected from the group of hydrogen, halo, and sulfonato.

In a second aspect, $R^{11}$ is hydrogen, alkyl, alkoxy, or halo. In a more preferred aspect, $R^{11}$ is halo; preferably, $R^{11}$ is fluoro or chloro. In an alternative aspect, $R^{11}$ is hydrogen. Alternatively, $R^{10}$ and $R^{11}$ are hydrogen.

In a third aspect, $R^{12}$ is hydrogen, alkyl, alkoxy, or halo. In a more preferred aspect, $R^{12}$ is halo; preferably, $R^{12}$ is fluoro or chloro. In a still more preferred aspect, $R^{10}$ and $R^{12}$ are halogen, preferably fluoro or chloro. Alternatively, $R^{11}$ and $R^{12}$ are halogen, preferably fluoro or chloro. In a yet still more preferred aspect, $R^{10}$, $R^{11}$, and $R^{12}$ are halogen, preferably fluoro or chloro.

In a fourth aspect, the phenyl ring substituted with $R^8$, $R^9$, $R^{10}$, $R^{11}$, and $R^{12}$ is 1,2,3-substituted with independently selected substituents other than hydrogen, wherein the 1-substituent is the polymethine bridge (e.g., $R^8$ and $R^9$ are the same halo group; $R^8$ and $R^9$ are different halo groups; $R^8$ is halo- and $R^9$ is -L-Y—Z). Alternatively, the ring is 1,2,4-substituted. Alternatively, the ring is 1,2,5-substituted. Alternatively, the ring is 1,2,6-substituted. Alternatively, the ring is 1,3,4-substituted. Alternatively, the ring is 1,3,5-substituted. Alternatively, the ring is 1,3,6-substituted. Preferably, at least two of the substituents are halo; more preferably. fluoro or chloro.

In a fifth aspect, the phenyl ring substituted with $R^8$, $R^9$, $R^{10}$, $R^{11}$, and $R^{12}$ is 1,2,3,4-substituted with independently selected substituents other than hydrogen, wherein the 1-substituent is the polymethine bridge. Alternatively, the ring is 1,2,3,5-substituted. Alternatively, the ring is 1,2,3,6-substituted. Alternatively, the ring is 1,2,4,5-substituted. Alternatively, the ring is 1,2,4,6-substituted. Alternatively, the ring is 1,2,5,6-substituted. Alternatively, the ring is 1,3,4,5-substituted. Alternatively, the ring is 1,3,4,6-substituted. Alternatively, the ring is 1,3,5,6-substituted. Preferably, at least two of the substituents are halo; more preferably, fluoro or chloro. Alternatively and preferably, at least three of the substituents are halo; more preferably, fluoro or chloro.

In a sixth aspect, the phenyl ring substituted with $R^8$, $R^9$, $R^{10}$, $R^{11}$, and $R^{12}$ is 1,2,3,4,5-substituted with independently selected substituents other than hydrogen, wherein the 1-substituent is the polymethine bridge. Alternatively, the ring is 1,3,4,5,6-substituted. Alternatively, the ring is 1,2,4,5,6-substituted. Alternatively, the ring is 1,2,3,5,6-substituted. Alternatively, the ring is 1,2,3,4,6-substituted. Alternatively, the ring is independently substituted at each ring position.

Preferably, at least two of the substituents are halo; more preferably. fluoro or chloro. Alternatively, at least three of the substituents are halo; more preferably. fluoro or chloro (e.g., $R^8$, $R^{10}$, and $R^{12}$ are halo). Alternatively, at least four of the substituents are halo; more preferably. fluoro or chloro (e.g., $R^8$, $R^9$, $R^{11}$, and $R^{12}$ are halo).

In a seventh aspect, $R^8$, $R^9$, $R^{10}$, $R^{11}$, and $R^{12}$ are each a member independently selected from the group of hydrogen, alkyl, alkoxy, halo, sulfonato, and sulfonatoalkyl.

Fluoro substitution has been shown to increase quantum yield and photostability in fluorescein dyes as well as lowering dye $pK_a$. See Sun, W.-C. et al. *J. Org. Chem.* 1997, 62, 6469-6475. In an eighth aspect, at least one member of the group $R^8$, $R^9$, $R^{10}$, $R^{11}$, and $R^{12}$ is a fluoro substituent. Alternatively, at least one member of the groups $R^3$, $R^3$, $R^4$, $R^5$, $R^6$, and $R^{14}$ is a fluoro substituent. In yet another aspect, at least two members of the groups $R^3$, $R^4$, R, $R^6$, $R^8$, $R^9$, $R^{10}$, $R^{12}$, and $R^{14}$ are fluoro substituents. In yet another aspect, at least three members of $R^3$, $R^4$, R, $R^6$, $R^8$, $R^9$, $R^{10}$, $R^{11}$, $R^{12}$, and $R^{14}$ are fluoro substituents. In yet another aspect, at least four or at least five members of the groups $R^3$, $R^4$, R, $R^6$, $R^8$, $R^9$, $R^{10}$, $R^{11}$, $R^{12}$, and $R^{14}$ are fluoro substituents.

As demonstrated in the examples, chloro substitution also has a favorable effect on the dye properties, much as the fluoro group does. In a ninth aspect, at least one member of the group $R^8$, $R^9$, $R^{10}$, $R^{11}$, and $R^{12}$ is a chloro substituent. Alternatively, at least one member of the groups $R^3$, $R^4$, $R^5$, $R^6$, $R^8$, $R^9$, $R^{10}$, $R^{11}$, $R^{12}$, and $R^{14}$ is a chloro substituent. In yet another aspect, at least two members of the groups $R^3$, $R^4$, $R^5$, $R^6$, $R^8$, $R^9$, $R^{10}$, $R^{11}$, $R^{12}$, and $R^{14}$ are chloro substituents. In yet another aspect, at least three members of the groups $R^3$, $R^4$, R, $R^6$, $R^8$, $R^9$, $R^{10}$, $R^{11}$, $R^{12}$, and $R^{14}$ are chloro substituents. In yet another aspect, at least four or at least five members of the groups $R^3$, $R^4$, R, $R^6$, $R^8$, $R^9$, $R^{10}$, $R^{11}$, $R^{12}$, and $R^{14}$ are chloro substituents.

Each $R^{13}$ is a member independently selected from the group of hydroxyl, amino, carboxyl, and alkoxycarbonyl. In a preferred embodiment, $R^{13}$ is carboxyl or alkoxycarbonyl. In a more preferred embodiment, $R^{13}$ is carboxyl. Alternatively, $R^{13}$ is cyano.

Each $R^{14}$ is a member independently selected from the group consisting of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the alkyl or alkenyl is additionally substituted with from 0 to 1 $R^{13}$ and from 0 to 1 -L-Y—Z. In a preferred aspect, $R^{14}$ is alkyl, alkenyl, carboxyl, alkoxycarbonyl, amido, alkoxycarbonylalkyl, halo, sulfonato, or sulfonatoalkyl. Alternatively, $R^{14}$ is carboxyalkyl, hydroxyalkyl, halo, sulfonato, or sulfonatoalkyl. In an alternative aspect, $R^{14}$ is alkyl or alkyl substituted with 1 $R^{13}$. Alternatively, $R^{14}$ is halo or sulfonato. Alternatively, $R^{14}$ is sulfonato.

Each L is an optional member independently selected from the group consisting of a bond, a $C_1$-$C_{20}$ alkylene, and a $C_1$-$C_{20}$ alkenylene; wherein the alkylene or alkenylene is optionally interrupted by at least one heteroatom. In a preferred aspect, L is a bond, with the proviso that L is not a bond when that would produce a highly unstable structure (e.g., N-L-$R^{13}$, if $R^{13}$ is —CO$_2$H). Alternatively, L is a $C_1$-$C_{14}$ alkylene; more preferably, L is a $C_1$-$C_{10}$ alkylene or a $C_1$-$C_6$ alkylene. Alternatively, L is a $C_1$-$C_{12}$ alkylene interrupted by ether linkages (e.g., a polyethylene glycol oligomer).

In a preferred aspect, the alkylene or alkenylene is not interrupted by a heteroatom. Alternatively, L is interrupted by at least one ether, thioether, substituted amino, or amido group.

Each Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —NZ—, —NZC(O)—, and —C(O)NZ—. In a preferred aspect, Y is a bond. Alternatively, Y is —O—. Alternatively, Y is an amido group optionally substituted with $R^{15}$ at the amido nitrogen.

Each Z is independently selected from the group consisting of $R^{13}$ and $R^{16}$. In a more preferred aspect, Z is $C_1$-$C_6$ alkyl. Alternatively, Z is interrupted by ether linkages (e.g., a polyethylene glycol oligomer). In a still more preferred aspect, Z is carboxyalkyl or alkyl with an activated acyl substituent. In a yet still more preferred aspect, Z is 5-carboxypentyl or 4-carboxybutyl.

In an alternative preferred aspect, Z is a carboxyalkyl. Preferably, Z is a lower alkyl group with a carboxy-substituent. More preferably, Z is 5-carboxypentyl, 4-carboxybutyl, 3-carboxypropyl, 2-carboxyethyl, or carboxymethyl. Still more preferably, Z is 5-carboxypentyl or 2-carboxyethyl.

In another alternative preferred aspect, -L-Y— is (CH$_2$)$_t$; Z is carboxyl or activated acyl; and t is an integer from 0 to 10.

In still another alternative preferred aspect, the Z group's L group is a bond, and $R^{13}$ or $R^{16}$ is connected directly to -L-Y— or directly bonded to the phenyl ring itself if L and Y are also bonds.

In yet still another alternative preferred aspect, -L-Y—Z has at least three carbons. Alternatively, Z has at least three carbons.

In yet still another alternative preferred aspect, -L-Y—Z has at least four carbons. Alternatively, Z has at least four carbons.

In an alternative embodiment, —Y—Z is a member selected from the group consisting of —N(Z)$_2$, —N(Z)C(O)Z, and —C(O)N(Z)$_2$, and the two Z groups may optionally be linked to form a cycloalkynyl group. Examples of —N(Z)$_2$ cycloalkynyl groups are DBCO or DBCO-1, which are shown below:

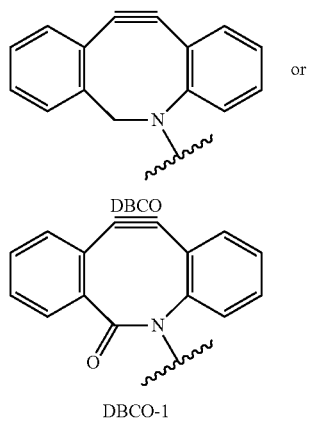

DBCO

DBCO-1

Each $R^{14}$ is a member independently selected from the group of alkyl, alkenyl, halo, hydroxyl, alkoxy, amino, amido, amidoalkyl, cyano, cyanoalkyl, carboxyl, alkoxycarbonyl, amido, sulfonato, sulfonatoalkyl, thioacetyl, thioacetylalkyl, alkoxycarbonylalkyl, and alkoxyalkyl; wherein the $R^{14}$ alkyl or alkenyl is additionally substituted with from 0 to 1 $R^{13}$. In a preferred aspect, $R^{14}$ is alkyl, alkenyl, carboxyl, alkoxycarbonyl, amido, or alkoxycarbonylalkyl. Alternatively, $R^{14}$ is sulfonato. In a more preferred aspect, $R^{14}$ is alkyl or alkyl substituted with 1 $R^{13}$. Alternatively, $R^{14}$ is carboxyalkyl, hydroxyalkyl, or sulfonatoalkyl.

Each $R^{15}$ is a member independently selected from the group consisting of alkyl and alkoxycarbonylalkyl; wherein the alkyl is optionally interrupted by at least one heteroatom.

In a preferred aspect, the alkyl is not interrupted by a heteroatom. In a preferred aspect, $R^{15}$ is alkyl. In a more preferred aspect, $R^{15}$ is lower alkyl.

Alternatively, L is interrupted by at least one ether, thioether, substituted amino, or amido group. Preferably, $R^{15}$ is interrupted by at least one ether group (e.g., a polyethylene glycol oligomer).

Each $R^{16}$ is independently a member selected from the group consisting of activated acyl, acrylamido, optionally substituted alkylsulfonate ester, azido, optionally substituted arylsulfonate ester, optionally substituted amino, aziridino, boronato, cycloalkynyl, cycloalkynylcarbonyl, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido, a pegylated alkynyl, a pegylated cycloalkynyl, an ortho substituted phosphinyl aryl ester (e.g., TPPME), a spirocycloalkynyl, and an ortho substituted phosphine oxide aryl ester.

In one aspect, each $R^{16}$ is independently a member selected from the group consisting of activated acyl, acrylamido, optionally substituted alkylsulfonate ester, alkynyl, optionally substituted arylsulfonate ester, amino, azido, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, and vinyl sulfonyl. In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

In certain aspects, $R^{16}$ has the following structures:

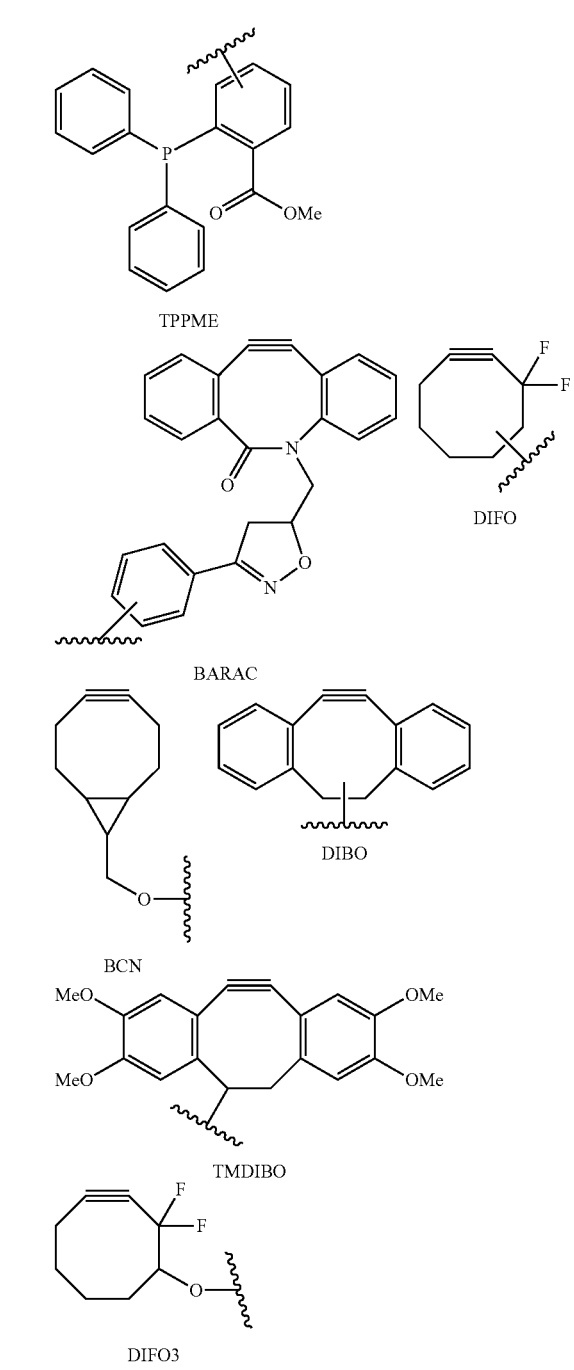

TPPME

DIFO

BARAC

DIBO

BCN

TMDIBO

DIFO3

In a preferred aspect, $R^{16}$ is activated acyl, maleimidyl, phosphoramidityl, or glycidyl. In a more preferred embodiment, $R^{16}$ is activated acyl. Alternatively, $R^{16}$ is activated ester. In a still more preferred embodiment, $R^{16}$ is succinimidyloxy-ester or sulfosuccinimidyloxy-ester.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In an alternative embodiment, the compound has a balanced charge in which positively and negatively charged substituents are balanced so that the dye molecule has a net charge of −1, 0, or +1 (preferably, 0), even without its counterions (i.e., the dye counterion has a net charge of −1, 0, or +1). In some aspects, this net charge is produced by including numbers of positively and negatively charged substituent groups that produce a dye net charge of −1, 0, or +1. This type of charge balancing is discussed in U.S. Provisional Application 61/150,522 (filed Feb. 9, 2009) and WO 2010/091243 (filed Feb. 5, 2010), which are incorporated by reference.

In a preferred aspect, -L-Y—Z is —(CH$_2$)$_4$CO$_2$H or an ester derivative thereof. Alternatively, -L-Y—Z is —(CH$_2$)$_2$CO$_2$H or an ester derivative thereof. Preferably, each $R^3$, $R^4$, $R^5$, and $R^6$ are a member independently selected from the group of hydrogen, alkyl, halo, and sulfonato.

In certain aspects, an activated acyl group is present in place of the carboxy group. In a still more preferred aspect, the activated acyl group is an activated ester. In a still yet more preferred aspect, the activated ester is a succinimidyloxyester.

In a first aspect, the compound of Formula I, Ia, Ib, II, IIa, or IIb fluoresces at a wavelength within the range of about 550 nm to about 1000 nm. Preferably, the compound fluoresces at a wavelength within the range of about 600 nm to about 850 nm. More preferably, the compound fluoresces at a wavelength within the range of about 600 nm to about 725 nm. Alternatively, the compound fluoresces at a wavelength within the range of about 725 nm to about 850 nm.

Alternatively, the compound of Formula I, Ia, Ib, II, IIa, or IIb fluoresces at a wavelength within the range of about 600 nm to about 1000 nm. Preferably, the compound fluoresces at a wavelength within the range of about 600 nm to about 725 nm. Alternatively, the compound fluoresces at a wavelength within the range of about 650 nm to about 850 nm. Alternatively, the compound fluoresces at a wavelength within the range of about 725 nm to about 850 nm.

One preferred aspect of the instant invention is compounds with the same substituents on both heterocyclic rings (e.g., both $R^1$ are the same sulfonatoalkyl substituent, optionally with different counterions to balance charge). This provides advantages during the synthesis and purification of the compound.

The present application broadly encompasses all possible stereoisomers of the compounds as described herein, including the various diasteromers, enantiomers, and olefin stereoisomers apparent to one of skill in the art. This application is further directed to all methods of purifying cyanine dye compound stereoisomers that are well-known in the art as well as the purified compounds available by these methods.

Preparation of Compounds of Formula I

In one aspect, the preferred cyanine compounds set forth in pending U.S. patent application Ser. No. 12/065,391 (US 2008/0267883 A1). A representative procedure for a Schiff base is included in U.S. Pat. No. 6,747,159 (Ar=Ph; pyridine/Ac$_2$O, Δ). The substituent can optionally be modified after the synthesis of the polymethine bridge (e.g., deprotected, activated for reaction with a biomolecule, or reacted to form a linking group).

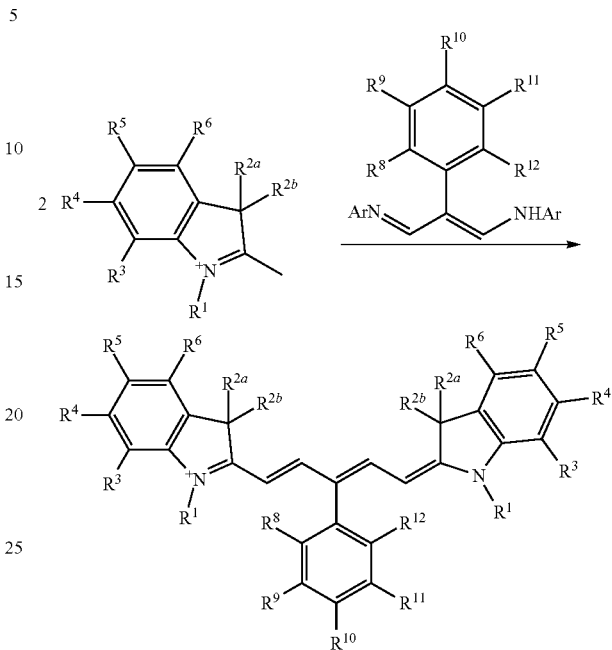

In another aspect, the preferred cyanine compounds of Formula I, Ia, or Ib are prepared by means of an organometallic coupling to incorporate a substituent to the polymethine bridge. More preferably, the substituent is installed by means of a palladium coupling. The substituent can optionally be modified after its inclusion (e.g., deprotected, activated for reaction with a biomolecule, or reacted to form a linking group).

The Miyaura-Suzuki reaction, also known as the Suzuki coupling, has been extensively used in organic synthesis since its discovery: Miyaura, N.; Yamada, K.; Suzuki, A. *Tetrahedron Lett.* 1979, 36, 3437-3440. Recently a Suzuki coupling was used to install a substituted aryl substituent at the central position of a heptamethine bridge in a water-soluble cyanine dye: Lee, H.; Mason, J. C.; Achilefu, S. *J. Org. Chem.* 2006, 71, 7862-7865.

However, because many cyanine dyes decompose under standard Suzuki coupling conditions of heating with a base, few examples of its use for the synthesis of cyanine dyes are known.

In a particularly preferred aspect of the instant invention, the substituent of a compound of Formula I is incorporated by means of a Suzuki coupling reaction, some of which are detailed in the examples of this specification. In one embodiment, the polymethine substrate for the Suzuki coupling is a 3-halopentamethine or a 4-haloheptamethine. In a preferred embodiment, the halo-substituent is a chloride or a bromide. In a more preferred embodiment, the halo-substituent is a bromide.

Other means of preparing cyanine dyes and their synthetic precursors are included in Hamer, F. M., *Cyanine Dyes and Related Compounds*, Weissberger, Mass., ed. Wiley Interscience, N.Y. 1964; and Mojzych, M., Henary, M. "Synthesis of Cyanine Dyes," *Top. Heterocycl. Chem.*, vol. 14, Springer Berlin, Heildelberg, 2008, pp. 1-9. Further, U.S. Pat. Nos. 4,337,063; 4,404,289; and 4,405,711 describe a synthesis for a variety of cyanine dyes having N-hydroxysuccinimide active ester groups. U.S. Pat. No. 4,981,977 describes a synthesis for cyanine dyes having carboxylic acid groups. U.S. Pat. No. 5,268,486 discloses a method for making arylsulfonate cyanine dyes. U.S. Pat. No. 6,027,709 discloses methods for making cyanine dyes having phosphoramidite groups. U.S. Pat. No. 6,048,982 discloses methods for making cyanine dyes having a reactive group selected from the group of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

One common synthetic route involves preparing substituted or unsubstituted indolesulfonate quaternary salts according to procedures that are well-known in the art, some of which are detailed in the examples of this specification. Particularly preferred indole quaternary salts include, among others, indolesulfonate and benzindolesulfonate quaternary salts, which are exemplified in this specification.

The pair of synthesized salts are then reacted with a dialdehyde or a dialdehyde equivalent (e.g., a Schiff base) to form the polymethine bridge by means of techniques and reaction conditions that are well-known in the art, some of which are detailed in the examples of this specification. Preferably, one of the dialdehydes is protected or masked to allow incorporation of one polycyclic side of the bridge (e.g., the indoline ring), followed by deprotection or unmasking of the aldehyde and by incorporation or construction of the other polycyclic group (e.g., the pyrrolopyridine). Schiff bases can be purchased from commercial suppliers (e.g., Sigma-Aldrich) or prepared according to procedures that are well-known in the art (e.g., the method of Example 5).

Methods of Labeling Biomolecules

The cyanine compounds of Formula I can be attached to biomolecules, which are defined above. Methods of linking dyes to various types of biomolecules are well-known in the art. For a through review of, e.g., oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

"Click" chemistry provides one possible way for linking the inventive dyes to biomolecules. Click chemistry uses simple, robust reactions, such as the copper-catalyzed cycloaddition of azides and alkynes, to create intermolecular linkages. For a review of click chemistry, see Kolb, H. C.; Finn, M. G.; Sharpless, K. B. *Angew. Chem.* 2001, 40, 2004.

Connection (or ligation) of two fragments to make a larger molecule or structure is often achieved with the help of so-called "click chemistry" described by Sharpless et al. *Angew. Chem., Int. Ed.* 40: 2004 (2001). This term is used to describe a set of bimolecular reactions between two different reactants such as azides and acetylenes. The formation of 1,2,3-triazoles in 1,3-dipolar cycloaddition of azides to a triple bond is known, but because the activation energy of acetylene-azide cycloaddition is relatively high, the reaction is slow under ambient conditions.

The utility of the reaction of azides with alkynes was expanded by the discovery of Cu (I) catalysis. 1,3-cycloaddition of azides to terminal acetylenes in the presence of catalytic amounts of cuprous salts is facile at room temperature in organic or aqueous solutions.

U.S. Pat. No. 7,807,619 to Bertozzi et al. teaches modified cycloalkyne compounds and method of use of such compounds in modifying biomolecules. Bertozzi et al. teach a cycloaddition reaction that can be carried out under physiological conditions. As disclosed therein, a modified cycloalkyne is reacted with an azide moiety on a target biomolecule, generating a covalently modified biomolecule.

The present invention provides cyanine dyes with click chemistry functionalities useful for labeling biomolecules. As such, in one aspect, the present invention provides compounds of Formula I or II, in which I one embodiment, each $R^{16}$ is independently a member selected from the group consisting of activated acyl, acrylamido, optionally substituted alkylsulfonate ester, azido, optionally substituted arylsulfonate ester, amino, azido, aziridino, boronato, diazo, formyl, glycidyl, halo, haloacetamidyl, haloalkyl, haloplatinato, halotriazino, hydrazinyl, imido ester, isocyanato, isothiocyanato, maleimidyl, mercapto, phosphoramidityl, a photoactivatable moiety, vinyl sulfonyl, alkynyl, a pegylated azido group, and a pegylated alkynyl group; and in which at least one $R^{16}$ is independently a member selected from the group azido, alkynyl, a pegylated azido and a pegylated alkynyl.

In yet other aspects, the present invention relates to two components that interact with each other to form a stable covalent bio-orthogonal bond. Bio-orthogonal reactions are reactions of materials with each other, wherein each material has limited or essentially no reactivity with functional groups found in vivo. These components are of use in chemical and biological assays, as chemical reagents, medical imaging and therapy, and more particularly, in nucleic acid modification techniques. According to a particular embodiment of the invention, the covalent bio-orthogonal bond is obtained by the [3+2]cycloaddition of azides and alkynes.

In still other aspects, one of the two components that interact with each other to form a stable covalent bio-orthogonal bond is a near infrared dye, such as a cyanine dye. In a preferred aspect, the cyanine dyes of the present invention comprise either an azide or an alkyne group for use as a reactant in a click chemistry reaction and the other reactant is a biomolecule such as a nucleotide comprising either an alkyne or azide group.

Azide reactive groups such as an alkyne compounds can react with at least one 1,3-dipole-functional compound such as an alkyne reactive group (e.g., a azido group) in a cyclization reaction to form a heterocyclic compound. In certain embodiments, the reaction can be carried out in the presence of an added catalyst (e.g., Cu(I)). In other embodiments, the reaction is carried out in the absence of such catalysts. Exemplary 1,3-dipole-functional compounds include, but are not limited to, azide-functional compounds, nitrile oxide-functional compounds, nitrone-functional compounds, azoxy-functional compounds, and/or acyl diazo-functional compounds. Preferably, azide-functional compounds are used.

Suitable biomolecule moieties for click reaction include, for example, monomeric and polymeric derivatives of nucleotides, carbohydrates, amino acids, lipids, glycols, alkanes, alkenes, arene, silicates, as well as biologically active and inactive compounds obtained from nature or from artificial synthesis.

Other suitable biological molecules include those having a azido or alkynyl functionality, which include, but are not limited to, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like. These biological molecules will in turn be reacted with the dye compounds of the present invention comprising either an azide or an alkyne group for use in click chemistry reactions.

In one aspect, the cyanine compounds of Formula I have sufficient solubility in aqueous solutions that once they are conjugated to a soluble ligand or biomolecule, the ligand or biomolecule retains its solubility. In certain instances, the bioconjugates also have good solubility in organic media (e.g., DMSO or DMF), which provides considerable versatility in synthetic approaches to the labeling of desired materials.

In another aspect, the present invention provides a method or process for labeling a ligand or biomolecule with a compound of Formula I, the method comprising: contacting a ligand or biomolecule with a compound having Formula I, Ia, or Ib to generate the corresponding bioconjugate compound of Formula II, IIa, or IIb.

In one preferred embodiment, the $R^{16}$ group or the $R^{13}$ group reacts with a thiol, a hydroxyl, a carboxyl, or an amino group on a biomolecule, forming a linking group between the dye and the biomolecule. In a more preferred embodiment, this reaction is carried out in mixtures of aqueous buffer and an organic solvent such as DMF at pH 8 to 9. Alternatively, this reaction is carried out in distilled water or in an aqueous buffer solution. For thiols or for acidic groups, a pH of 7 or lower is preferred for the reaction solvent, especially if a substrate also contains a reactive amino group.

Selected examples of reactive functionalities useful for attaching a compound of Formula I to a ligand or biomolecule are shown in Table 1, wherein the bond results from the reaction of a dye with a ligand or biomolecule. Column A of Table 1 is a list of the reactive functionalities, which can be on the compound of Formula I or the biomolecule. Column B is a list of the complementary reactive groups (preferably, a carboxyl, hydroxyl, thiol, or amino functionality), which can be on the biomolecule or the compound of Formula I, and which react with the indicated functionality of Column A to form the bond of Column C. Those of skill in the art will know of other bonds suitable for use in the present invention.

TABLE 1

Exemplary Bonds for Linking Groups

| A<br>Reactive Functionality<br>(Compound of Formula I<br>or Biomolecule) | B<br>Complementary<br>Group (Biomolecule<br>or Compound<br>of Formula I) | C<br>Resulting<br>Linking<br>Group |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | amides/imides |
| aryl halides | thiols | thiophenols |
| aryl halides | amines | aryl amines |
| azides | alkynes | 1,2,3-triazoles |
| azides | ester with phosphine reagent (e.g., o-diphenylphosphino group) | amide (and phosphine oxide) |

TABLE 1-continued

Exemplary Bonds for Linking Groups

| A<br>Reactive Functionality<br>(Compound of Formula I<br>or Biomolecule) | B<br>Complementary<br>Group (Biomolecule<br>or Compound<br>of Formula I) | C<br>Resulting<br>Linking<br>Group |
|---|---|---|
| aziridines | thiols | thioethers |
| boronates | glycols | boronate esters |
| boronates/boronic acids | aryl halides | C-C bond to aryl ring |
| boronates/boronic acids | alkenyl halides | C-C bond to alkenyl group |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| electron-rich diene | dienophile (e.g., electron-poor alkene) | cyclohexene (Diels-Alder cycloaddition) |
| epoxides | thiols | thioethers |
| epoxides | amines | alkyl amines |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| photoactivatable group | varies; see definition | varies; see definition |
| quadricyclanes | π-electrophile (e.g., Ni bis(dithiolene)) | norbornene cycloaddition product |
| silyl halides | alcohols | silyl ethers |
| sulfonate esters | amines/anilines | alkyl amines |
| sulfonate esters | carboxylic acids | esters |
| sulfonate esters | thiols | thioethers |
| sulfonate esters | alcohols/phenols | ethers |
| sulfonyl halides | amines/anilines | sulfonamides |
| 1,2,4,5-tetrazine | alkene | dihydropyradazine |
| vinyl sulfonyl | thiols | thioethers |
| vinyl sulfonyl | activated diene | cyclohexenyl (Diels-Alder) |

*Activated esters, as understood in the art, generally have the formula —C(O)OM, where —OM is a leaving group (e.g. succinimidyloxy (—OC$_4$H$_4$NO$_2$), sulfosuccinimidyloxy (—OC$_4$H$_3$NO$_2$SO$_3$H), -1-oxybenzotriazolyl (—OC$_6$H$_4$N$_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)R$^a$ or —C(O)OC(NR$^a$)NHR$^b$, wherein R$^a$ and R$^b$ are members independently selected from the group consisting of C$_1$-C$_6$ alkyl, C$_1$-C$_6$ perfluoroalkyl, C$_1$-C$_6$ alkoxy, cyclohexyl, 3-dimethylaminopropyl, or N-morpholinoethyl).
**Acyl azides can also rearrange to isocyanates.

Some methods of forming linking groups include those taught in Sletten and Bertozzi, *J. Am. Chem. Soc.* electronic publication at dx.doi.org/10.1021/ja2072934; Devaraj and Weissleder, *Acc. Chem. Res.* electronic publication at dx.doi.org/10.1021/ar200037t; Krishnamoorthy and Begley, *J. Am. Chem. Soc.* electronic publication at dx.doi.org/10.1021/ja1034107; and the like.

When linking a compound of Formula I having a carboxylic acid with an amine-containing ligand or biomolecule, the carboxylic acid can first be converted to a more reactive form, e.g, a N-hydroxy succinimide (NHS) ester or a mixed anhydride, by means of an activating reagent. The amine-containing ligand or biomolecule is treated with the resulting activated acyl to form an amide linkage. In a more preferred embodiment, this reaction is carried out in aqueous buffer at pH 8 to 9 with DMSO or DMF as an optional co-solvent. Alternatively, this reaction is carried out in distilled water or in an aqueous buffer solution.

Similarly, the attachment of an isocyanate- or isothiocyanate-containing compound of Formula I is analogous to the procedure for the carboxy dye, but no activation step is required. The amine-containing ligand or biomolecule is treated directly with the activated acyl compound to form a urea or a thiourea linkage. In a more preferred embodiment, the reaction is carried out in aqueous buffer at pH 9 to 10 with DMSO or DMF as an optional co-solvent. Alternatively, this reaction is carried out in distilled water or in an aqueous buffer solution.

If the compound of Formula I or biomolecule has a reactive hydroxyl group, it can be linked to a ligand or biomolecule by means of phosphoramidite chemistry, which ultimately forms a phosphate linkage between the dye and the biomolecule. For examples of such labeling methods, see U.S. Pat. No. 6,027,709, which discloses many preferred linking groups, linking methods, and biomolecules that can be readily labeled. In one embodiment, solid-phase synthesis is preferred, as disclosed in U.S. Pat. No. 6,027,709.

In a preferred embodiment, the biomolecule is DNA or RNA. Use of phosphoramidite chemistry allows labeling of a DNA or an RNA during the synthesis process. The protected nucleotide is labeled while attached to a solid-phase support. The free 5'-OH group is reacted with the phosphoramidite and a tetrazole activator to form a phosphite linkage which subsequently is oxidized to phosphate. The labeled DNA or RNA is then cleaved from the solid phase by means of ammonia or by another standard procedure.

It is generally preferred to prepare a phosphoramidite of a cyanine dye to label DNA molecules in a DNA synthesizer. It is also preferred to attach the dye to the 5' end of a protected, support-bonded oligonucleotide through standard phosphoramidite chemistry. For a list of preferred label terminators for use in DNA sequencing, see U.S. Pat. No. 5,332,666.

In another preferred embodiment, the biomolecule is an antibody. It is preferred that antibody labeling is carried out in a buffer optionally including an organic co-solvent, under basic pH conditions, and at room temperature. It is also preferred that the labeled antibody be purified by dialysis or by gel permeation chromatography using equipment such as a SEPHADEX® G-50 column to remove any unconjugated compound of Formula I. Those of skill in the art will know of other ways and means for purification.

In still another preferred embodiment, the biomolecule contains a thiol group that forms the linking group by reaction with a maleimidyl substituent at $R^{16}$. In a more preferred embodiment, the biomolecule is a protein, a peptide, an antibody, a thiolated nucleotide, or a thiolated deoxynucleotide.

In yet other aspects, the linking group or biomolecule comprises a polymer. In a preferred embodiment, the polymer is a member selected from the group of a PEG, a copolymer of PEG-polyurethane, and a copolymer of PEG-polypropylene. In still yet other aspects, the linking group is a member selected from the group of a polysaccharide, a polypeptide, an oligosaccharide, a polymer, a co-polymer and an oligonucleotide.

In one aspect, biomolecules can be labeled according to the present invention by means of a kit. In certain instances, the kit comprises a buffer and a dye as disclosed in the instant application (i.e., a compound of Formula I or Formula Ia). Preferably, the kit contains a coupling buffer such as 1 M $KH_2PO_4$ (pH 5), optionally with added acid or base to modify the pH (e.g., pH 8.5 is preferred for reactions with succinimide esters and pH 7 is preferred for reactions with maleimides). Preferably, the buffer has a qualified low fluorescence background.

Optionally, the kit can contain a purification sub-kit. After labeling a biomolecule with a preferred dye, the labeled biomolecule may be separated from any side reaction products and any free hydrolyzed product resulting from normal hydrolysis. For biomolecules containing 13 or fewer amino acids, preparative thin layer chromatography (TLC) can remove impurities. In certain instances, preparative TLC, optionally performed with commercially available TLC kits, can be used to purify dye-labeled peptides or proteins.

For larger biomolecules such as larger peptides or proteins, a SEPHADEX® G-15, G-25, or G-50 resin may remove unwanted derivatives. In certain instances, a Gel Filtration of Proteins Kit, which is commercially available from Life Sciences, can be used to separate dye-labeled peptides and proteins from free dye. The labeled biomolecules that remain after desalting can often be used successfully without further purification. In some cases, it may be necessary to resolve and assess the activity of the different products by means of HPLC or other chromatographic techniques.

Bioconjugate Compounds

In another embodiment of the invention, a bioconjugate of the Formula II is provided:

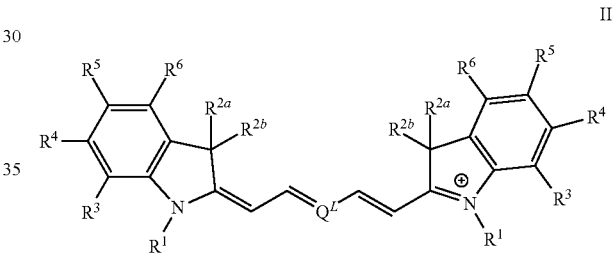

II wherein $Q^L$ is a three-polymethine-carbon segment:

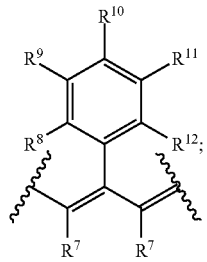

wherein the segment is the central portion of a seven-polymethine-carbon polymethine bridge.

$Q^L$, $R^1$, $R^{2a}$, $R^{2b}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, L, and Y are as previously defined for the compounds of Formulas I, Ia, and Ib respectively, including all preferred embodiments that are identified herein.

Each Z is independently selected from the group consisting of -L-$R^{13}$ and -L-$R^L$. In a more preferred aspect, Z is -L-$R^L$, wherein L is a bond.

In still another alternative preferred aspect, the Z group's L group is a bond, and $R^{13}$ or $R^L$ is connected directly to -L-Y— or directly bonded to the phenyl ring itself if L and Y are also bonds.

Each $R^L$ comprises 1) a linking group that connects the cyanine dye compound to a biomolecule; and 2) the biomolecule to which it is connected (i.e., the linking group and the biomolecule connected thereby), wherein the compound comprises at least one $R^L$. Preferred linking groups are indicated in Table 1 (column C). In a particularly preferred aspect, the linking group is an amide or an ester. In a more particularly preferred aspect, the linking group is an amide.

The compound has a balanced charge. In a preferred aspect, the compound's net anionic charge is balanced by alkali metal counterions (e.g., sodium or potassium). In a more preferred aspect, at least one of the counterions is sodium. Alternatively, all of the counterions are sodium.

In another preferred embodiment of the bioconjugate, any preferred embodiments or aspects of the inventive compound of Formulas I, Ia, or Ib can included in the embodiment of a bioconjugate. Representative examples of preferred compounds of Formulas I, Ia, or Ib that correspond to preferred bioconjugate embodiments are described in the dependent claims of the instant application.

In certain aspects, a preferred biomolecule for the instant invention is selected from the group containing an acyclo terminator triphosphate, an antibody, an antigen, an avidin, a carbohydrate, a deoxy nucleic acid, a dideoxy nucleotide triphosphate, an enzyme cofactor, an enzyme substrate, a fragment of DNA, a fragment of RNA, a hapten, a hormone, a nucleic acid, a nucleotide, a nucleotide triphosphate, a nucleotide phosphate, a nucleotide polyphosphate, an oligosaccharide, a peptide, PNA, a polysaccharide, a protein, a streptavidin, and the like.

Suitable nucleotides include nucleoside polyphosphates, including, but not limited to, deoxyribonucleoside polyphosphates, ribonucleoside polyphosphates, dideoxynucleoside polyphosphates, carbocyclic nucleoside polyphosphates and acyclic nucleoside polyphosphates and analogs thereof. Suitable nucleotides also include ucleotides containing 3, 4, 5, 6, or more phosphate groups, in the polyphosphate chain, where the phosphate (e.g., $\alpha$, $\beta$, $\gamma$, $\epsilon$, or terminal phosphate), sugar, base, or combination thereof is labeled with a compound of Formula I. The polyphosphate nuceotides include, but are not limited to, tetraphosphates, pentaphosphates, hexaphosphates, heptaphosphates, and the like. The bases include for example, purines, (adenine and guanine) pyrimidines, (thymine, uracil and cytosine) and derivatives thereof.

In certain instances, the dye of Formula I is attached to the phosphate (e.g. $\alpha$, $\beta$, $\gamma$, $\epsilon$-phosphate or terminal phosphate) through a phosphorothioate linkage (see, for example, U.S. Pat. No. 6,323,186, incorporated herein by reference), heteroatom, or functional group A, or B, resulting in linkage C of Table 1. See also U.S. Pat. No. 6,399,335 (incorporated herein by reference) entitled "$\gamma$-phosphoester nucleoside triphosphates," which provides methods and compositions for polymerizing particular nucleotides with a polymerase using $\gamma$-phosphoester linked nucleoside triphosphates. Other ways of linking the compounds of Formula I to a nucleotide are known to those of skill in the art. Using these nucleotides with a DNA polymerase can lead to identification of specific nucleotides in a DNA or RNA sequence by identification of the labeled pyrophosphate or polyphosphate released upon incorporation of the nucleotide base into RNA or DNA. (See for example, U.S. Pat. No. 6,232,075, US Pub. No. 2004/0241716 and U.S. Pat. No. 7,452,698 each of which is incorporated herein by reference).

More preferred aspects include an antibody, an avidin, and a streptavidin. Even more preferred aspects include a goat anti-mouse (GAM) antibody, a goat anti-rabbit (GAR) antibody, and streptavidin.

In certain other aspects, preferred biomolecules for the instant invention include somatostatin, endostatin, a carbohydrate, an oligosaccharide, an aptamer, a liposome, PEG, an angiopoietin, angiostatin, angiotensin II, $a_2$-antiplasmin, annexin V, $\beta$-cyclodextrin tetradecasulfate, endoglin, endosialin, endostatin, epidermal growth factor, fibrin, fibrinopeptide p, fibroblast growth factor, FGF-3, basic fibronectin, fumagillin, heparin, hepatocyle growth factor, hyaluronan, aninsulin-like growth factor, an interferon-$\alpha$, $\beta$ inhibitor, IL inhibitor, laminin, leukemia inhibitory factor, linomide, a metalloproteinase, a metalloproteinase inhibitor, an antibody, an antibody fragment, an acyclic RGD peptide, a cyclic RGD peptide, placental growth factor, placental proliferin-related protein, plasminogen, plasminogen activator, plasminogen activator inhibitor-1, a platelet activating factor antagonist, platelet-derived growth factor, a platelet-derived growth factor receptor, a platelet-derived growth factor receptor, platelet-derived endothelial cell growth factor, pleiotropin, proliferin, proliferin-related protein, a selectin, SPARC, a snake venom, substance P, suramin, a tissue inhibitor of a metalloproteinase, thalidomide, thrombin, thrombin-receptor-activating tetradecapeptide, transformin growth factor-$\alpha$, $\beta$, transforming growth factor receptor, tumor growth factor-$\alpha$, tumor necrosis factor, vitronectin, and the like.

In still other aspects, preferred biomolecules include a carbohydrate and a carbohydrate derivative. Representative examples include glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof. Even more preferred biomolecules include 2-deoxy-D-glucose, 2-deoxy-L-glucose, and racemic 2-deoxyglucose.

In yet still other aspects, the biomolecule can be a ligand that has affinity for a receptor selected from the group of EGFR, Her2, PDGFR, IGFR, c-Ryk, c-Kit, CD24, integrins, FGFR, KFGR, VEGFR, TRAIL decoy receptors, retinoid receptor, growth receptor, PPAR, vitamin receptor, glucocordicosteroid receptor, Retinoid-X receptor, RHAMM, high affinity folate receptors, Met receptor, estrogen receptor and Ki67.

Alternatively, the biomolecule is selected from the group of somatostatin, endostatin, a carbohydrate, a monosaccaride, a disaccharide, a trisaccharide, an oligosaccharide, aptamer, liposome and polyethylene glycol.

In yet another aspect, the biomolecule is a small-molecule drug or drug-like molecule such as a tetracycline antibiotic, a tetracycline derivative, and calcein.

Alternatively, the biomolecule is a small-molecule drug or peptide.

In other aspects, a cyanine dye set for the in the present invention is conjugated to a biological cell. Preferably, the dye is conjugated by means of an $R^L$ linking group.

In other aspects, a preferred biomolecule for the instant invention is selected from the group containing an antigen and a hapten. Preferably, the biomolecule is an immunogen.

In other aspects, a preferred biomolecule for the instant invention is selected from the group containing an enzyme cofactor and an enzyme substrate.

In other aspects, a preferred biomolecule for the instant invention is selected from the group containing an amino acid, a carbohydrate, a hapten, a hormone, a glycoprotein, a liposome, a nucleic acid, a nucleotide, a nucleotide triphosphate, a nucleotide polyphosphate, an oligosaccharide, a peptide, a peptide nucleic acid, a polyalkylene glycol, a polysaccharide, a protein, a small-molecule drug, and a snake venom.

More preferably, the preferred biomolecule is selected from the group containing angiostatin, endostatin, fumagillin, a fumagillin derivative, placental proliferin-related protein, plasminogen, somatostatin, and thalidomide.

Alternatively, the biomolecule is an aptamer.

Alternatively, the biomolecules is selected from the group containing an antibody and an antibody fragment.

Alternatively, the biomolecule is selected from the group containing polyethylene glycol.

Alternatively, the biomolecule is selected from the group containing an angiopoietin, epidermal growth factor, a fibroblast growth factor, hepatocyte growth factor, an insulin-like growth factor, placental growth factor, platelet-derived growth factor, a platelet-derived growth factor receptor, a platelet-derived endothelial cell growth factor, transforming growth factor-α, transforming growth factor-13, and transforming growth factor receptor. More preferably, the fibroblast growth factor is fibroblast growth factor 3.

Alternatively, the biomolecule is selected from the group containing an acyclic RGD peptide, a cyclic RGD peptide, and endosialin. Preferably, the biomolecule is an acyclic RGD peptide, a cyclic RGD peptide, or a derivative thereof. More preferably, the cyclic RGD peptide is cyclo (Arg-Gly-Asp-D-Phe-Lys) (i.e., c(RGDfK)).

Alternatively, the biomolecule is selected from the group containing $\alpha_2$-antiplasmin, plasminogen, plasminogen activator, plasminogen activator inhibitor-1, and plasminogen activator inhibitor-2.

Alternatively, the biomolecule is selected from the group containing fibrin, fibrinopeptide β, thrombin, and thrombin-receptor-activating tetradecapeptide.

Alternatively, the biomolecule is selected from the group containing an acyclo terminator triphosphate, a deoxynucleic acid, a ribonucleic acid, a a nucleotide, a nucleotide triphosphate, a nucleotide polyphosphate, and a peptide nucleic acid.

Alternatively, the biomolecule is selected from the group containing a fragment of RNA and a fragment of DNA.

Alternatively, the biomolecule is selected from the group containing angiotensin II and substance P.

Alternatively, the biomolecule is selected from the group containing a lectin and a selectin.

Alternatively, the biomolecule is selected from the group containing endoglin, a laminin, a fibronectin, SPARC, and vitronectin.

Alternatively, the biomolecule is selected from the group containing a metalloproteinase and a metalloproteinase inhibitor.

Alternatively, the biomolecule is a tissue inhibitor of a metalloproteinase.

Alternatively, the biomolecule is a platelet activating factor antagonist.

Alternatively, the biomolecule is selected from the group containing β-cyclodextrin tetradecasulfate, heparin, and hyaluronan.

Alternatively, the biomolecule is an annexin.

Alternatively, the biomolecule is selected from the group containing interleukin inhibitor, leukemia inhibitory factor, pleiotropin, and tumor necrosis factor. More preferably, the biomolecule is an interleukin-1 receptor antagonist.

Alternatively, the biomolecule is selected from the group containing proliferin and a proliferin-related protein.

Alternatively, the biomolecule is selected from the group containing calcein, laquinimod, linomide, and suramin.

Alternatively, the biomolecule is an interferon-α,β inhibitor.

Alternatively, the biomolecule is selected from the group containing tyramine and a tyramine derivative.

Alternatively, the biomolecule is selected from the group containing an avidin, biotin, and a streptavidin.

Alternatively, the biomolecule is selected from the group containing a glucosamine, a glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, and a derivative thereof. More preferably, the biomolecules include 2-deoxy-D-glucose, 2-deoxy-L-glucose, and racemic 2-deoxyglucose.

Methods of Imaging

In another embodiment, the compounds of Formula I, Ia, or Ib can be used as in vitro or in vivo optical imaging agents of tissues and organs in various biomedical applications. In one embodiment, the present invention provides a method for imaging, the method comprising administering a compound of Formula I, Ia, or Ib.

In certain preferred aspects of the invention, any of the embodiments or aspects of the inventive compound of Formula I, Ia, or Ib that are described herein can be used in the method of imaging. Representative examples of preferred compounds for use in the method are described in the specification and the dependent claims of the instant application.

In another embodiment, the present invention provides a method for imaging, the method comprising administering a compound of Formula II, IIa, or lib.

In certain preferred aspects of the invention, any of the embodiments or aspects of the inventive compound of Formula II that are described herein can be used in the method of imaging. Representative examples of preferred compounds for use in the method are described in the specification and the dependent claims of the instant application.

In certain preferred aspects, the compounds of the present invention are used as in vivo imaging agents of tissues and organs in various biomedical applications including, but not limited to, tomographic imaging of organs, monitoring of organ functions, coronary angiography, fluorescence endoscopy, imaging of tumors, laser guided surgery, photoacoustic and sonofluorescence methods, and the like. In one aspect, the compounds of the invention are useful for the detection of the presence of tumors and other abnormalities by monitoring the blood clearance profile of the dyes. In another aspect of the invention, the compounds are useful for laser assisted guided surgery for the detection of micro-metastases of tumors upon laparoscopy. In yet another aspect, the compounds are useful in the diagnosis of atherosclerotic plaques and blood clots.

In further aspects, the compounds of the present invention are used in the imaging of: (1) ocular diseases in ophthalmology, for example, to enhance visualization of chorioretinal diseases, such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; (5) breast tumors via 2D- or 3D-image reconstruction; and (6) brain tumors, perfusion, and stroke via 2D- or 3D-image reconstruction.

In certain aspects, the compounds of the invention that are bioconjugates are particularly useful for imaging tumors, tissues, and organs in a subject. For example, the existence of cancer cells or cancer tissues can be verified by labeling an anti-tumor antibody with a compound of Formula I and then administering the bioconjugated antibody to the subject for detection and imaging of the tumor. Conjugates between the dye compound and other antibodies, peptides, polypeptides, proteins, ligands for cell surface receptors, small molecules, and the like are also useful agents for the in vivo imaging of tumors, tissues, and organs in a subject.

In certain aspects, the compounds of the invention may be administered either systemically or locally to the organ or tissue to be imaged, prior to the imaging procedure. In one aspect, the compounds are administered intravenously. In another aspect, the compounds are administered parenterally. In yet another aspect, the compounds are administered enterally. The compositions used for administration of the compound typically contain an effective amount of the compound or conjugate along with conventional pharmaceutical carriers and excipients appropriate for the type of administration contemplated. For example, parenteral formulations advantageously contain a sterile aqueous solution or suspension of a compound of Formula I, Ia, or Ib; or a bioconjugate of Formula II, IIa, or IIb. Compositions for enteral administration typically contain an effective amount of the compound or bioconjugate in aqueous solution or suspension that may optionally include buffers, surfactants, thixotropic agents, flavoring agents, and the like.

In certain aspects, the compositions are administered in doses effective to achieve the desired optical image of a tumor, tissue, or organ. Such doses may vary widely, depending upon the particular compound or bioconjugate employed, the tumor, tissue, or organ subjected to the imaging procedure, the imaging equipment being used, and the like.

In certain aspects, the method of the present invention provides for administering to the subject a therapeutically effective amount of a compound; a targeting agent, such as a bioconjugate; or mixtures thereof. In one aspect, the targeting agent selectively binds to the target tissue. Light at a wavelength or waveband corresponding to that which is absorbed by the photosensitizing agent is then administered. In another aspect, the compounds of the present invention act agents capable of binding to one or more types of target cells or tissues, when exposed to light of an appropriate waveband, absorb the light, causing substances to be produced that illuminate, impair or destroy the target cells or tissues. Preferably, the compound is nontoxic to the subject to which it is administered or is capable of being formulated in a nontoxic composition that can be administered to the subject. In addition, following exposure to light, the compound in any resulting photodegraded form is also preferably nontoxic.

In yet another aspect, the compounds of the present invention are administered by any means known in the art, including, but not limited to, ingestion, injection, transcutaneous administration, transdermal administration, and the like. Preferably, the compounds are administered transcutaneously to a subject.

In certain aspects, during imaging, the light passes through unbroken tissue. Where the tissue layer is skin or dermis, such transcutaneous imaging includes transdermal imaging, and it will be understood that the light source is external to the outer skin layer. In some aspects (i.e., transillumination), the light passes through a tissue layer, such as the outer surface layer of an organ (e.g., the liver). In such cases, the light source is preferably external to the organ, but internal or implanted within the subject or patient.

In further aspects of the invention, the target tumor, tissue, or organ for treatment is selected from the group of vascular endothelial tissue, an abnormal vascular wall of a tumor, a solid tumor, a tumor of the head, a tumor of the neck, a tumor of a the gastrointestinal tract, a tumor of the liver, a tumor of the breast, a tumor of the prostate, a tumor of the ovary, a tumor of the uterus, a tumor of the testicle, a tumor of the lung, a nonsolid tumor, malignant cells of one of a hematopoietic tissue and a lymphoid tissue, lesions in the vascular system, a diseased bone marrow, neuronal tissue or diseased neuronal tissue, and diseased cells in which the disease is one of an autoimmune and an inflammatory disease. In yet a further aspect, the target tissue is a lesion in the vascular system of a type selected from the group of atherosclerotic lesions, arteriovenous malformations, aneurysms, and venous lesions.

In still further aspects, the forms of energy include, but are not limited to, light (i.e., radiation), thermal, sonic, ultrasonic, chemical, light, microwave, ionizing (such as x-ray and gamma ray), mechanical, and electrical. The term "radiation" as used herein includes all wavelengths and wavebands. Preferably, the radiation wavelength or waveband is selected to correspond with or at least overlap the wavelengths or wavebands that excite the photosensitizing agent. Compounds of the instant invention typically have one or more absorption wavebands that excite them to produce the substances which illuminate, damage or destroy target cells, tissues, organs, or tumors. Preferably, the radiation wavelength or waveband matches the excitation wavelength or waveband of the photosensitizing agent and has low absorption by the non-target cells and the rest of the subject, including blood proteins. More preferably, the radiation wavelength or waveband is within the NIR range of about 600 nm to about 1000 nm or a related range thereof (e.g., the ranges that are described in the instant claims).

In certain aspects, the compounds of the present invention are used to directly stain or label a sample so that the sample can be identified or quantitated. For instance, such compounds can be added as part of an assay for a biological target analyte, as a detectable tracer element in a biological or non-biological fluid; or for such purposes as photodynamic therapy of tumors, in which a dyed sample is irradiated to selectively destroy tumor cells and tissues; or to photoablate arterial plaque or cells, usually through the photosensitized production of singlet oxygen.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable optical response as used herein includes a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic. Some compounds of the invention may exhibit little fluorescence emission, but are still useful as chromophoric dyes. Such chromophores are useful as energy donors in fluorescence (or Förster) resonance energy transfer (FRET) applications, or to impart the desired color to a sample or portion of a sample.

FRET is a process by which a donor molecule (e.g., a dye) absorbs light, entering an excited state. Rather than emitting light, the first molecule transfers its excited state to an acceptor molecule with other properties (e.g., a dye fluorescing at a different wavelength or a quencher), and the acceptor fluoresces or quenches the excitation. Because the efficiency of the transfer is dependant on the two molecules' proximity, it can indicate information about molecular complex formation or biomolecular structure. It can also indicate where a particular complex is located within a cell or organism (e.g., FRET optical microscopy). For ways to use similar dyes as acceptors (quenchers) in FRET processes, see X. Peng, H. Chen, D. R. Draney, W. Volcheck, A. Schultz-Geschwender, and D. M. Olive, "A nonfluorescent, broad-range quencher dye for Förster resonance energy transfer assays," *Anal. Biochem* 2009, 388(2): 220-228.

In certain aspects, a suitable FRET acceptor is disclosed as in WO 2007/005222, which is incorporated herein by reference. The compounds include the following essentially non-fluorescent cyanine dyes of formula III:

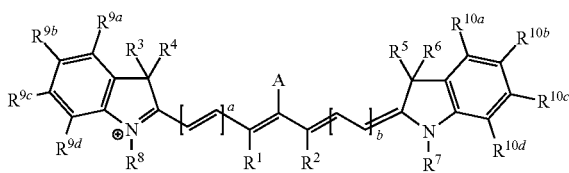

III wherein the substituents in formula III are defined as follows: $R^1$ and $R^2$ are each independently selected from the group consisting of hydrogen and optionally substituted $(C_1$-$C_6)$ alkyl. Alternatively, $R^1$ and $R^2$ together with the

group to which they are bonded form a 5- to 7-membered ring, the ring being optionally substituted with 1 to 4 substituents selected from the group consisting of halogen, cyano, sulfonate, $(C_1$-$C_8)$haloalkyl, hydroxy, $(C_1$-$C_6)$alkoxy and optionally substituted $(C_1$-$C_8)$alkyl.

In Formula III, $R^3$ and $R^4$ are each independently an optionally substituted $(C_1$-$C_6)$alkyl, and may optionally join together with the atoms to which they are attached to form a 5- to 7-membered carbocyclic ring; or alternatively, the substituents $R^3$ and $R^4$ are replaced with the group

wherein B is $(C_1$-$C_6)$alkyl; or B and $R^{9a}$ together with the carbon atoms to which they are attached join to form a 5- or 6-membered ring optionally having 1 or 2 heteroatoms and optionally having up to 3 double bonds.

In Formula III, the substituents $R^5$ and $R^6$ are each independently an optionally substituted $(C_1$-$C_6)$alkyl, and may optionally join together with the atom to which they are attached to form a ring.

In Formula III, the substituents $R^7$ and $R^8$ are each independently selected from the group consisting of optionally substituted $(C_1$-$C_6)$alkyl, optionally substituted aryl$(C_1$-$C_6)$ alkyl, optionally substituted heteroaryl$(C_1$-$C_6)$alkyl, —$(CH_2)_cR^{13}$ and —$(CH_2)_dR^{15}$. Indices c and d are each independently an integer from 1-50. $R^{13}$ is a functional group that does not directly react with a carboxyl, hydroxyl, amino or thio group on a biomolecule. $R^{15}$ is a linking group selected from the group consisting of mercapto, amino, haloalkyl, phosphoramidityl, N-hydroxy succinimidyl ester, sulfo N-hydroxysuccinimidyl ester, isothiocyanato, iodoacetamidyl, maleimidyl and an activated carboxylic acid.

In Formula III, the substituents $R^{9a\text{-}9d}$ and $R^{10a\text{-}10d}$ are each independently selected from the group consisting of hydrogen, optionally substituted $(C_1$-$C_6)$alkyl, —$SO_3Cat^+$, halogen, —$C(O)OR^{11}$, —$C(O)NR^{11}R^{12}$, —$C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$(CH_2)_dR^{15}$, —$S(O)_2NR^{12}(CH_2)_dR^{15}$, —$R^{15}$ and —$NR^{20}R^{21}$, wherein $Cat^+$ is a cation. The substituents $R^{11}$ and $R^{12}$ are each independently selected from the group consisting of hydrogen and $(C_1$-$C_6)$alkyl; $R^{20}$ and $R^{21}$ are each independently selected from the group consisting of hydrogen, optionally substituted $(C_1$-$C_8)$alkyl, $CatO_3S(C_1$-$C_{50})$alkylene.

In Formula III, alternatively, any two substituents of $R^{10a\text{-}10d}$ located on adjacent atoms, together with the atoms to which they are attached, join to form a 5- or 6-membered ring optionally having 1 or 2 heteroatoms and optionally having up to 3 double bonds; wherein the ring may be further substituted with 1 to 3 substituents selected from the group consisting of optionally substituted $(C_1$-$C_6)$alkyl, —$SO_3^-Cat$, halogen, —$C(O)OR^{11}$, —$C(O)NR^{11}R^{12}$, $C(O)O(CH_2)_dR^{15}$, —$C(O)NR^{11}(CH_2)_dR^{15}$, —$NR^{12}C(O)O(CH_2)_dR^{15}$, —$NR^{12}C(O)OR^{11}$, —$S(O)_2NR^{12}(CH_2)_dR^{15}$, —$R^{15}$ and —$NR^{20}R^{21}$ In Formula III, the variable a is an integer from 0-3 and the variable b is an integer from 0-2. A is selected from the group consisting of hydrogen, halogen, cyano, optionally substituted $(C_1$-$C_8)$alkyl, optionally substituted $(C_1$-$C_6)$dialkylamino, optionally substituted alkylthio, —$(CH_2)_dR^{15}$, —$R^{15}$, optionally substituted $(C_1$-$C_6)$heteroalkyl, phenoxy and an optionally substituted aryloxy group having the formula

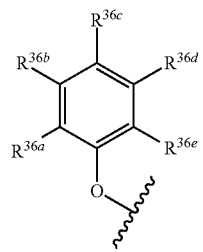

wherein $R^{36a}$—$R^{36e}$ are each independently selected from the group consisting of hydrogen, —$SO_3Cat^+$, —$(CH_2)_dR^{15}$, —$C(O)O(CH_2)_dR^{15}$, —$C(O)NR^{11}(CH_2)_dR^{15}$, —$NR^{12}C(O)$ $O(CH_2)_dR^{15}$, —$S(O)_2NR^{12}(CH_2)_dR^{15}$, —$R^{15}$, $(C_1$-$C_6)$alkyl, carboxyl and $NR^{20}R^{21}$.

The compounds of Formula III have at least one linking group. In certain aspects, the compounds of the invention have one or more linking groups such as for example, 1, 2, 3 or more linking groups. The at least one linking group $R^{15}$ can be attached at various positions on the compound of Formula III.

In certain aspects, for biological applications, the compounds of the invention are typically used in an aqueous, mostly aqueous or aqueous-miscible solution prepared according to methods generally known in the art. The exact concentration of compound is dependent upon the experimental conditions and the desired results, but ranges of 0.00001 mM up to 0.1 mM, such as about 0.001 mM to about 0.01 mM, are possible. The optimal concentration is determined by systematic variation until satisfactory results with minimal background fluorescence is accomplished.

In certain aspects, the method may involve treatment of an animal or sample with a dose comprising a compound of Formula I, a bioconjugate of Formula II, a bioconjugate of Formula III, or any of the aspects or embodiments thereof. The exact concentration of compound is dependent upon the subject and the desired results. In certain embodiments, a dose of at least about 0.001, 0.005, 0.01, 0.025, 0.05, or 0.075 mg/kg is used. Alternatively, a dose of at most about 0.001, 0.005, 0.01, 0.025, 0.05, or 0.075 mg/kg is used. In certain other embodiments, a dose of at least about 0.1, 0.25, 0.5, or 0.75 mg/kg is used. Alternatively, a dose of at most about 0.1, 0.25, 0.5, or 0.75 mg/kg is used. In still other embodiments, a dose of at least about 0.1, 0.25, 0.5, or 0.75 mg/kg is used. Alternatively, a dose of at most about 0.1, 0.25, 0.5, or 0.75 mg/kg is used. In yet still other embodiments, a dose of at least about 1, 2.5, 5, or 7.5 mg/kg is used. Alternatively, a dose of at most about 1, 2.5, 5, or 7.5 mg/kg is used. In additional other embodiments, a dose of at least about 10, 25, 50, or 75 mg/kg is used. Alternatively, a dose of at most about 10, 25, 50, or 75 mg/kg is used. In additional still other embodiments, a dose of at least about 100, 250, 500, or 750 mg/kg is used. Alternatively, a dose of at most about 100, 250, 500, or 750 mg/kg is used. Other amounts for administration of an effective dose may be readily determined by one of skill in the art.

In certain aspects, the compounds are most advantageously used to stain samples with biological components. The sample can comprise heterogeneous mixtures of components (e.g., mixtures including intact cells, fixed cells, cell extracts, bacteria, viruses, organelles, and combinations thereof), or a single component or homogeneous group of components (e.g. natural or synthetic amino acid, nucleic acid or carbohydrate polymers, or lipid membrane complexes). Within the concentrations of use, these compounds are generally non-toxic to living cells and other biological components.

The compound is combined with the sample in any way that facilitates contact between the compound and the sample components of interest. Typically, the compound or a solution containing the compound is simply added to the sample. Certain compounds of the invention, particularly those that are substituted by one or more sulfonic acid moieties, tend to be impermeant to membranes of biological cells, and once inside viable cells are typically well retained. Treatments that permeabilize the plasma membrane, such as electroporation, shock treatments or high extracellular ATP, can be used to introduce selected compounds into cells. Alternatively, selected dye compounds can be physically inserted into cells, e.g., by pressure microinjection, scrape loading, patch clamp methods, or phagocytosis.

Alternatively, dye compounds can be conjugated to a biomolecule that increases their uptake into cells (e.g., cell-penetrating peptides such as Tat, penetratin, transportin, derivatives thereof (e.g., Tat derivatives incorporating β- and γ-amino acids), and the like). This general approach is usable in vitro or in vivo.

In certain aspects, at any time after or during staining, the sample is illuminated with a wavelength of light selected to give a detectable optical response, and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred aspects of the invention are compounds that are excitable at or near the wavelengths 674-685 nm, 685-690 nm, 690-695 nm, 690-700 nm, 700-720 nm, 720-740 nm, 740-750 nm, 750-760 nm, 760-770 nm, 770-780 nm, 780 nm, 780-790 nm, 790-800 nm, 800-810 nm, 810 nm, 810-820 nm, 820-830 nm, and beyond (e.g., 850 nm), as these regions closely match the output of exemplary compounds or of relatively inexpensive excitation sources.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined by means of a flow cytometer, examination of the sample optionally includes sorting portions of the sample according to their fluorescence response.

EXAMPLES

Below, the present invention will be described by way of examples, which are provided for illustrative purposes only. Accordingly, they are not to be construed as limiting the scope of the present invention as defined by the appended claims.

Example 1

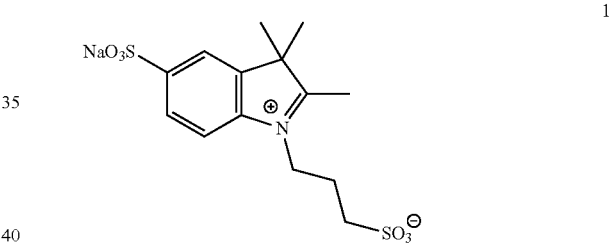

A mixture of 14 g of sodium 2,3,3-trimethyl-3H-indole-5-sulfonate and 14 g 1,3-propanesultone in 100 mL dicholorobenzene was heated at 110° C. for 2 h. After it cooled, the solvent was decanted. The solid was then dissolved in 100 ml of acetonitrile, and 300 ml of ethyl acetate was added. The resulting sticky solid was again stirred in 300 ml of ethyl acetate to yield 20 g of the compound 1.

Example 2

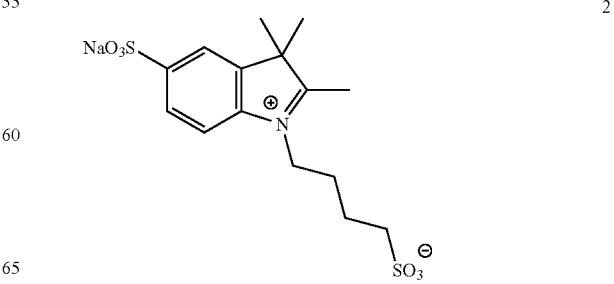

Compound 2 was prepared analogously to compound 1 except with 1,4-butanesultone as a starting material.

Example 3

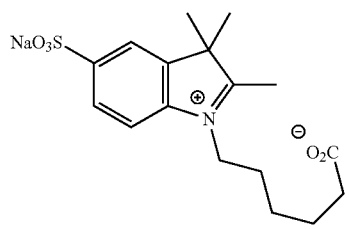

3

A mixture of 0.54 g of sodium 2,3,3-trimethyl-3H-indole-5-sulfonate and 1.32 g of 6-bromohexanoic acid was heated at 120° C. for 1 h. Ethyl acetate (10 mL) was added, and the reaction mixture was heated at reflux for 15 minutes, then cooled to room temperature. The supernatant liquid was decanted to yield the product 3.

Example 4

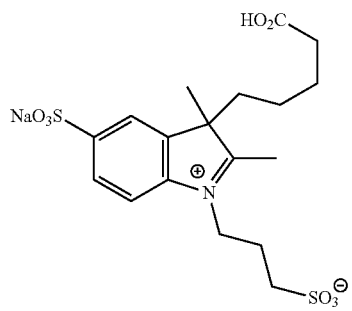

4

Compound 4 is prepared analogously to compound 1 except with sodium 3-(4-carboxybutyl)-2,3-dimethyl-3H-indole-5-sulfonate as a starting material. See also the procedure of U.S. Pat. Publ. No. 2007/0232805.

Example 5

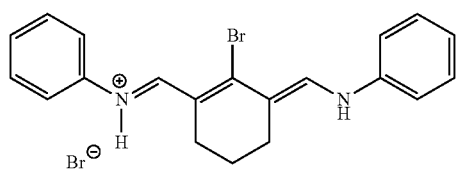

5

A solution dimethylformamide (20 ml) in 40 ml of methylene chloride is stirred for 45 min with phosphorus bromide (10 ml) at 4 to 5° C. Subsequently, the mixture is stirred at 5° C. for another 30 min. Cyclohexanone (10 g) is added dropwise for approximately 15 min causing the temperature to boil. After heating at reflux for 5 h, methylene chloride is distilled off to 45° C. (internal temperature), and subsequently the remaining volatile components are removed in vacuo. The residue iss discharged on 0.5 kg of ice with constant cooling at 20° C. An anline/EtOH [1:1, (v/v), 20 ml] is added dropwise. Reaction was continued for additional 30 min after the aniline addition, and then the yellow mixture is poured into ice-cold water/conc. HCl (10:1, 11 ml). The final malonaldehyde dianil hydrochloride salts are precipitated as light yellow solids.

The chloro-analog to bromo-compound 5 is commercially available and serves as an alternative substrate to compound 5.

Example 6

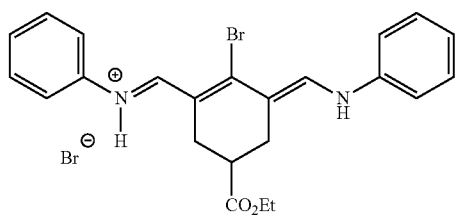

6

The procedure to synthesize compound 6 was analogous to Example 5 above except that 4-cyclohexanone carboxylic acid ethyl ester was a starting material.

Example 7

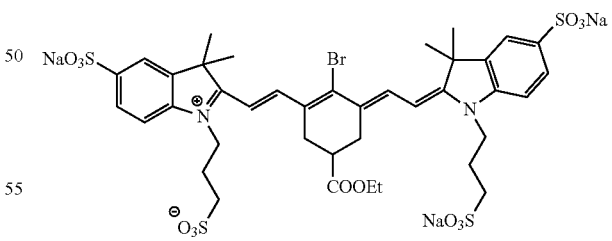

7

To a solution of compound 1 (2.0 equiv) and compound 6 (1.0 equiv) in ethyl alcohol (20 ml) was added sodium acetate (4.0 equiv). The mixture was heated at 50° C. for 2 h. Diethyl ethyl ether was added to precipitate the crude product, which was purified by chromatography (15% methanol/water) on RP—C18 silica gel. UV: $\lambda_{MeOH}$=788 nm The chloro analog was synthesized by an analogous procedure from the chloro equivalent for compound 6.

Example 8

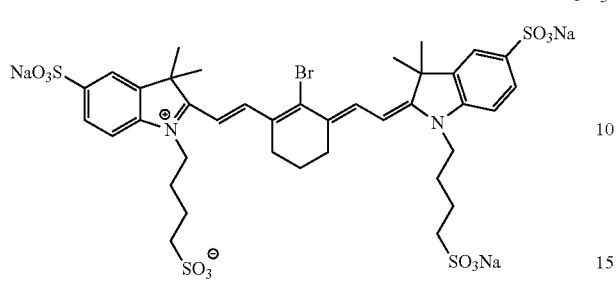

The procedure to synthesize compound 8 is analogous to Example 7 above except that compound 2 (2.0 equiv) and compound 5 are starting materials.

The chloro analog was synthesized by an analogous procedure from the commercially available chloro equivalent for compound 5.

Example 9

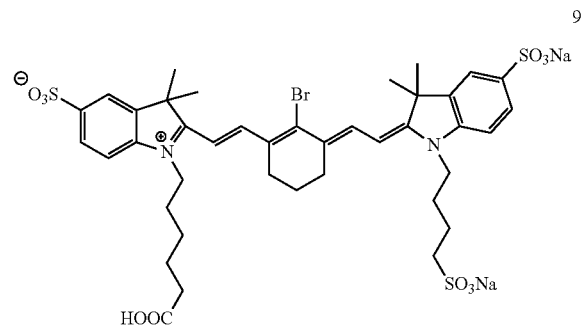

To compound 2 (1.0 equiv), compound 3 (2.0 equiv), and compound 5 (1.0 equiv) in ethyl alcohol (20 ml) is added sodium acetate (4.0 equiv). The mixture is heated at 50° C. for 2 h. Diethyl ethyl ether is added to precipitate the crude product, which is purified by chromatography (15% acetonitrile/water) on RP—C18 silica gel. UV: $\lambda_{MeOH}$=788 nm

Example 10

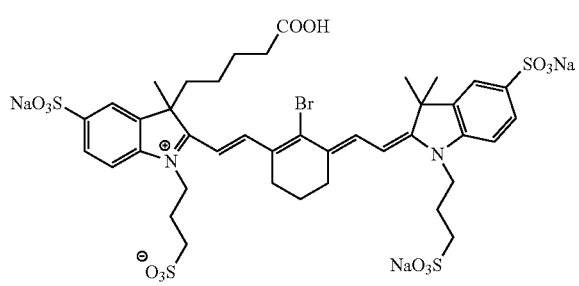

The procedure to synthesize compound 10 is analogous to Example 9 above except that compound 4 (2.0 equiv) is a starting material.

The chloro-equivalent to bromo-compound 10 is prepared by a similar procedure using the chloro analog to compound 5.

Example 11

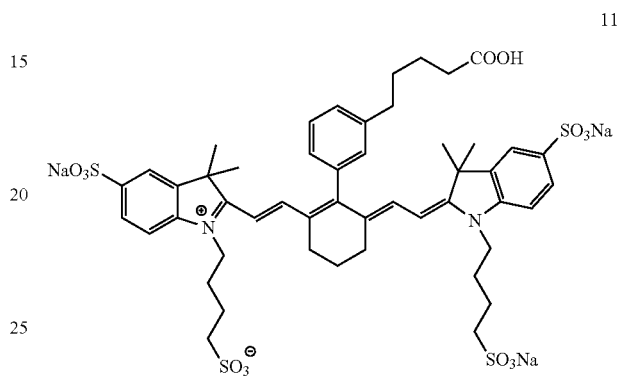

Compound 11 was prepared by combining 100 mg of the bromo dye (compound 8) with 70 mg 5-(3-boronophenyl) pentanoic acid and 10 mg of Pd(PPh$_3$)$_4$. The mixture was heated at reflux with 50 mL water for 1 h under nitrogen gas. The green solution was separated by HPLC using a reverse-phase C18 acetonitrile/water gradient in a ratio of 15:85.

Alternatively, compound 11 was prepared by the same general procedure using the chloro-analog to compound 8 as a starting material. The purified product had a $\lambda_{MeOH}$=767 nm, $\lambda_{PBS}$=757 nm, and emission at 775 nm. Its absorption and emission spectra in PBS are shown in FIG. 1.

Example 12

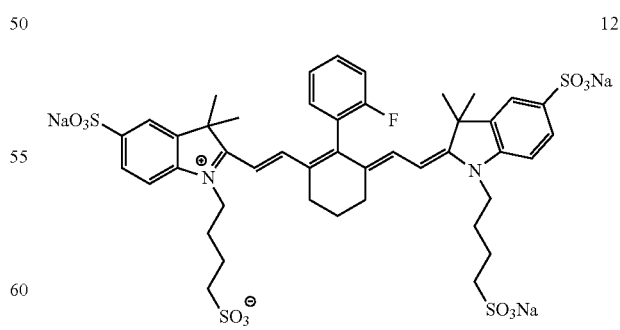

Compound 12 was prepared analogously to compound 11 (Example 11), except that 2-fluorophenylboronic acid and the chloro-analog to compound 8 were used as starting materials. UV: $\lambda_{MeOH}$=772 nm.

Example 13

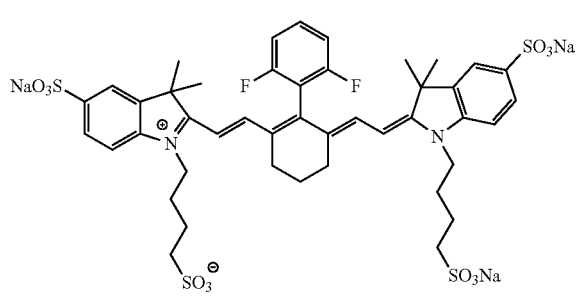

13

Compound 13 was prepared analogously to compound 11 (Example 11), except that 2,6-difluorophenylboronic acid and the chloro-analog to compound 8 were used as starting materials. UV: $\lambda_{MeOH}$=782 nm.

Example 14

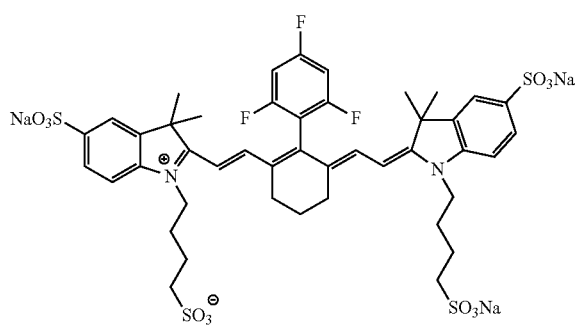

14

Compound 14 was prepared analogously to compound 11 (Example 11), except that 2,6-difluorophenylboronic acid and the chloro-analog to compound 8 were used as starting materials. UV: $\lambda_{MeOH}$=785 nm.

Example 15

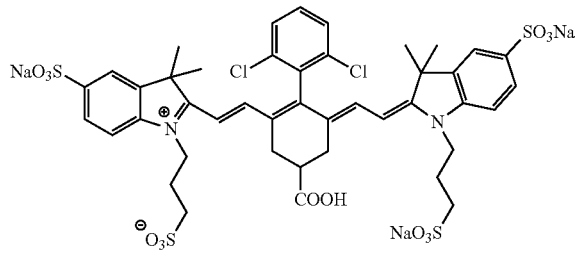

15

Compound 15 was prepared by combining 100 mg of the bromo dye (compound 7) with 70 mg 2,6-dichloro phenylboronic acid and 10 mg of Pd(PPh$_3$)$_4$. The mixture was refluxed with 50 ml water for 2 h under nitrogen gas. Then 10% aqueous sulfuric acid is added, and the mixture is heated at reflux for 1 h. The resulting green solution was separated by HPLC using a reverse-phase C18 acetonitrile/water gradient in a ratio of 15:85. The purified product has $\lambda_{MeOH}$=782 nm.

Example 16

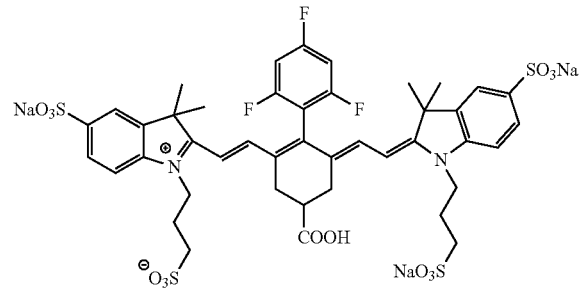

16

Compound 16 was prepared analogously to compound 15 (Example 15), except that 2,4,6-trifluoro phenylboronic acid was used as a starting material. UV: $\lambda_{MeOH}$=785 nm.

Figure 2:
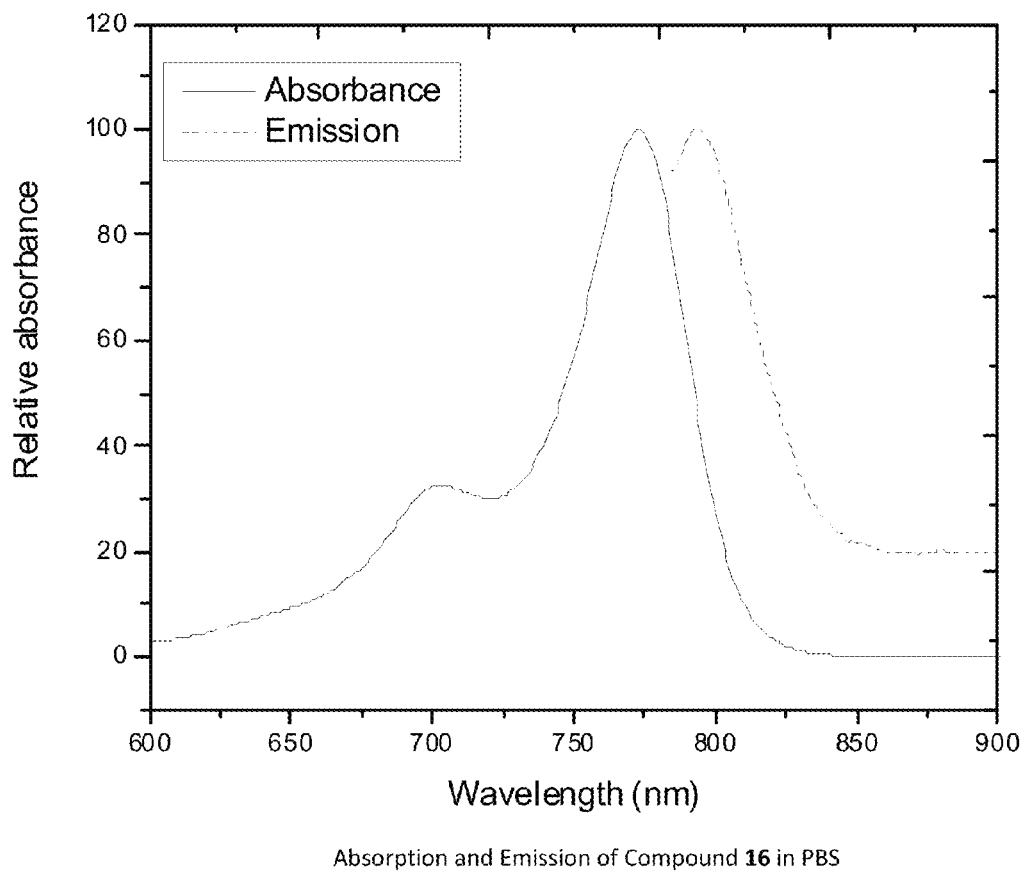
FIG. 2 shows the absorbance and emission spectra of compound 16 (Example 16) in PBS. For emission, the y-axis indicates the dye's fluorescence as expressed in arbitrary units.

Compound 16 was also prepared by the same general procedure using the chloro-analog to compound 7 as a starting material. The purified product's absorption and emission spectra in PBS are shown in FIG. 2.

Example 17

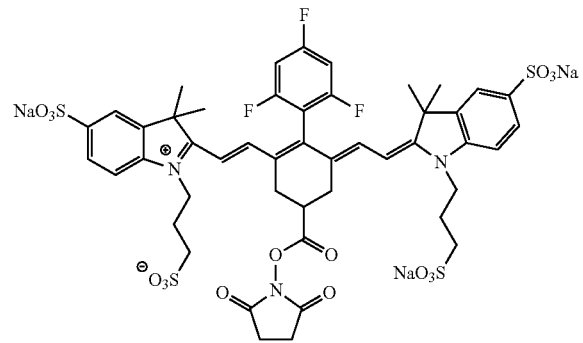

17

To 55 mg of compound 16 in 1 mL of DMSO was added 34 μl of triethylamine and 21 mg of N,N'-disuccinimidyl carbonate. The mixture was stirred at room temperature for 30 min and then precipitated by diethyl ethyl ether to yield the succinimidyl ester 17 as a green solid.

Example 18

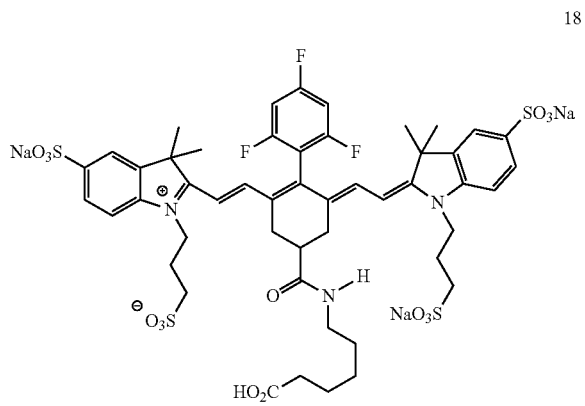

5-Aminopentanoic acid (M.W. 117, 10 mg) and compound 17 (20 mg) are mixed in 50 mM phosphate buffer (10 ml, pH 8.5) for 1 h. The mixture is purified by preparative HPLC to afford compound 18

Example 19

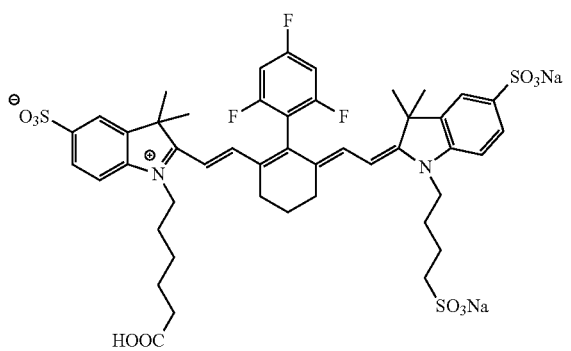

Compound 19 was prepared analogously to compound 16 (Example 16), except that compound 9 was used as a starting material rather than compound 7. UV: $\lambda_{MeOH}$=785 nm.

Example 20

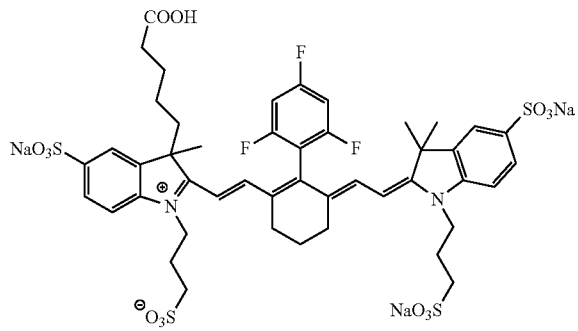

Compound 20 is prepared analogously to compound 16 (Example 16), except that compound 10 is used as a starting material. UV: $\lambda_{MeOH}$=785 nm.

Example 21

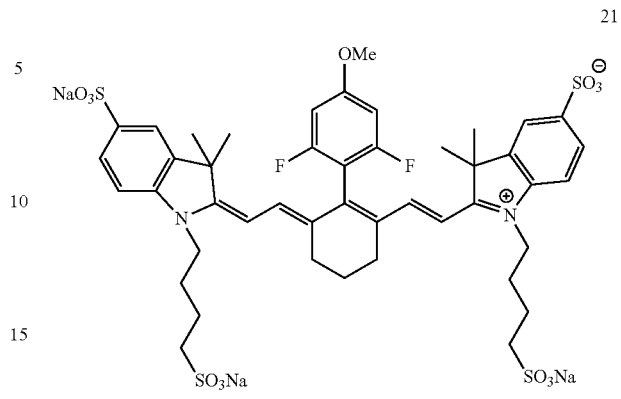

Compound 21 was prepared analogously to compound 11 (Example 11), except that the chloro-analog to compound 8 and 2,6-difluoro-4-methoxy phenylboronic acid were used as starting materials. UV: $\lambda_{MeOH}$=772 nm.

Example 22

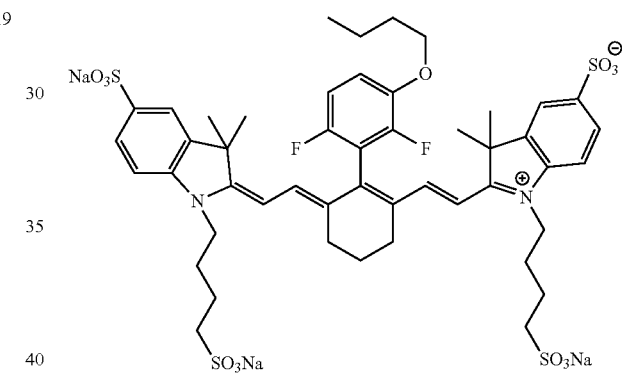

Compound 22 was prepared analogously to compound 11 (Example 11), except that the chloro-analog to compound 8 and 2,6-difluoro-4-butoxy phenylboronic acid were used as starting materials. UV: $\lambda_{MeOH}$=786 nm, $\lambda_{PBS}$=779 nm.

Example 23

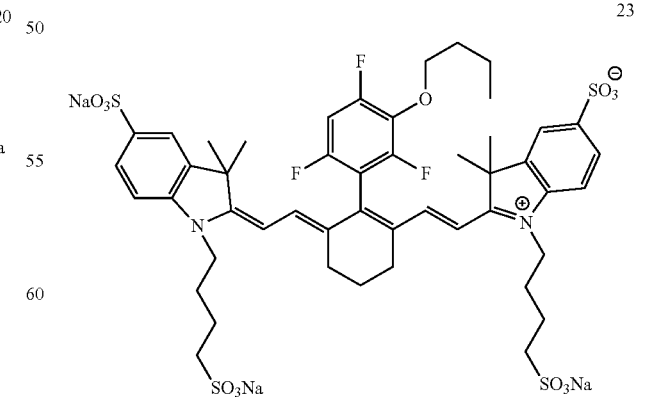

Compound 23 was prepared analogously to compound 11 (Example 11), except that the chloro-analog to compound 8 and 2,4,6-trifluoro-3-butoxy phenylboronic acid were used as starting materials. UV: $\lambda_{MeOH}$=789 nm, $\lambda_{PBS}$=782 nm; .emission at 806 nm: $E_{MeOH}$=300,000, $E_{PBS}$=240,000.

Example 24

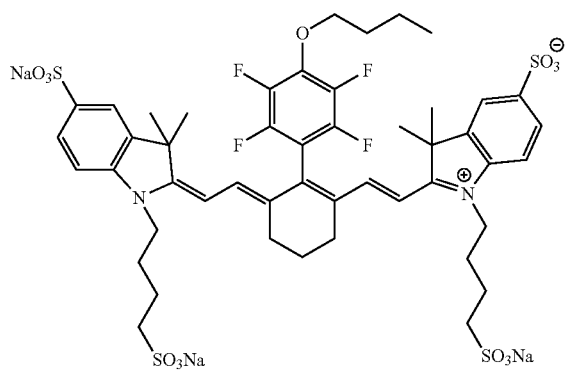

Compound 24 is prepared analogously to compound 11 (Example 11), except that the chloro-analog to compound 8 and 2,3,5,6-tetrafluoro-4-butoxy phenylboronic acid were used as starting materials. UV: $\lambda_{MeOH}$=790 nm, $\lambda_{PBS}$=786 nm; emission at 805 nm.

Example 25

Example 25 illustrates the synthesis of a fluorescence-quenching dye sodium 6-((E)-2-((E)-2-(3-((E)-2-(5-(bis(3-sulfonatopropyl)amino)-3,3-dimethyl-1-(3-sulfonatopropyl)-3H-indolium-2-yl)vinyl)-2-(2-fluorophenyl)cyclohex-2-enylidene)ethylidene)-1,1-dimethyl-7-sulfonato-1H-benzo[e]indol-3(2H)-yl)hexanoate (25a).

Compound 25a was prepared by combining 50 mg of IRDye® QC-1 Carboxylate (25b, LI-COR Biosciences), 9.8 mg of 2-fluorophenylboronic acid, 4.0 mg of Pd(PPh$_3$)$_4$ 16.4 mg of sodium acetate, 200 μL of 2-methoxyethanol, and 2 mL of water. The mixture was heated at reflux for 1.5 hours under a nitrogen atmosphere. The compound was purified by reverse-phase C18 chromatography using acetonitrile/water yielding 50 mg of a blue-green solid (product 25a). Absorbance: $\lambda_{Water}$=785 nm, $\lambda_{MeOH}$=777 nm.

Example 26

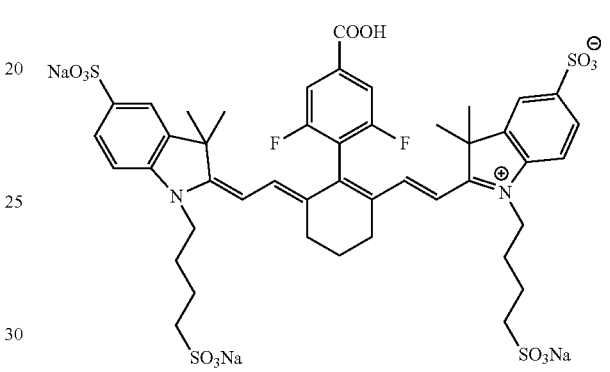

Compound 26 was prepared by combining 100 mg of the bromo dye (compound 8) with 70 mg of 2,6-difluoro-4-(methoxycarbonyl)phenylboronic acid pinacol ester and 10 mg of Pd(PPh$_3$)$_4$. The mixture was heated at reflux with 100 ml water for 2 h under nitrogen gas. Then 2 ml 10% aqueous sulfuric acid was added, and the mixture was refluxed for 1 h. The resulting green solution was separated by HPLC using a reverse-phase C18 acetonitrile/water gradient in a ratio of 15:85. $\lambda_{MeOH}$=782 nm.

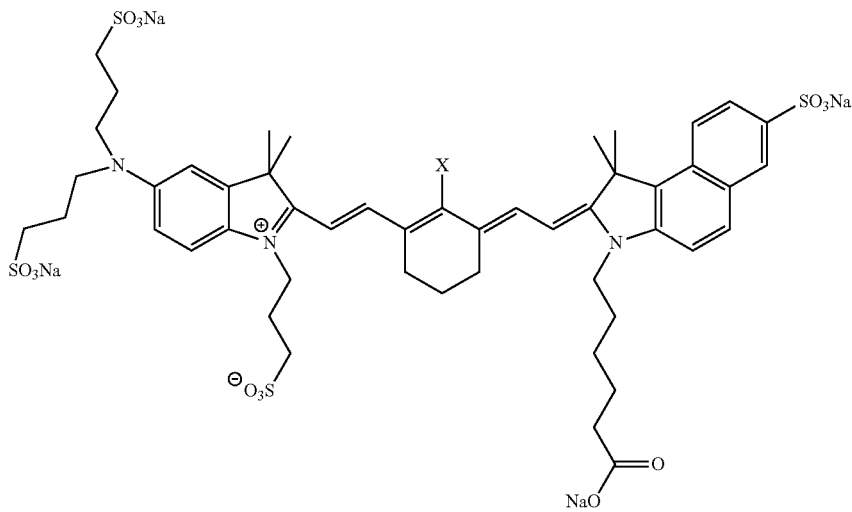

25a X = 2-fluorophenyl
25b X = Cl

Example 27

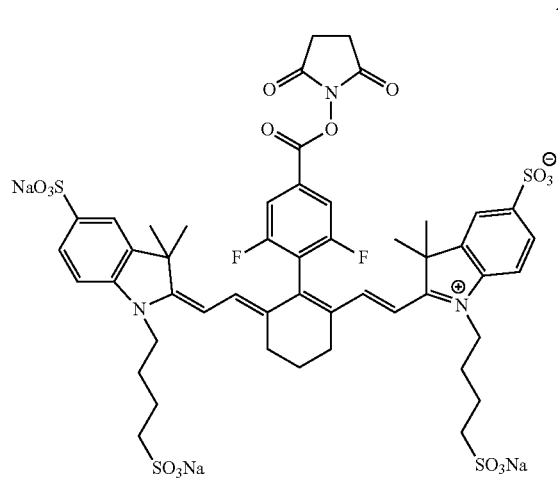

Compound 27 is prepared analogously to compound 17 (Example 17), except that compound 26 is used as a starting material.

Example 28

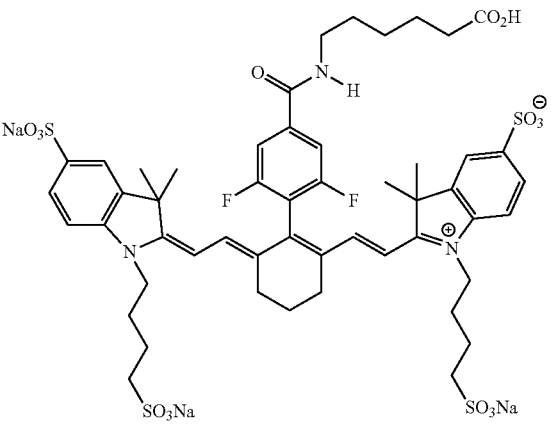

Compound 28 was prepared analogously to compound 18 (Example 18), except that compound 27 was used as a starting material. UV: $\lambda_{MeOH}$=782 nm.

Example 29

TABLE 2

Halo Substitution Effect on Absorption Wavelength of the Cyanine Dye

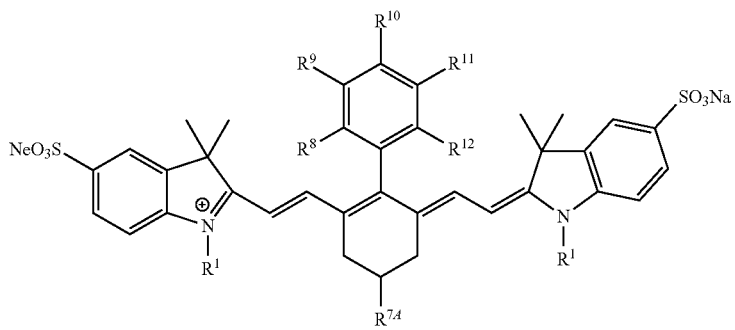

| Compound | $R^1$ | $R^{7A}$ | $R^8$ | $R^9$ | $R^{10}$ | $R^{11}$ | $R^{12}$ | $\lambda_{MeOH}$ |
|---|---|---|---|---|---|---|---|---|
| 11 | $(CH_2)_4SO_3Na$ | H | H | H | H | $(CH_2)_4COOH$ | H | 766 |
| 12 | $(CH_2)_4SO_3Na$ | H | H | H | H | H | F | 772 |
| 13 | $(CH_2)_4SO_3Na$ | H | F | H | H | H | F | 782 |
| 14 | $(CH_2)_4SO_3Na$ | H | F | H | F | H | F | 785 |
| 21 | $(CH_2)_4SO_3Na$ | H | F | H | OMe | H | F | 783 |
| 22 | $(CH_2)_4SO_3Na$ | H | F | H | H | OBu | F | 783 |
| 23 | $(CH_2)_4SO_3Na$ | H | F | H | F | OBu | F | 789 |
| 24 | $(CH_2)_4SO_3Na$ | H | F | F | OBu | F | F | 790 |
| 16 | $(CH_2)_3SO_3Na$ | COOH | F | H | F | H | F | 785 |
| 15 | $(CH_2)_3SO_3Na$ | COOH | Cl | H | H | H | Cl | 782 |
| 26 | $(CH_2)_4SO_3Na$ | H | F | H | COOH | H | F | 782 |
| 64 | $(CH_2)_4SO_3Na$ | H | H | H | COOH | F | F | 772 |
| 65 | $(CH_2)_4SO_3Na$ | H | H | H | $(CH2)_2COOH$ | F | F | 776 |
| 63a | $(CH_2)_4SO_3Na$ | COOH | H | H | H | F | F | 770 |
| 66 | $(CH_2)_4SO_3Na$ | H | H | H | $ONH(CH_2)_5COOH$ | F | F | 773 |

Conclusion:

Halo-substituted phenyl can cause cyanine dye absorption and emission red shift, especially, halo at the $R^8$ and $R^{12}$ positions. From the experiments, F and Cl had the same effect.

The fact that the central ring is on the periphery of the chromophore makes it surprising that halogenations of that ring has such a significant effect on the absorption curves for the heptamethine dyes. The fact that modifying the ring in this way in the pentamethine dyes does not have the same effect also makes it surprising that it works in the heptamethine dyes.

Example 30

Preparation of Bioconjugates of GAM Antibody with Compound 17

Compound 17 is reconstituted in water to 1 mg/ml. Goat anti-mouse (GAM) IgG (H+L) antibodies are reconstituted typically at 1 mg/ml in PBS buffer pH 8.5. The dyes are added (at various molar excesses) to the GAM antibody samples and allowed to incubate for 2 hours at room temperature in the dark. The conjugates are extensively dialyzed against phosphate-buffered saline (PBS) buffer to remove the unconjugated free dye. The mole dye to mole protein ratios (D/P) are calculated as described below:

$$D/P = \left[\frac{A_{785}}{\varepsilon_{Dye}}\right] \div \left[\frac{A_{280} - (0.07 \times A_{785})}{\varepsilon_{antibody}}\right]$$

$\varepsilon$ dye=250,000 $M^{-1}$ $cm^{-1}$
$\varepsilon$ antibody=228,800 $M^{-1}$ $cm^{-1}$
0.07 is the correction factor for the dye absorption at 280 nm In general, if the reaction pH is too low, the amide coupling reaction will be inefficient, and the dye to protein (D/P) ratios will be much lower than expected. If necessary, additional equivalents of NHS ester can be used to drive the reaction to completion or to increase the D/P ratio.

Example 31

Preparation of Compound 17-Streptavidin Conjugates

Compound 17 is reconstituted in water to 1 mg/mL. Streptavidin is reconstituted typically at 10 mg/ml in PBS buffer (pH 8.5). The dyes are added (at various molar excesses) to the streptavidin samples and allowed to incubate for 2 h at room temperature in the dark. The conjugates are extensively dialyzed against PBS buffer to remove the unconjugated free dye. The ratio of moles of dye per mole of protein is calculated by using the equation below:

$$D/P = \left[\frac{A_{785}}{\varepsilon_{Dye}}\right] \div \left[\frac{A_{280} - (0.07 \times A_{785})}{\varepsilon_{Streptavidin}}\right]$$

In which:
$\varepsilon$ dye=250,000 $M^{-1}$ $cm^{-1}$
$\varepsilon$ streptavidin=175,000 $M^{-1}$ $cm^{-1}$
0.07 is the correction factor for the dye absorption at 280 nm In general, if the reaction pH is too low, the amide coupling reaction will be inefficient, and the dye to protein (D/P) ratios will be much lower than expected. If necessary, additional equivalents of NHS ester can be used to drive the reaction to completion or to increase the D/P ratio.

Example 32

Preparation of Bioconjugates of RGD with Compound 17

RGD peptide (1 mg) in 400 ul DMSO is added to two equivalents of compound 17 in 2 ml of pH 8.5 50 mM phosphate buffer and incubated for 3 h. The mixture is purified with reverse-phase HPLC and freeze-dried to yield a compound 17-RGD conjugate.

Example 33

Preparation of Bioconjugates of Cyclo-(RGDfK) with Compound 17

The bioconjugate of compound 17 is prepared analogously to Example 32, except that the cyclic pentapeptide cyclo(Arg-Gly-Asp-D-Phe-Lys) is used as a starting material.

Example 34

Western Blot Comparison of GAM/17 with GAM/IRDye® 800CW

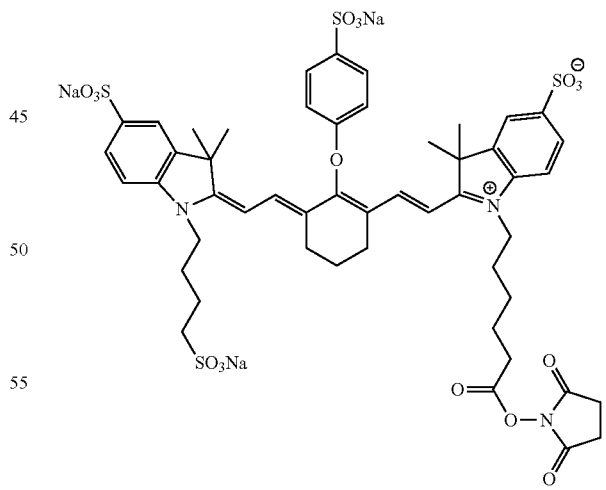

IRDye 800CW NH8 ester

Bioconjugates of 17 were compared to GAM/IRDye® 800CW conjugates in a Western blot.

Goat anti-Mouse (GAM) secondary antibodies were labeled at three dye/protein ratios (D/P=1.8, 2.8, 3.6) by the procedure of Example 30.

TABLE 3

Materials for Compound 17/GAM Western Blot

| Materials Description | Vendor | Product # | Lot # | Extra Info |
|---|---|---|---|---|
| Odyssey Blocking Buffer | LI-COR | 927-40000 | Q0741 | |
| IRDye ® 800CW/GAM | LI-COR | 926-32210 | B90608-04 | 1 mg/mL |
| 17/GAM (D/P = 1.8) | | | RAS 628055A | 0.75 mg/mL |
| 17/GAM (D/P = 2.8) | | | RAS 628055B | 0.90 mg/mL |
| 17/GAM (D/P = 3.6) | | | RAS 628055C | 0.79 mg/mL |
| 4x Protein Loading Buffer | LI-COR | 928-40004 | C00331-01 | |
| 2-color marker | LI-COR | 928-40001 | B81205-03 | Dilute 1:2; load 4 uL per well |
| Odyssey Nitrocellulose | LI-COR | 926-31092 | T908011 | |
| C32 Lysate | Santa Cruz | sc-2205 | C1605 | |
| 10% NuPAGE Bis-Tris Gels | Invitrogen | 827-09427 | 9070271 (2 gels) & 10032371 (6 gels) | |
| Pan Actin Ab-5 (ACT NO5) | Neomarkers | MS-1295 P1 | 1295P909D | dilute 1:1000 |

Methods

The Western blots contained C32 lysates and were probed with mouse anti-actin. Jurkat lysate was run (5 μg to 78 ng) by SDS PAGE and transferred to nitrocellulose. After removal from the transfer cassette, the gels were placed on filter paper to dry. The membranes were cut in half at the marker and then left to dry overnight.

The blots were blocked with Odyssey Blocking Buffer+ 0.2% Tween 20 (OBBT) for 1 hour. The primary antibody dilution was prepared in Odyssey Blocking buffer: 85 uL of Pan Actin antibody in 85 mL of Odyssey Blocking Buffer+ 0.2% Tween 20. The primary antibody solution (5 ml) was added to each blocked membrane, which was then incubated for 1 h at room temperature with rotation. The membranes were then washed with PBS with 0.1% Tween 20 (PBST) four times for 5 min each wash.

The secondary antibodies were evaluated at 0.2 μg/ml and 0.2 ng/ml final concentrations. Each solution (20 mL) was prepared by dilution to the final concentration with OBBT (0.2 μg/ml, 1:5000 equivalent; 0.2 ng/ml, 1:50,000 equivalent). These final concentrations compared to IRDye® 800CW GAM (D/P=1.8).

Each membrane was incubated in 5 mL of its respective blot for 1 h at room temperature with gentle rotation. The membranes were then washed with PBST four times for 5 min each wash.

Western blots were prepared in duplicate and assessed for signal intensity and the visual limit of detection (LOD) compared to a control (IRDye® 800CW/GAM) (FIGS. 3-6). Prior to scanning, the membranes were washed with 1×PBS (no Tween). The membranes were scanned on an Odyssey.

Results

Figure 3:
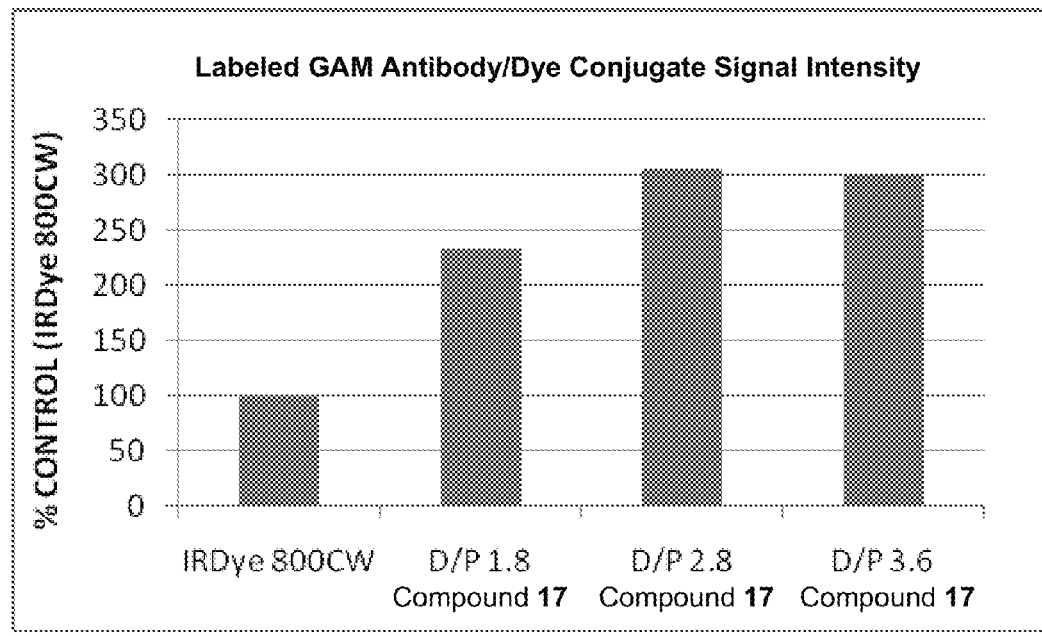
FIG. 3 shows the signal intensity of a goat anti-mouse (GAM) conjugate with compound 17 at different dye/protein (D/P) ratios and 0.2 μg/mL dilution. IRDye® 800CW was used as a control.
Figure 5:
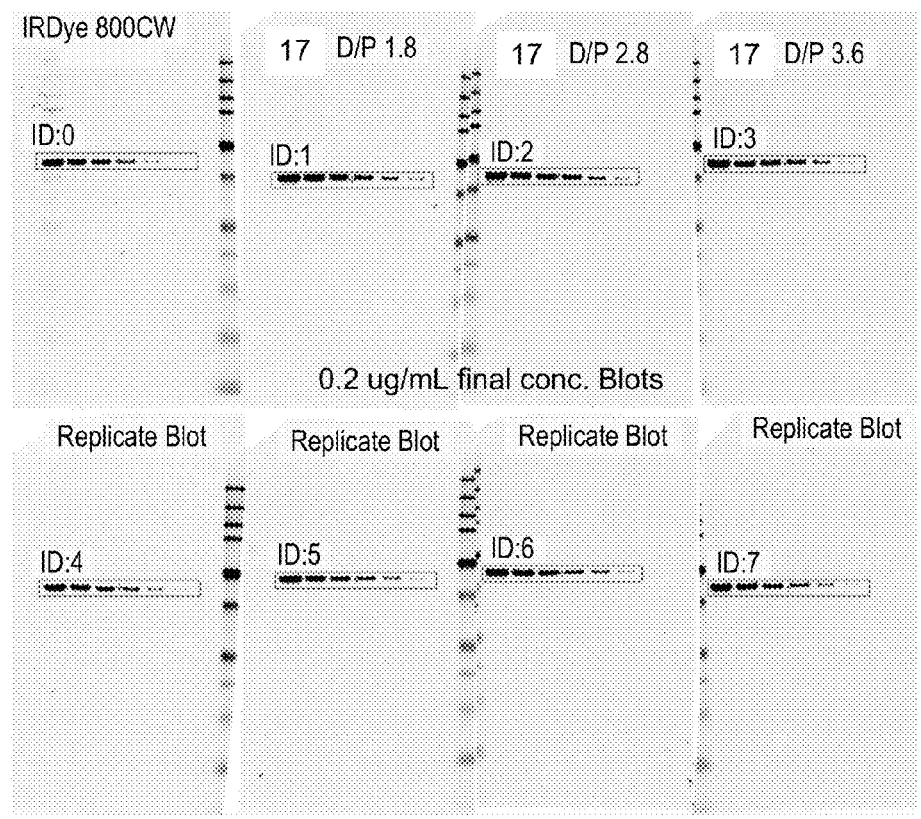
FIG. 5 illustrates a Western blot of a goat anti-mouse (GAM) conjugate with compound 17 (0.2 µg/mL). IRDye® 800CW was used as a control.

The conjugates with 17 gave a higher intensity for the actin target even at equivalent D/P ratios compared to IRDye 800CW. The intensity is about two-fold at comparable conjugate D/P ratio and about threefold at higher D/P. The background remains very low, similar to the 800CW conjugate (FIGS. 3, 5).

Figure 4:
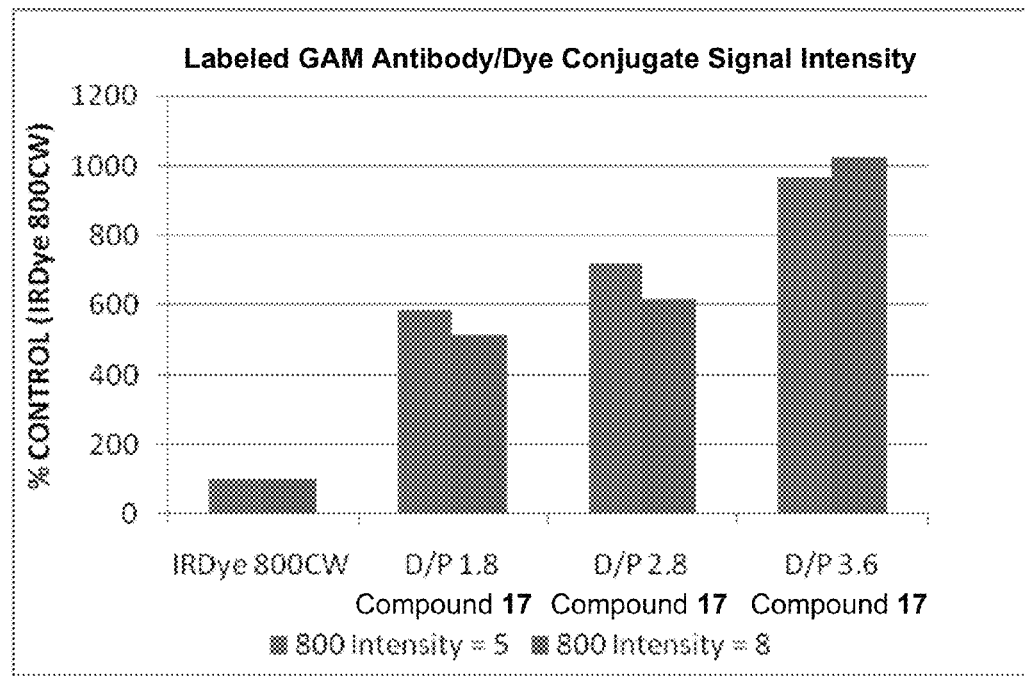
FIG. 4 shows the signal intensity of a goat anti-mouse (GAM) conjugate with compound 17 at different dye/protein (D/P) ratios and 0.2 ng/mL dilution. IRDye® 800CW was used as a control.
Figure 6:
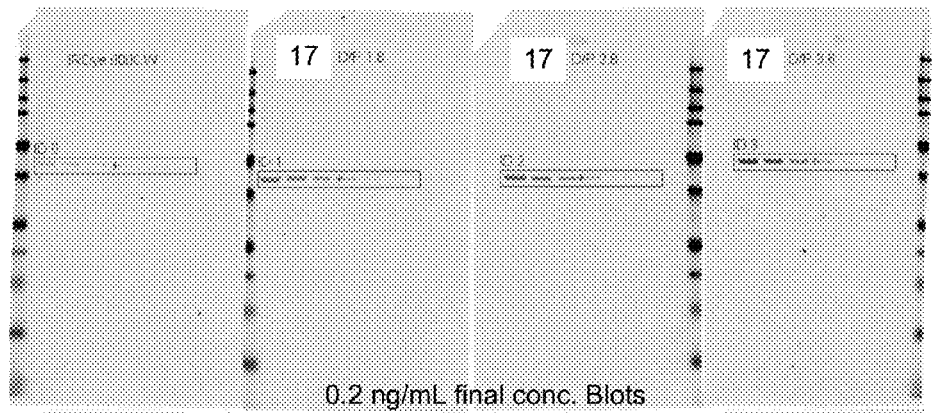
FIG. 6 illustrates a Western blot of a goat anti-mouse (GAM) conjugate with compound 17 (0.2 ng/mL). IRDye® 800CW was used as a control.

The conjugates with compound 17 perform reasonably well even at very low concentration (0.2 ng/mL) (FIGS. 4, 6). Compared to the commercial IRDye 800CW conjugate, the fluorescence intensity is about six-fold at comparable D/P and ten-fold at the highest D/P tested. The visual limit of detection for the conjugates of 17 is also slightly better than that for the IRDye 800CW control, about one two-fold dilution. At the same time the background from the membrane remained very low, and no non-specific binding of the inventive conjugates was observed even at the highest D/P examined. These are significant benefits for the conjugates of 17 compared to the current best available technology (IRDye 800CW conjugates).

Example 35

Evaluation of RGD/17 Conjugate as In Vitro Probe

RGD (Arg-Gly-Asp), the recognition motif used to bind the integrin receptors, was labeled with compound 17. The characteristics of RGD/17 conjugate and the analogous dye carboxylate 16 were evaluated in a cell-based assay.

Immunocytochemical assays provide a tool for screening a compound for specificity of a labeled agent. Binding assays give valuable information on affinity of the labeled agent to the intended target. Specificity of a labeled conjugate is demonstrated by blocking the target with an antibody or by competition with the unlabeled agent.

Procedure

Compound 17 was conjugated to the peptide RGD by the general procedure set forth in Example 32.

The cell lines U87GM and PC3MLN4 were assayed. Assays included binding, blocking, and carboxylate control. Serial dilutions of compound 16 were prepared at concentrations of 200-6.25 nM. Blocking was accomplished with unlabeled RGD at concentrations of 10-0.31 μM with the addition of 200 nM compound 17-RGD conjugates in all test wells. The compound 16 was evaluated as a dye control for non-specific binding at relatively high levels from 5-0.16 μM with U87GM cells and 1-0.002 μM with PC3 cells.

Results

Figure 7:
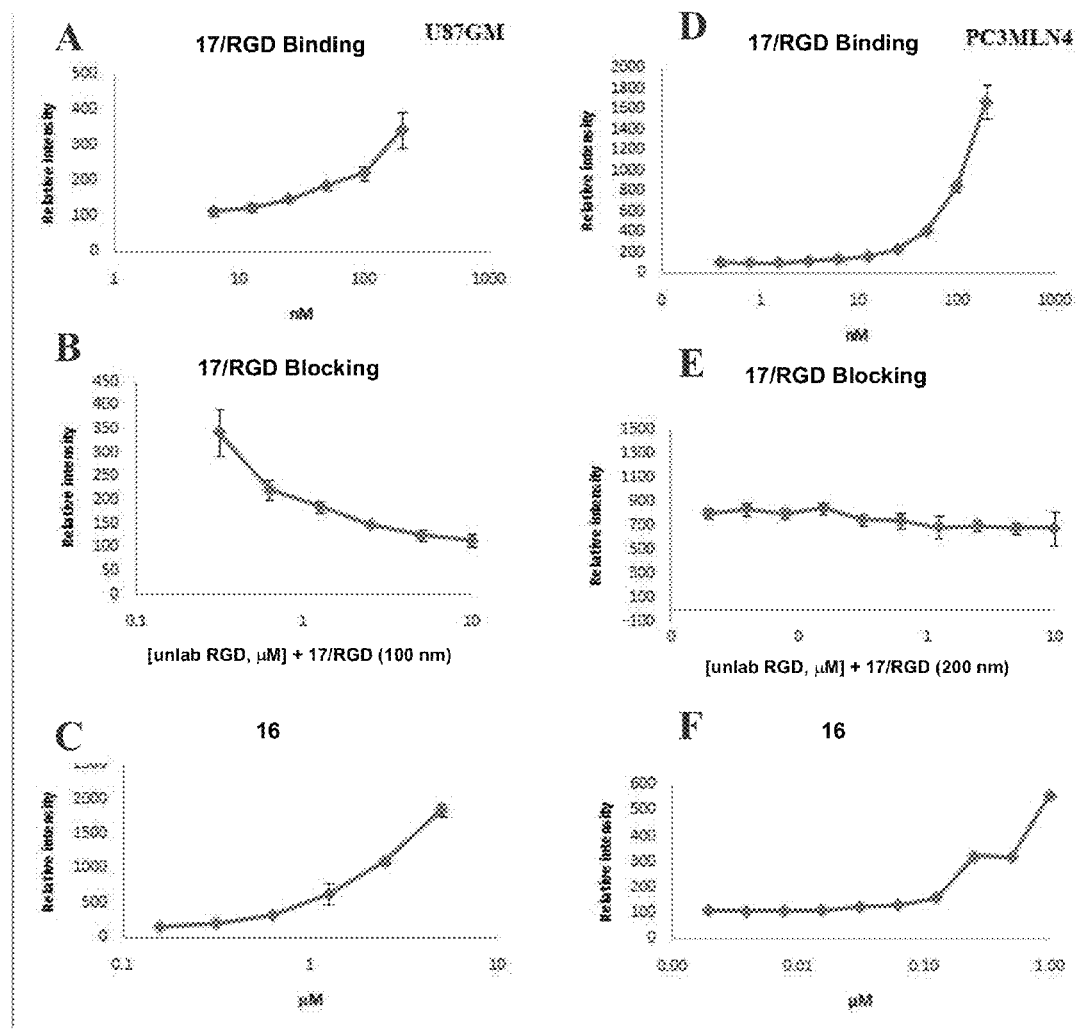
FIG. 7 illustrates an immunocytochemical assay showing U87GM binding a 17/RGD conjugate (A), a U87GM challenge with unlabeled RGD (B), and U87GM evaluation of 16 for a non-specific dye effect (C), an immunocytochemical assay showing PC3MLN4 binding a 17/RGD conjugate (D), a PC3MLN4 challenge with unlabeled RGD (E), and PC3MLN4 evaluation of 16 for a non-specific dye effect (F).

Compound 17/RGD conjugates successfully bound both U87GM and PC3 cells (FIG. 7).

Compound 16 was evaluated at significantly higher levels (up to 5 μM) for an assessment of stickiness and non-specific binding of the dye component alone in U87GM (FIG. 7C). Relatively high binding was noted above 2 μM. The level of compound 16 was reduced to a high of 1 μM to visualize the baseline/threshold for non-specific binding in PC3 cells (FIG. 7F). Relative signal intensities for 17/RGD (100 nM) were 8× higher than compound 16 (100 nM) in PC3 cells.

U87GM (FIG. 7A) and PC3 (FIG. 7D) cells exhibited a dose dependent increase in compound 17/RGD binding when incubated with increasing concentrations. Compound 17/RGD specificity was determined by treating U87GM cells with increasing concentration of unlabeled RGD (FIG. 7B). Results showed significant reduction in compound 17/RGD binding. PC3 cell competition (FIG. 7E) showed no significant reduction in compound 17/RGD binding. An increase in compound 17/RGD addition in conjunction with unlabeled RGD treatments may have been excessive.

In the second round of testing with U87GM cells, concentrations of unlabeled RGD and compound 17/RGD were increased (FIGS. 8A and 8B). Binding assay concentrations utilized 0.8-400 nM while the blocking assay used 0.06-30 µM unlabeled RGD with an addition of 200 nM 17/RGD. FIG. 8 shows second round results of binding and blocking assays in U87GM cells.

A comparison of compound 17/RGD to IRDye® 800CW RGD binding was included (FIG. 8A). The two dye-labeled probes were similar in their response when using U87GM cells. The effect of the blocking agent demonstrates the inhibition of binding (FIG. 8B).

Compound 16 vs IRDye 800CW carboxylate in vivo:

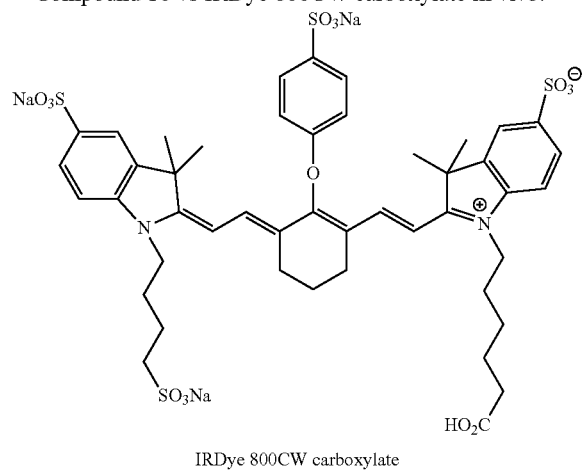

IRDye 800CW carboxylate

Two nude mice were injected with 1 nmole of either compound 16 or IRDye 800CW carboxylate. They were then imaged longitudinally over the next 24 h with the Pearl Impulse imaging system. The results are presented in FIG. 9: in vivo clearance in nudes (FIG. 9A), whole body dorsal views (FIG. 9B), and the rate of clearance (FIG. 9C). The clearance data is presented below in Table 4.

TABLE 4

Clearance Data for In Vivo Comparison of 16 and IRDye 800CW

| | | | Total | | | Min | |
|---|---|---|---|---|---|---|---|
| A. Compound 16 clearance | | | | | | | |
| 0016459_01 | 800 | 1 | 109682.80 | NaN | 1.32 | 0.64 | 1 |
| 0016471_01 | 800 | 1 | 282046.59 | NaN | 3.40 | 1.64 | 17 |
| 0016483_01 | 800 | 1 | 286573.94 | NaN | 3.45 | 1.48 | 45 |
| 0016495_01 | 800 | 1 | 266647.59 | NaN | 3.21 | 1.43 | 71 |
| 0016508_01 | 800 | 1 | 139736.97 | NaN | 1.68 | 0.60 | 190 |
| 0016520_01 | 800 | 1 | 76493.30 | NaN | 0.92 | 0.38 | 276 |
| 0016535_01 | 800 | 1 | 1652.69 | NaN | 0.02 | 0.01 | 1435 |
| B. 800CW carboxylate clearance | | | | | | | |
| 0016462_01 | 800 | 1 | 114295.49 | NaN | 1.38 | 0.79 | 3 |
| 0016474_01 | 800 | 1 | 306555.97 | NaN | 3.69 | 1.85 | 19 |
| 0016486_01 | 800 | 1 | 291381.69 | NaN | 3.51 | 1.85 | 47 |
| 0016498_01 | 800 | 1 | 272408.13 | NaN | 3.28 | 1.69 | 74 |
| 0016511_01 | 800 | 1 | 154950.09 | NaN | 1.87 | 0.99 | 192 |
| 0016523_01 | 800 | 1 | 102698.54 | NaN | 1.24 | 0.66 | 278 |
| 0016539_01 | 800 | 1 | 2336.87 | NaN | 0.03 | 0.02 | 1439 |

Example 36

Example 36 illustrates the synthesis of sodium 24(E)-2-((E)-3-((E)-2-(1-(1-azido-13-oxo-3,6,9-trioxa-12-azaocta-decan-18-yl)-3,3-dimethyl-5-sulfonatoindolin-2-ylidene) ethylidene)-2-(4-sulfonatophenoxy)cyclohex-1-enyl)vinyl)-3,3-dimethyl-1-(4-sulfonatobutyl)-3H-indolium-5-sulfonate (IRDye 800CW-PEG-Azide, 29).

29

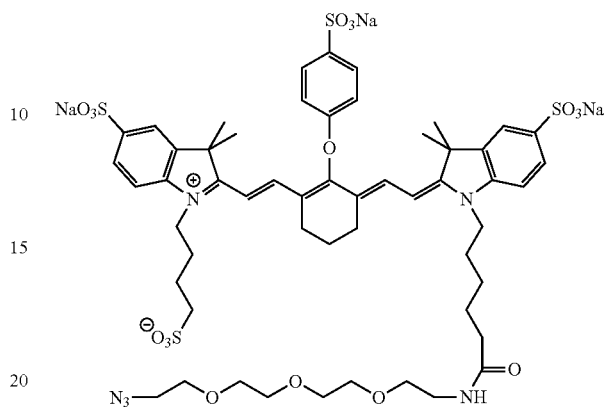

A solution of 11-azido-3,6,9-trioxaundecan-1-amine (Amino-PEG-Azide, 1.0 mg, 4.1×10$^{-3}$ mmol) and N,N-diisopropylethylamine (0.0020 mL, 1.1×10$^{-2}$ mmol) in anhydrous dimethyl sulfoxide (0.2 mL) was added to a reaction vessel containing IRDye 800CW NHS ester (5.0 mg, 4.3×10$^{-3}$ mmol). The reaction was allowed to proceed at ambient temperature for 2 hours, with periodic agitation every 15 minutes. After HPLC analysis indicated complete consumption of the IRDye 800CW NHS ester, the reaction mixture was precipitated into anhydrous diethyl ether. The ethereal layer was decanted and the crude product was purified by reverse-phase HPLC. Fractions containing the desired IRDye 800CW-PEG-Azide in ≥95% purity by HPLC analysis were combined and lyophilized to afford the product 29 as a green flocculent solid (3.4 mg, 66% based on Amino-PEG-Azide). UV/Vis (methanol) $\lambda_{max}$=778 nm; LRMS (ES/water), m/z calculated for 1203.37 [M+H]$^+$, found 1203.6 and 602.3 [M+2H]$^{2+}$.

Example 37

Example 37 illustrates the synthesis of a dye (IRDye 800CW)/dibenzocyclooctyne substrate for click chemistry (IRDye 800CW-DBCO, 30).

30

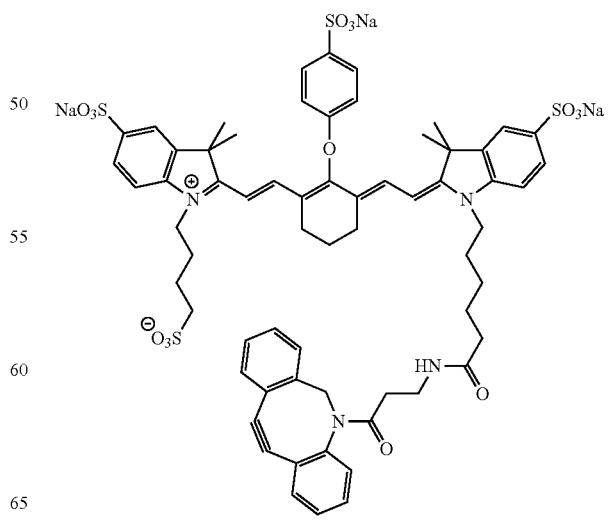

To a solution of IRDye 800CW NHS ester (5.0 mg, 4.3×$10^{-3}$ mmol) and N,N-diisopropylethylamine (0.0015 mL, 8.6×$10^{-3}$ mmol) in anhydrous dimethyl sulfoxide (0.2 mL) was added dibenzylcyclooctyne-amine (DBCO-Amine, 1.0 mg, 3.6×$10^{-3}$ mmol). After HPLC analysis showed complete consumption of the IRDye 800CW NHS ester, the reaction mixture was precipitated into anhydrous diethyl ether. The ethereal layer was decanted and the crude product was purified by reverse-phase HPLC. Fractions containing the desired IRDye 800CW-DBCO in ≥0.95% product purity by HPLC analysis were combined and lyophilized to afford the product 30 as a flocculent green solid (3.3 mg, 68% based on DBCO-Amine) UV/Vis (methanol) $\lambda_{max}$=778 nm; LRMS (ES/water), m/z calculated for 1261.4 $[M+H]^+$, found 631.4 $[M+2H]^{2+}$.

A solution of O—(N-trityl-3-aminopropyl)-O'(3-aminpropyl)-diethyleneglycol (Trt-NH-PEG$_2$-NH$_2$, 2.0 mg, 4.3×$10^{-3}$ mmol) and N,N-diisopropylethylamine (0.002 mL, 1.1×$10^{-2}$ mmol) in anhydrous dimethyl sulfoxide (0.2 mL) was added to a reaction vessel containing IRDye 800CW NHS ester (5.0 mg, 4.3×$10^{-3}$ mmol). The reaction was allowed to proceed at ambient temperature for 2 hours, with periodic vortexing at 15-minute intervals. After HPLC analysis showed complete consumption of IRDye 800CW NHS ester, the reaction was precipitated into anhydrous diethyl ether. The ethereal layer was decanted and the crude product was purified by HPLC. Fractions containing the IRDye 800CW-NH-PEG$_2$-NH-Trt in ≥95% purity were combined and concentrated in vacuo to afford a green film; the yield was presumed to be quantitative.

Example 38

Example 38 illustrates the synthesis of another IRDye 800CW derivative (IRDye 800CW-NH-(PEG)$_2$-NH-Trt, 31). See also WO 2010/002976 and Linder et al. *Bioconjugate Chem.* 2011, 22, 1287-1297, DOI: 10.1021/bc100457s.

Example 39

Example 39 illustrates the synthesis of another IRDye 800CW derivative (IRDye 800CW-NH-(PEG)$_2$-NH$_2$.TFA, 32). See also WO 2010/002976 and Linder et al. *Bioconjugate Chem.* 2011, 22, 1287-1297, DOI: 10.1021/bc100457s.

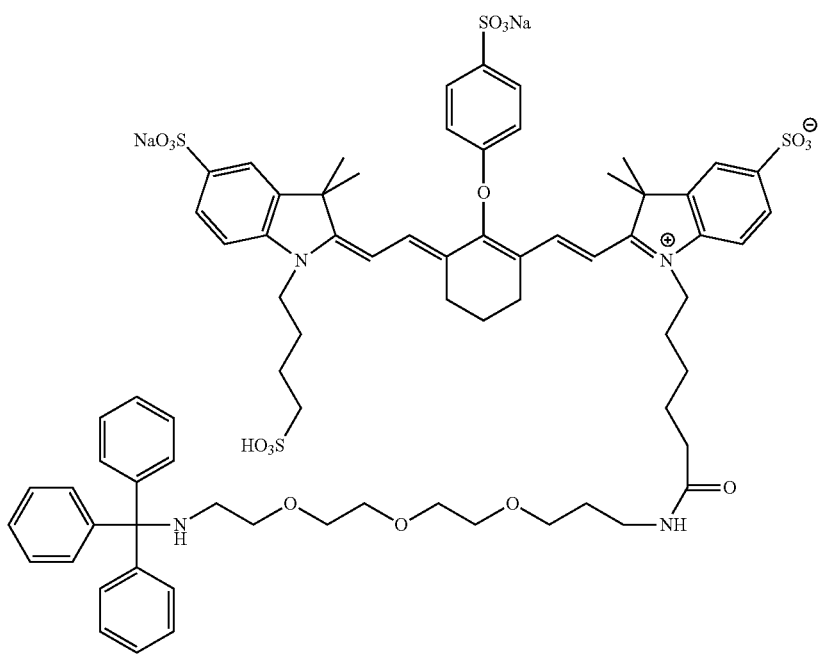

31

32

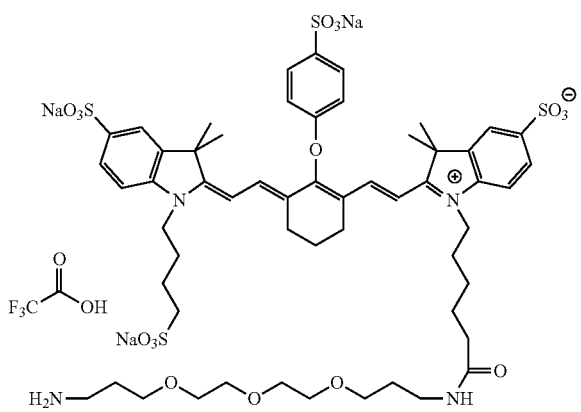

To a flask containing IRDye 800CW-NH-PEG$_2$-NH-Trt (31) (1.3 mg, 8.6×10$^{-4}$) was added a solution of trifluoroacetic acid in dichloromethane (TFA/CH$_2$Cl$_2$=1:3, 5.0 mL). The dark brown reaction was briefly swirled and allowed to proceed at ambient temperature for 30 minutes. The volatiles were removed in vacuo and the residuals were treated again with TFA/CH$_2$Cl$_2$ (1:3, 5.0 mL) for 30 minutes. After removing the volatiles in vacuo, the residuals were washed with anhydrous diethyl ether. The ethereal layer was decanted and the IRDye 800CW-NH-(PEG)$_2$-NH$_2$.TFA (32) was used without further purification; the yield was presumed to be quantitative. UV/Vis (methanol) $\lambda_{max}$=778 nm; LRMS (water) m/z calculated for 1205.4 [M+H]$^+$, found 1205.6, 603.3 [M+2H]$^{2+}$.

Example 40

Example 40 illustrates the synthesis of another IRDye 800CW derivative (IRDye 800CW-PEG-Phosphine, 33a).

To a solution of IRDye 800CW-NH-(PEG)$_2$-NH$_2$.TFA (5.9 mg, 4.3×10$^{-3}$ mmol) in anhydrous dimethyl sulfoxide (0.2 mL) was added NHS-Phosphine (2.0 mg, 4.3×10$^{-3}$ mmol, commercially available from ThermoScientific/Pierce) followed by N,N-diisopropylethylamine (0.002 mL, 1.1×10$^{-2}$ mmol). The reaction was allowed to proceed at ambient temperature for 2 hours, with periodic agitation at 15-minute intervals. After HPLC analysis showed near-complete consumption of the IRDye 800CW-NH-(PEG)$_2$-NH$_2$.TFA, the reaction was precipitated into anhydrous diethyl ether. The ethereal layer was decanted and the crude product was purified by HPLC. Fractions containing the presumed IRDye 800CW-PEG-Phosphine in ≥95% purity were combined and concentrated in vacuo to afford a green solid (0.9 mg, 13% based on IRDye 800CW-NH-(PEG)$_2$-NH$_2$.TFA); UV-Vis (methanol) $\lambda_{max}$=778 nm; LRMS (water) m/z calculated for 1551.5 [M+H]$^+$, found 776.7 [M+2H]$^{2+}$.

Example 41

Example 41 illustrates a phosphine oxide side product from the synthesis of Example 102 (IRDye 800CW-PEG-Phosphine Oxide, 33b).

33a

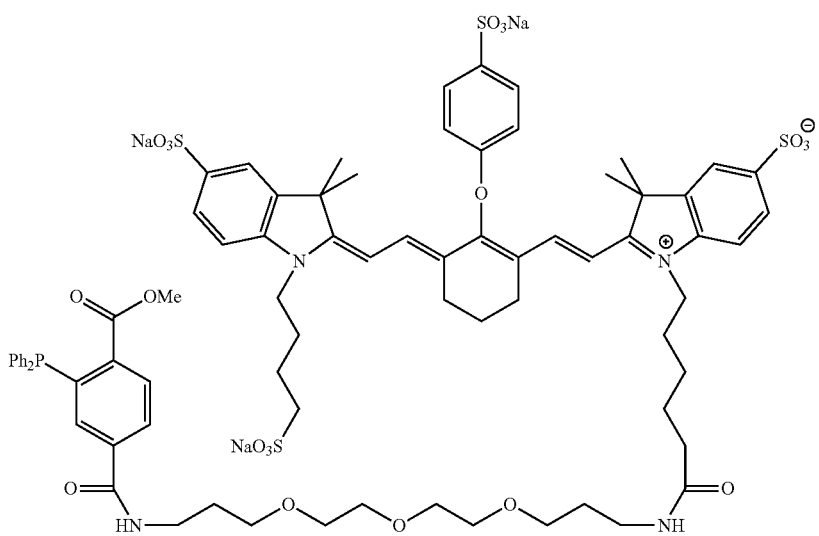

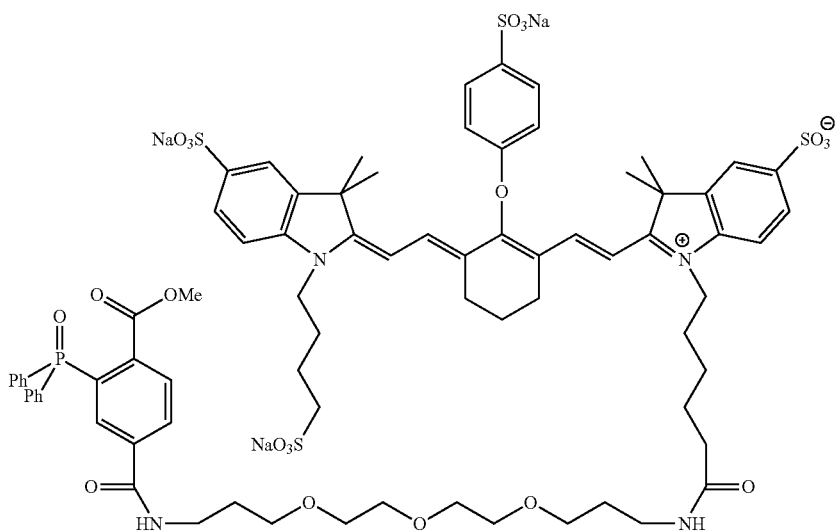

33b

This compound was isolated as a substantial byproduct from the synthesis of IRDye 800CW-PEG-Phosphine. This byproduct is nonfunctional and causes background problems. The compound is a green solid (17% based IRDye 800CW-NH-(PEG)$_2$-NH$_2$.TFA); UV-Vis (methanol) $\lambda_{max}$=778 nm; LRMS (water) m/z calculated for 1567.5 [M+H]$^+$, found 784.5 [M+2H]$^{2+}$.

Example 42

Example 42 illustrates a non-catalyzed click chemistry synthesis reaction.

Bertozzi et al. (Aldrichimica Acta, 2010, 43(i), 15-23 and references therein) have developed a bio-orthogonal labeling method that employs modified sugars. Cells incubated in a growth medium containing these modified azido sugars will absorb the sugars and perhaps incorporate the sugars on cell surface glycans (i.e., glycol-proteins and glycolipids). Upon exposing the azido-sugar labeled cells to appropriate phosphine or alkyne reagents, a click-type reactions will occur (either a Staudinger ligation or Huisgen cycloaddition, respectively). If the phosphine or alkyne bears a reporter group (e.g., a dye), then the cells is labeled as shown below in Scheme 1:

Scheme 1: Biocompatible Labeling with Click Chemistry

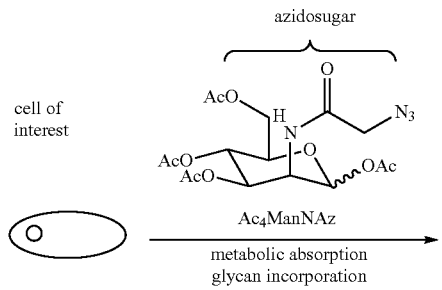

-continued

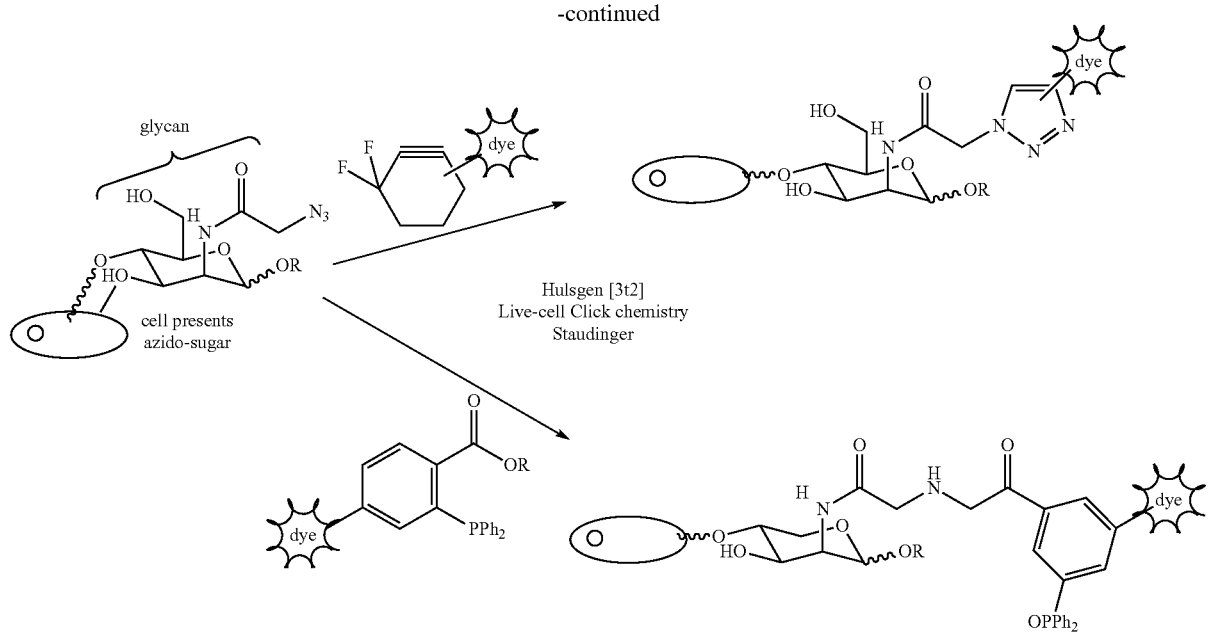

In this example, the reaction is carried-out with IRDye 800CW as a sample dye, but this proceeding is also applicable to the dye(s) of the present invention. The conjugate has the following advantages: (1) This type of bio-orthogonal labeling does not entail genetic engineering. Although many biological researchers study transgenic organisms, developmental biologists simply want to monitor "normal" changes in biochemical morphology. (2) The click reagents are highly chemoselective and typically do not react with biological nucleophiles (although strained alkynes may be susceptible to thiols). (3) The click chemistry can be performed on living cells and whole organisms.

In some embodiments, the compounds of the present invention are used to monitor azido-labeled molecules (e.g., azido sugar, protein bearing azido amino acids, lipids and site-specifically labeled proteins) in live cells. The metabolic precursor peracetylated N-azidoacetylmannosamine ($Ac_4ManNAz$) is metabolically adsorbed into cells of interest and incorporated into biomolecules that are expressed on the surface of the cells. In certain stances, the azido-sugar labeled cells are exposed to a cyclooctyne (strained alkyne) reagent conjugated to a reporter group (e.g., dye), which generates a Huisgen cycloaddition reaction. The cyclooctyne reagent can be added to cell culture medium and incubated with azido-sugar labeled cells at conditions that promote the click reaction. If the azido-sugar labeled cells are in a live organism, the cyclooctyne reagent can be administered to the organism by methods such as, but not limited to, oral, topical and trans-membrane administration, and injection. As a result, the cyclooctyne-reporter conjugate covalently binds to the azido-sugar labeled cells, which then labels the cells with the reporter. In other instances, the azido-sugar labeled cells are exposed to a phosphine reagent conjugated to a reporter group (e.g., dye), which generates a Staudinger ligation between the phosphine and the azido sugar. This covalently binds the phosphine-reporter conjugate to the azido-sugar labeled cells, which are now detectable using commercially available imaging systems.

In other embodiments, $Ac_4ManNAz$ is administered to a whole organism. In certain instances, it is injected into an animal (e.g., zebrafish, rodents, rabbits, dogs, sheep, goats, pigs, monkey, and humans; preferably zebrafish, rodents). This method delivers azides to cell surface sialoglycoconjugates on cells found in serum and various tissues, such as, but not limited to heart, spleen, liver, kidney, intestines and muscle. In some instances, a phosphine- or alkyne-reporter can be injected into the same animal to generate a Huisgen cycloaddition reaction or Staudinger ligation, respectively, in vivo. The labeled tissues and cells can be monitored and analyzed using whole animal imaging systems. In other instances, tissues or cells are extracted from an $Ac_4ManNAz$ injected animal, and then they are treated with a phosphine- or alkyne-reporter in vitro. Methods known to those skilled in the art, such as, but not limited to Western blotting, ELISA, immunocytochemistry, mass spectrometry, and high-performance liquid chromatography can then be used to detect labeled biomolecules.

Example 43

Example 43 illustrates methods of using compounds of the present invention to label biomolecules (e.g., proteins, lipids, carbohydrates, nucleic acids, amino acids, glycerol, fatty acids, and nucleotides) on cells as shown in Scheme 2. It also illustrates methods of in vitro and in vivo analysis of the labeled biomolecules that can serve as a detection probe. The compounds can be applied to methodologies used to investigate disease and therapeutic development, such as but not limited to tumor imaging, glycan labeling, in vivo imaging, and cell surface modification.

Example 43 illustrates an ELISA using click chemistry.

Scheme 2: ELISA with Click Chemistry

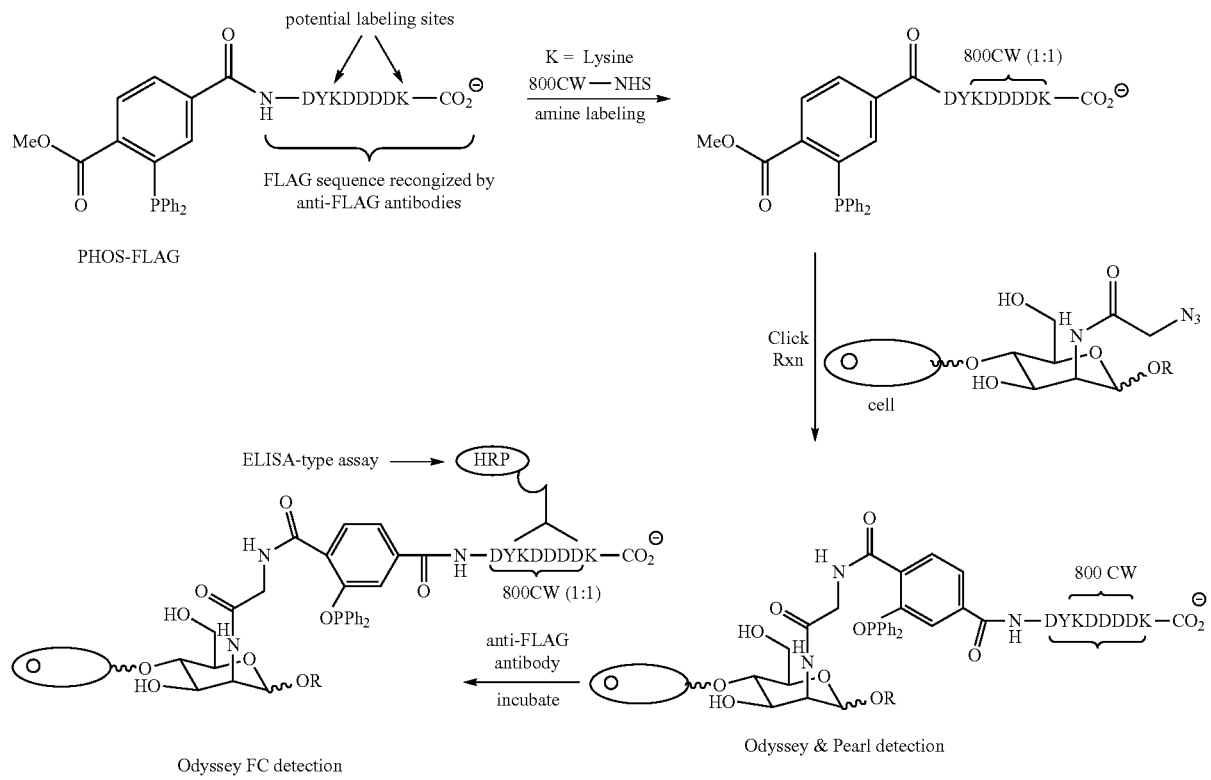

In this example, the reaction is carried-out with IRDye 800CW as a sample dye, but this proceeding is also applicable to the dye(s) of the present invention.

Metabolic Labeling of an Bioorthogonal Functional Group on Biomolecules

In some embodiments, an azido-labeled biomolecule is made using methods known to those skilled in the art. In certain instances, an unnatural azido sugar is commercially available from a supplier (e.g., Sigma-Aldrich). In other instances, the unnatural azido sugar, such as the metabolic precursor peracetylated N-azidoacetylmannosamine ($Ac_4ManNAz$)) is synthesized according to methods known to those skilled in the art (see, e.g., Laughlin et al., Methods Enzymol, 415, 230-250 (2006)). To incorporate an azido sugar into biomolecules expressed on cells cultured in vitro, the modified sugar is added to the cell culture media and incubated with the cells (see, e.g., Bussink et al., J. Lipid Res., 48, 1417-1421 (2007); Prescher et al., Nature, 430, 873-877 (2004)). Typically, $Ac_4ManNAz$ is added to a cell culture at a final concentration of about 50 μM and incubated for about 3 days in cell culturing conditions. To label biomolecules expressed on cells in an organism, an azido sugar (e.g., $Ac_4ManNAz$) is administered in a solution to the organism by injection (e.g., intraperitoneal injection) at an appropriate injection schedule to ensure optimal incorporation and expression of the modified biomolecule. See Chang et al., Proc. Natl. Acad. Sci. U.S.A., 107, 1821-1826 (2010). Non-limiting examples of organisms include fish, rodents, rabbits, dogs, sheep, goats, pigs, monkey, and humans. Typically, $Ac_4ManNAz$ is injected intraperitoneally at a dose of 300 mg/kg in DMSO solution into mice once daily for 7 days.

Generation of PHOS-FLAG-Reporter Probe

Scheme 2 illustrates one embodiment of the invention, wherein a PHOS-FLAG-800CW probe is used to label specific azido-sugar labeled biomolecules in living cells and organisms. In some embodiments, a phosphine-FLAG peptide conjugate (PHOS-FLAG; described in Laughlin et al., Methods Enzymol, 415, 230-250 (2006)) is coupled to a reporter group (e.g., dye) using methods known to those skilled in the art. In certain instances, the phosphine-FLAG peptide conjugate is labeled with IRDye 800CW NHS ester (LI-COR) according to manufacturer's instructions. The resulting PHOS-FLAG-800CW probe can then be covalently linked via a Staudinger ligation to an azido-labeled biomolecule expressed by a cell.

Detection of Biomolecules Labeled by Copper-Free Click Chemistry

Scheme 2 also illustrates a method of labeling a modified biomolecule found on cell with a PHOS-FLAG-Reporter probe using "click" chemistry.

In some embodiments, a PHOS-FLAG-800CW probe is injected into an animal having cells that express azido-labeled biomolecules. In particular instances, mice are injected intraperitoneally once with PHOS-FLAG-800CW (0.16 mmol/kg). Labeling of the cells with the near-infrared dye is detected using a whole animal detection system (e.g., the Pearl Imager (LI-COR)). Dye-labeled biomolecules, tissues and cells from the animal can be harvested from a euthanized animal and analyzed using imagers (e.g., the Odyssey System (LI-COR)).

In other embodiments, a PHOS-FLAG-800CW probe is added to an in vitro cell culture and incubated in conditions that promote a Staudinger ligation reaction between the phosphine of the probe and the azide of the biomolecule. In certain instances, the "click" reaction is performed according to the following steps: 1) azido-labeled cells are collected; 2) they are centrifuged at 1,500 rpm for 10 minutes, 3) they are washed three times in cold PBS, 4) they are resuspended in 2% (v/v) fetal calf serum in PBS, 5) they are incubated with about 0.5 mM PHOS-FLAG-800CW probe at room temperature for 3 hours under mild shaking, 6) the cells are collected by centrifugation, and 7) they are washed three times with cold PBS. As a result of click chemistry, the labeled biomolecule is covalently linked to a FLAG tag and near-infrared dye via the click product. In some instances, the near-infrared dye-labeled cells or biomolecules are detected and analyzed using a detection system (e.g., Odyssey System (LI-COR)).

In certain embodiments, an ELISA-type assay is performed to detect the FLAG-tagged biomolecules expressed on cells. Protocols for ELISA-type assays and immunocytochemistry are known to those of skill and described in detail in reference books, such as *Antibodies: A Laboratory Manual* (ed. Harlow and Lane), Cold Spring Harbor Laboratory Press, New York, 1988; *Methods in Molecular Biology, Volume* 42: *ELISA, Theory and Practice* (ed. Coligan et al.), Humana Press, New Jersey, 1995; and *Immunoassay* (ed. Diamandis and Christopoulos), Academic Press, New York, 1996. In some aspects, the labeled cells are incubated with a horseradish peroxidase (HRP)-conjugated anti-FLAG antibody at conditions optimal for antibody binding. HRP conjugated anti-FLAG antibodies are commercially available from suppliers such as, but not limited to, Sigma-Aldrich (St. Louis, Mo.), Cell Signaling (Danvers, Mass.), Protein Mods (Madison, Wis.), Prospec Bio (East Brunswick, N.J.). The antibody-labeled cells are exposed to a luminol substrate that is oxidized by HRP in a chemiluminescent reaction. The light-emitting reaction is detectable using imaging systems such as, but not limited to Odyssey Fc System (LI-COR). In other aspects, the FLAG tagged biomolecules are extracted from the cells using methods known to those skilled in the art. Descriptions of methods for the isolation of biomolecules and the detection of FLAG-tagged biomolecules can be found in references such as, but not limited to, *Current Protocols in Molecular Biology* (ed. Ausubel et al.), Wiley, New Jersey, 2011; and *Current Protocols in Immunology* (ed. Coligan et al.), Wiley, New Jersey, 2011.

Example 44

Example 44 illustrates the compounds of the present invention with technology similar to Rutjes (cf. *ChemBioChem* 2007, 8, 1504-1508) using copper-free click chemistry reaction conditions as shown in Scheme 3. This example illustrates a method of covalently binding a near-infrared dye to selectively modified biomolecules that are expressed by cells. Non-limiting examples of applications of the methods described here in are tumor imaging, glycan labeling, in vivo labeling, cell surface modification, The method is based on a tandem [3+2] cycloaddition-retro-Diels-Alder ligation method that results in a stable 1,2,3-triazole linkage.

Scheme 3

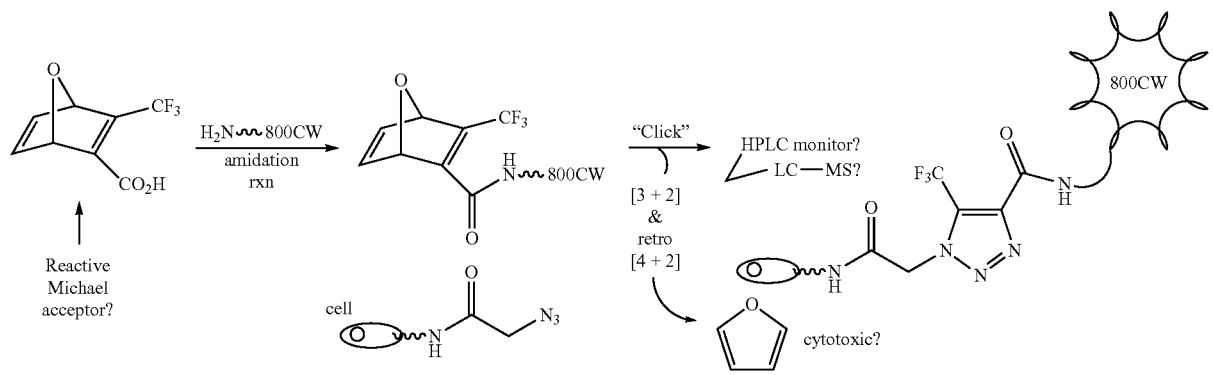

In this example, the reaction is carried-out with IRDye 800CW as a sample dye, but this proceeding is also applicable toe the dye(s) of the present invention.

Scheme 3 illustrates a method of linking a near-infrared dye to an azido-labeled biomolecule. In some embodiments, firstly, an oxanorbornadiene is coupled to a near-infrared dye (e.g., IRDye 800CW) via an amidation reaction to generate an IRDye800CW-oxanorbornadiene. Next, the IRDye800CW-oxanorbornadiene reagent is incubated with cells expressing an azido labeled biomolecule, thereby creating a "click" reaction. Typically, azido labeled cells are generated following methods described in Example 43. The tandem [3+2] cycloaddition and retro-Diels-Alder reactions generate a furan molecule and a triazole linkage between the biomolecule and the dye, thereby labeling targeted cells with a dye.

In certain embodiments, a IRDye800CW-oxanorbornadiene reacts with a selectively modified azido-biomolecule on cells in an animal. The IRDye800CW-oxanorbornadiene can be administered (e.g., injection, oral, transdermal and topical) to an animal. In some instances, the IRDye800CW-labeled cells and biomolecules are monitored in the animal using an infrared detection system (e.g., Pearl Imager). In other instances, cells and tissues from the animal are harvested and analyzed using techniques known to those in skilled in the art, such as, but not limited to ELISA, FLISA, Western, histology, immunocytochemistry, and imaging. Methods including protocols are available in references such as, but not limited to

*Current Protocols in Molecular Biology* (ed. Ausubel et al.), Wiley, New Jersey, 2011; *Current Protocols in Protein Science* (ed. Coligan et al.), Wiley, New Jersey, 2011; and *Current Protocols in Immunology* (ed. Coligan et al.), Wiley, New Jersey, 2011. In some instances, the labeled biomolecules and cells are monitored using techniques described in Example 43.

In certain embodiments, the labeled biomolecule is detected and identified using methods such as, but not limited to high-performance liquid chromatography (HPLC) and liquid chromatography-mass spectrometry (LC-MS). Methods of detecting dye-labeled cells and biomolecules are described in references, for example, *Peptide Characterization and Application Protocols* (ed. Fields), Humana Press, New Jersey, 2007; *Sample Preparation in Biological Mass Spectrometry* (ed. Ivanov and Lazarev), Springer, New York, 2010; and *Proteomic Biology Using LC-MS: Large Scale Analysis of Cellular Dynamics and Function*, (ed. Takahashi and Isobe), Wiley, New Jersey, 2008. In some instances, the labeled biomolecule is a constituent of a molecular complex and methods of dissociating, separating or modifying the complex are used prior to performing methods for detecting and identifying the individual labeled peptides. Examples include, but are not limited to LC-MS with peptide mass fingerprinting and tandem MS (LC-MS/MS).

Compound 34 was prepared by combining 60 mg of compound 25a, 32 mg of N,N'-disuccinimidyl carbonate, 10.8 μL of N,N-diisopropylethylamine, and 3 mL of DMSO. The mixture was stirred at room temperature for 30 minutes, precipitated into diethyl ether, and then purified by reverse-phase C18 chromatography using acetonitrile/water, yielding 29.8 mg of blue-green solid.

Example 46

Example 46 illustrates the synthesis of a TFA salt of the fluorescence-quenching dye sodium 1-(6-(6-aminohexylamino)-6-oxohexyl)-2-((E)-2-((E)-3-((E)-2-(3,3-dimethyl-5-sulfonato-1-(4-sulfonatobutyl)indolin-2-ylidene)ethylidene)-2-(4-sulfonatophenoxy)cyclohex-1-enyl)vinyl)-3,3-dimethyl-3H-indolium-5-sulfonate (IRDye 800CW-Hexamethylenediamine, 35a).

Example 45

Example 45 illustrates the synthesis of sodium 3,3'-(2-((E)-2-((E)-3-((E)-2-(3-(6-(2,5-dioxopyrrolidin-1-yloxy)-6-oxohexyl)-1,1-dimethyl-7-sulfonato-1H-benzo[e]indol-2(3H)-ylidene)ethylidene)-2-(2-fluorophenyl)cyclohex-1-enyl)vinyl)-3,3-dimethyl-1-(3-sulfonatopropyl)-3H-indolium-5-ylazanediyl)dipropane-1-sulfonate (34).

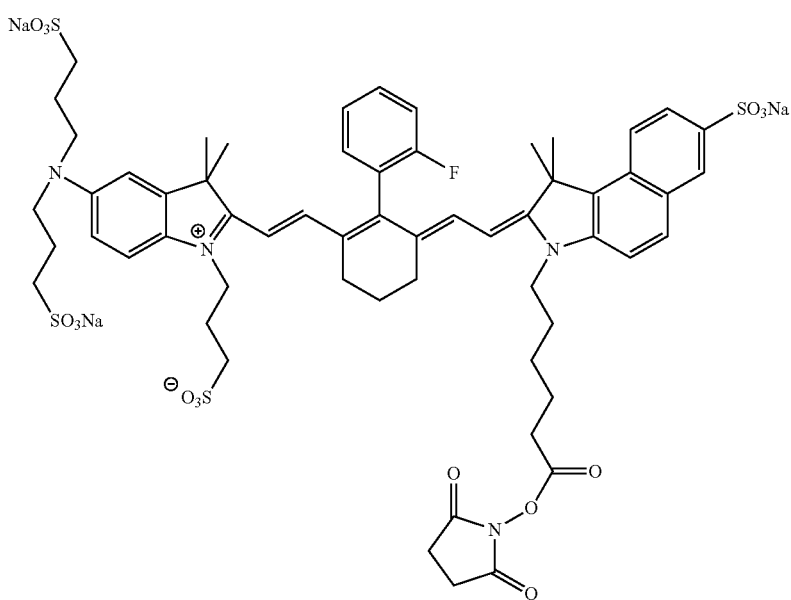

34

73 74
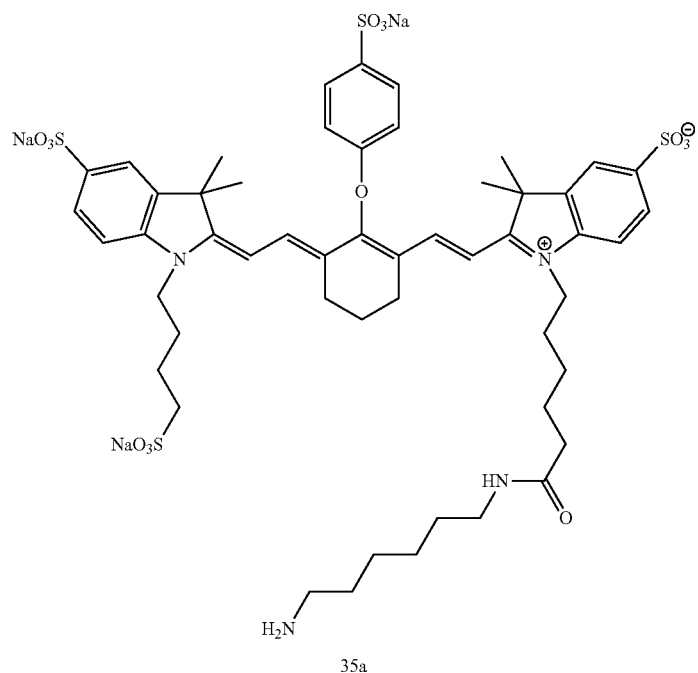
35a
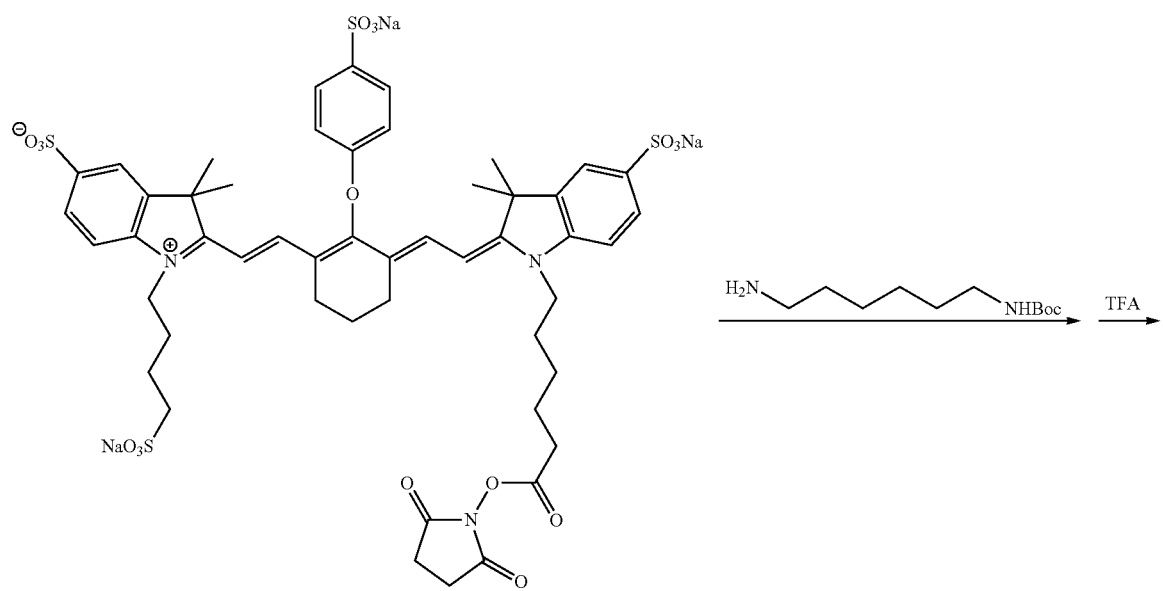
36

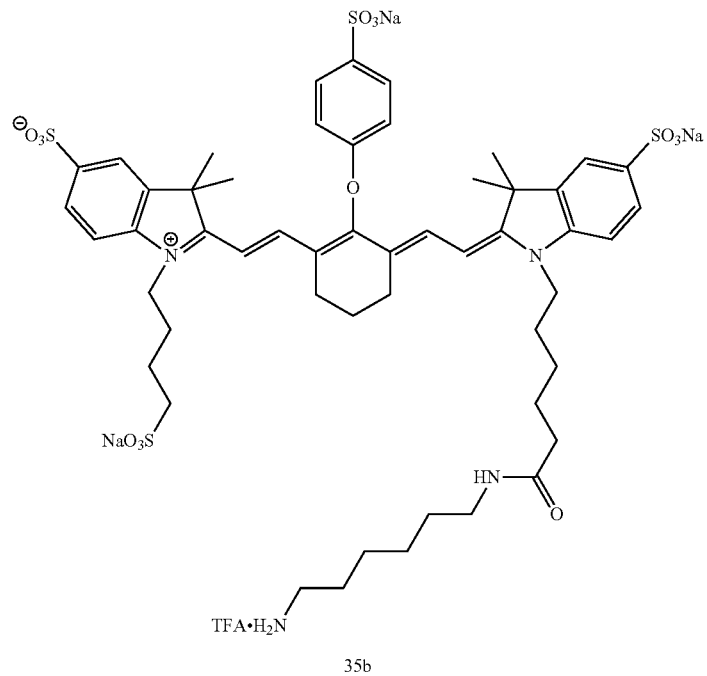

35b

The IRDye 800CW NHS ester 36 (300 mg, 0.3 mmol) was reacted with N-Boc-1,6-hexanediamine (167.5 mg, 0.8 mmol) in 10 ml DMSO under $N_2$ for 2 hours, then the mixture was precipitated by ether and purified by C18 flash chromatography. The resulting material was then deprotected by TFA to afford the compound 35b as a green solid that was used without further purification.

ylidene)ethylidene)-2-(4-sulfonatophenoxy)cyclohex-1-enyl)vinyl)-3,3-dimethyl-5-sulfonato-3H-indolium-1-yl) hexanamido)hexylamino)-6-oxohexyl)-1,1-dimethyl-7-sulfonato-1H-benzo[e]indolium-2-yl)vinyl)-2-(2-fluorophenyl)cyclohex-2-enylidene)ethylidene)-3,3-dimethyl-1-(3-sulfonatopropyl)indolin-5-ylazanediyl) dipropane-1-sulfonate (800CW-NH—$(CH_2)_6$—NH-Compound 25a, 8-atom linker; 37).

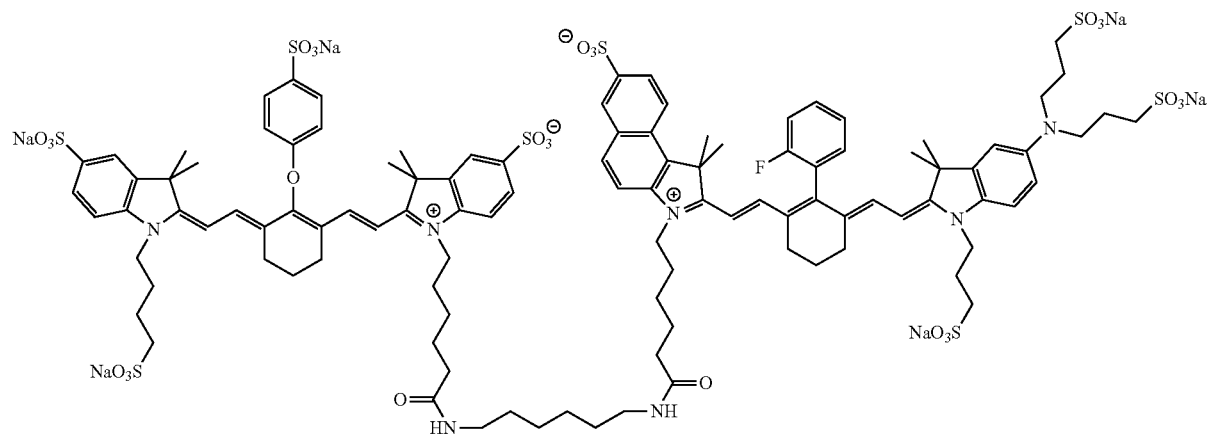

Example 47

Example 47 illustrates the synthesis of sodium 3,3'-((E)-2-((E)-2-(3-((E)-2-(3-(6-(6-(6-(2-((E)-2-((E)-3-((E)-2-(3,3-dimethyl-5-sulfonato-1-(4-sulfonatobutyl)indolin-2-

A solution of IRDye 800CW-Hexamethylenediamine.TFA (35b) (64 μg, $5.0 \times 10^{-2}$ μmol) and N,N-diisopropylethylamine (0.1 4, $5.7 \times 10^{-1}$ μmol) in anhydrous dimethyl sulfoxide (200 μL) was added to a vessel containing compound 34 (100 μg, $7.7 \times 10^{-2}$ μmol). The reaction mixture was agitated for 30 seconds and then allowed to proceed at ambient temperature for 2 hours. After HPLC analysis showed the complete consumption of 800CW-Hexamethylenediamine.TFA, the reaction mixture was precipitated into dry diethyl ether. The ethereal layer was decanted and the crude product residue was purified by reverse-phase HPLC to afford the product 37 as a teal solid. The exact yield was not determined. UV/Vis (acetonitrile/water=1:1) $\lambda_{max}1=778$ nm, $\lambda_{max}2=830$ nm; LRMS (ES/water), m/z calculated for $C_{107}H_{133}FN_7O_{27}S_8$ [M+H]$^+$2222.74, found 742.5 [M+3H]$^{3+}$, 1113.1 [M+H]$^{2+}$.

Example 48

Example 48 illustrates the synthesis of sodium 3,3'-((E)-2-((E)-2-((3-((E)-2-(3-(27-(2-((E)-2-((E)-3-((E)-2-(3,3-dimethyl-5-sulfonato-1-(4-sulfonatobutyl)indolin-2-ylidene)ethylidene)-2-(4-sulfonatophenoxy)cyclohex-1-enyl)vinyl)-3,3-dimethyl-5-sulfonato-3H-indolium-1-yl)-6,22-dioxo-11,14,17-trioxa-7,21-diazaheptacosyl)-1,1-dimethyl-7-sulfonato-1H-benzo[e]indolium-2-yl)vinyl)-2-(2-fluorophenyl)cyclohex-2-enylidene)ethylidene)-3,3-dimethyl-1-(3-sulfonatopropyl)indolin-5-ylazanediyl)dipropane-1-sulfonate (800CW-NH-(PEG)$_2$-NH-Compound25a, 15-atom linker; 38).

This compound was prepared in a manner similar to 37 (Example 47) from the corresponding IRDye 800CW-NH-(PEG)$_2$-NH$_2$.TFA (32). The exact yield was not determined. UV/Vis (acetonitrile/water=1:1) $\lambda_{max}1=778$ nm, $\lambda_{max}2=830$ nm; (ES/water), m/z calculated for $C_{111}H_{141}FN_7O_{30}S_8$[M+H]$^+$2326.75, found 776.8 [M+3H]$^{3+}$ and 1164.1 [M+2H]$^{2+}$.

Example 49

Example 49 illustrates the synthesis of sodium 3,3'4(E)-2-((E)-2-(3-((E)-2-(3-(49-(2-((E)-2-((E)-3-((E)-2-(3,3-dimethyl-5-sulfonato-1-(4-sulfonatobutyl)indolin-2-ylidene)ethylidene)-2-(4-sulfonatophenoxy)cyclohex-1-enyl)vinyl)-3,3-dimethyl-5-sulfonato-3H-indolium-1-yl)-6,44-dioxo-10,13,16,19,22,25,28,31,34,37,40-undecaoxa-7,43-diazanonatetracontyl)-1,1-dimethyl-7-sulfonato-1H-benzo[e]indolium-2-yl)vinyl)-2-(2-fluorophenyl)cyclohex-2-enylidene)ethylidene)-3,3-dimethyl-1-(3-sulfonatopropyl)indolin-5-ylazanediyl)dipropane-1-sulfonate (800CW-NH-dPEG$_{11}$-NH-Compound25a, 37-atom linker; 39).

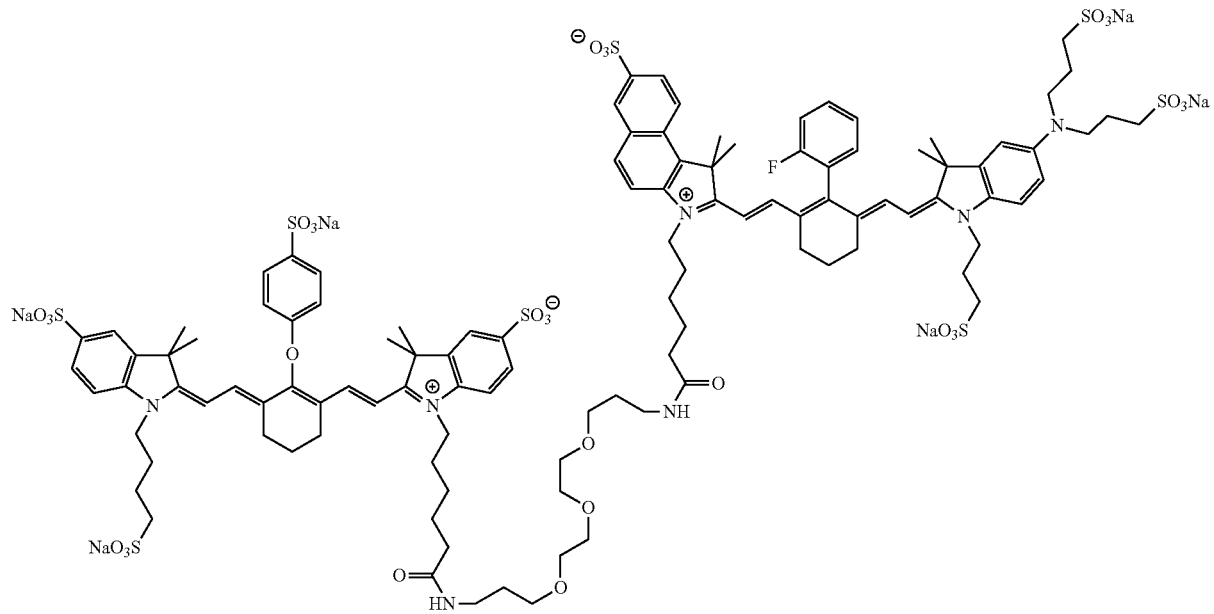

38

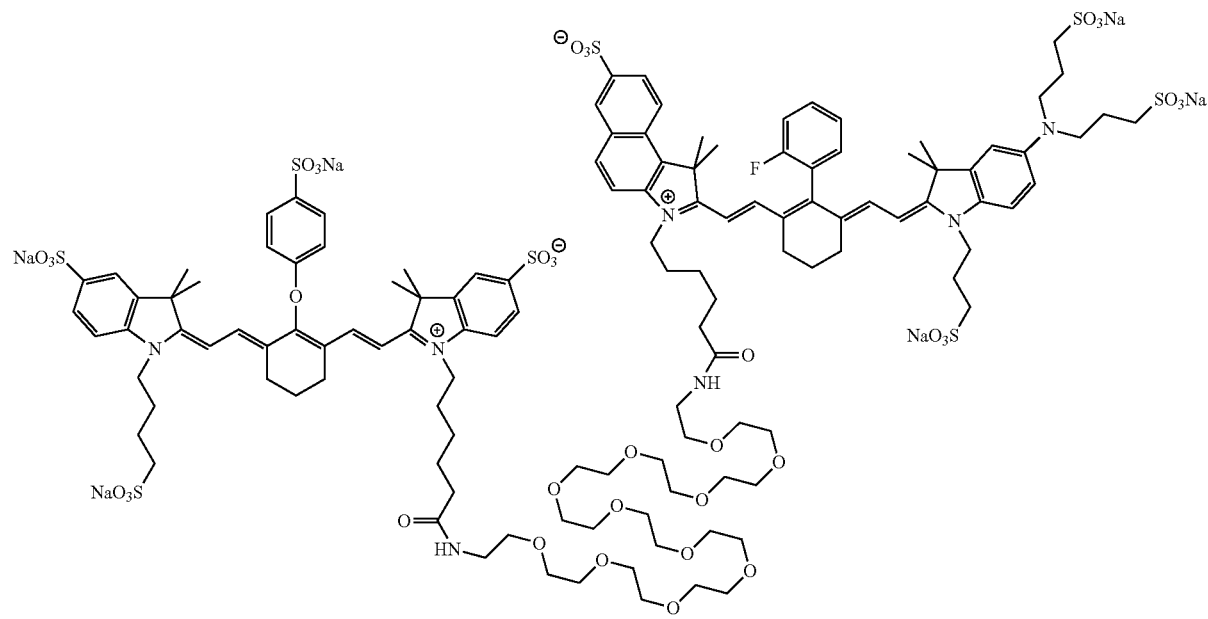

39

This compound was prepared in a manner similar to 52 (Example 62) from the corresponding IRDye 800CW-NH-dPEG$_{11}$®—NH$_2$.TFA, which was prepared by a method analogous to that used to prepare compound 32 from Boc-NH-dPEG$_{11}$®-NH$_2$ (Quanta Biodesign, Inc.) (Example 39). The exact yield was not determined. UV/Vis (acetonitrile/water=1:1) $\lambda_{max}1$=777 nm, $\lambda_{max}2$=830 nm; LRMS (ES/water), m/z calculated for C$_{125}$H$_{169}$FN$_7$O$_{38}$S$_8$ [M+H]' 2650.93, found 884.9 [M+3H]$^{3+}$ and 1337.6 [M+2H]$^{2+}$.

Example 50

Example 50 illustrates the synthesis of a strained cycloalkyne-containing a compound 25a derivative for click chemistry (Compound 25a-DBCO, 40).

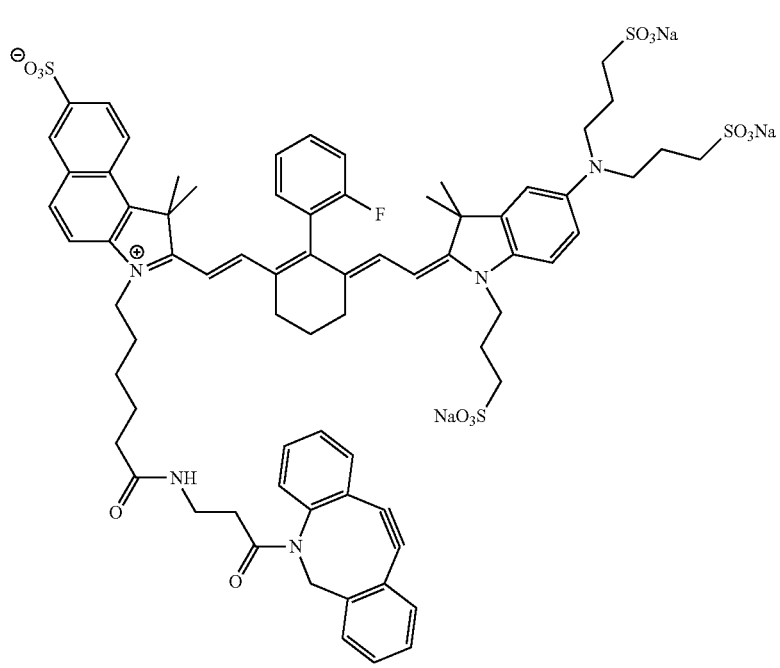

40

This compound was prepared in a manner similar to that used for 37 (Example 47) from the commercially available DBCO-Amine. To a solution of compound 25a (Example 25, 0.8 mg, $6.1\times10^{-4}$ mmol) and N,N-diisopropylethylamine (0.001 mL, $5.7\times10^{-3}$ mmol) in anhydrous dimethylsulfoxide (0.8 mL) was added DBCO-Amine (from Jena Bioscience, 0.5 mg, $1.8\times10^{-3}$ mmol) in one portion. The reaction was allowed to proceed at ambient temperature for 2 h, with periodic agitation at 15-min intervals. After HPLC analysis indicated complete consumption of 25a, the crude product was precipitated in anhydrous diethyl ether (10 mL). The ethereal supernatant was decanted and the precipitate was purified by prep-HPLC to afford the desired product 40 as a teal solid (0.8 mg, 90%). UV/Vis (acetonitrile/water=1:1) $\lambda_{max}$=790 nm; LRMS (ES/water), m/z calculated for $C_{73}H_{81}FN_5O_{14}S_4$ [M+H]$^+$ 1398.46, found 1398.5.

Example 51

Example 66 illustrates the synthesis of an azide-containing compound 25a derivative for click chemistry (Compound 25a-PEG-Azide, 41).

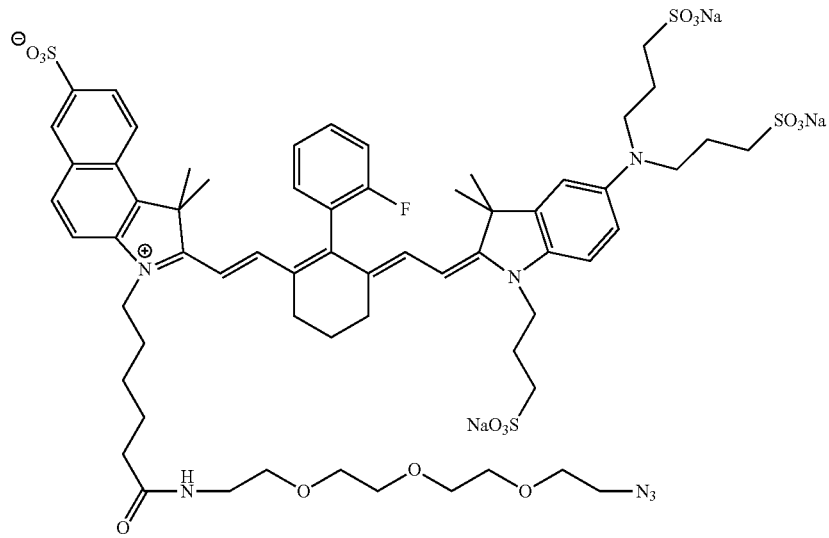

41

This compound was prepared in a manner similar to that used for 37 (Example 47) from commercially available 11-azido-3,6,9-trioxaundecan-1-amine. The exact yield was not determined. UV/Vis (acetonitrile/water=1:1) $\lambda_{max}$=790 nm; LRMS (ES/water), m/z calculated for $C_{63}H_{83}FN_7O_{16}S_4$ [M+H]' 1340.48, found 1340.5 and 671.0 [M+2H]$^{2+}$.

Example 52

Example 67 illustrates the click chemistry synthesis of a compound 25a dimer (42).

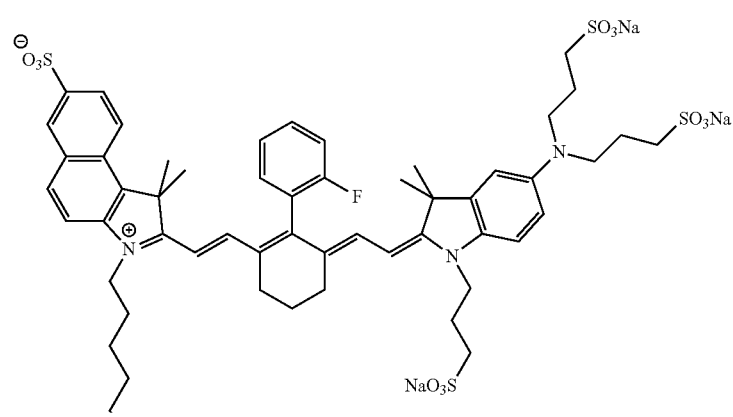

42

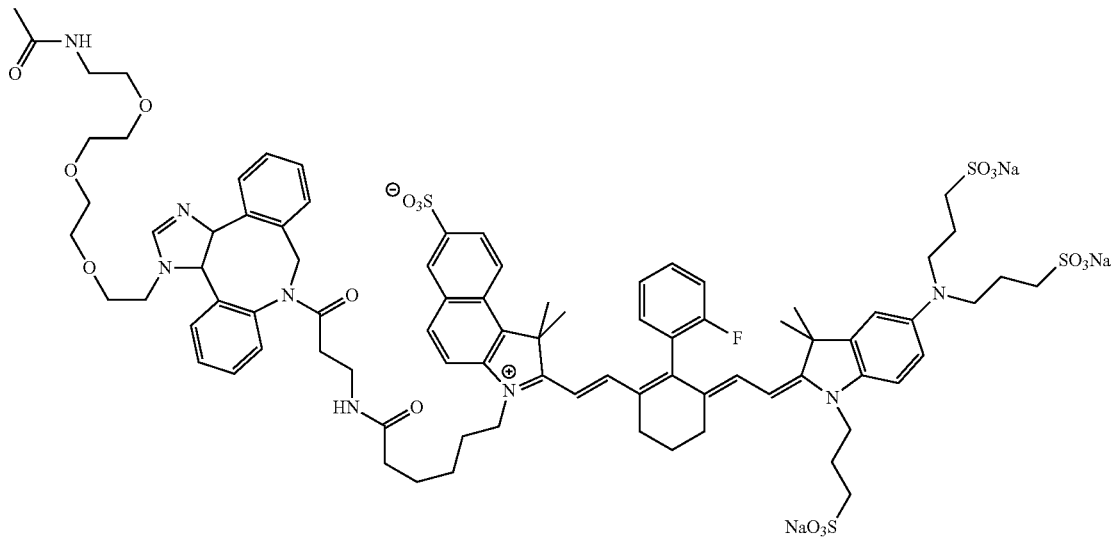

A solution of cycloalkyne 40 (100 μg, 6.8×10⁻² mop in water (100 μL) was mixed with a solution of azide 41 (6.8× 10⁻² μg, 7.1×10⁻² mol) in water (100 μL). The reaction mixture was agitated for 30 seconds and then allowed to proceed at ambient temperature for 2 hours. After HPLC analysis showed the complete consumption of 41, the reaction mixture was directly purified by reverse-phase HPLC to afford 42 as a blue solid. The exact yield was not determined. UV/Vis (acetonitrile/water=1:1) $\lambda_{max}$=789 nm; LRMS (ES/water), m/z calculated for $C_{136}H_{163}\beta 2N12O_{30}S8$ $[M+H]^+$ 2737.93, found 1368.7 $[M+2H]^{2+}$.

Example 53

Example 53 illustrates the click chemistry synthesis of an IRDye 800CW/compound 25a conjugate (800CW/Compound 25a Click Product 1, 58).

43

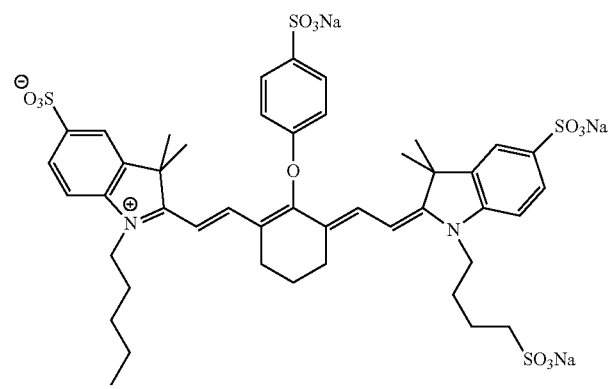

-continued

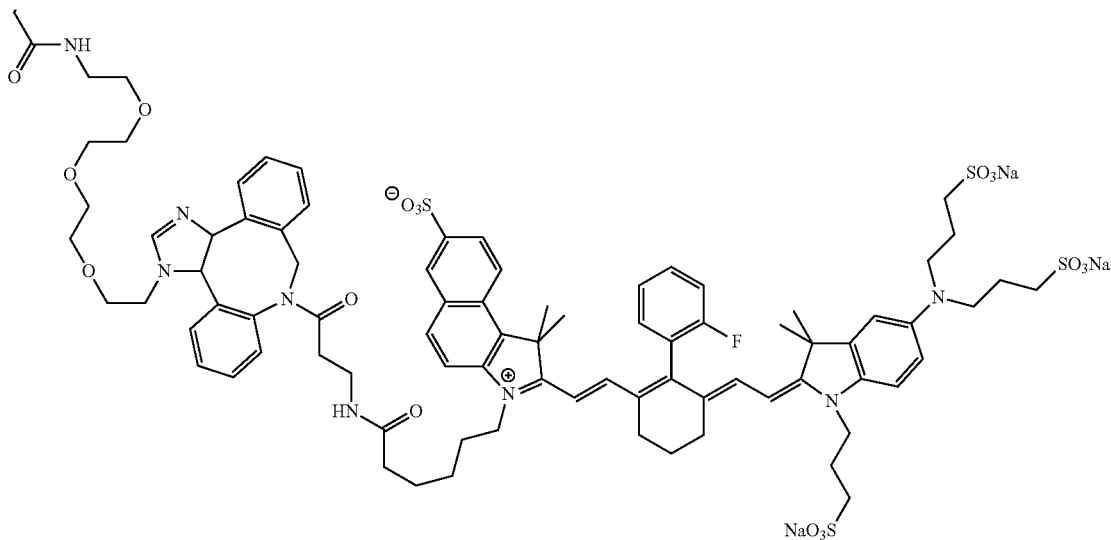

A solution of 40 (150 μg, 1.0×10⁻¹ mmol) in water (150 μL) was mixed with a solution of 800CW-PEG-Azide (29, Example 36) (63 μg, 5.0×10⁻² mmol) in water (50 μL). The reaction mixture was agitated for 30 seconds and then allowed to proceed at ambient temperature for 2 hours. After HPLC analysis showed the complete consumption of 40, the reaction mixture was directly purified by reverse-phase HPLC to afford the product 43 as a teal solid that was a mixture of the two triazole-cycloaddition regioisomers. The exact yield was not determined UV/Vis (acetonitrile/water=1:1) $\lambda_{max}1$=778 nm, $\lambda_{max}2$=830; LRMS (ES/water), m/z calculated for $C_{127}H_{151}FN_{11}O_{31}S_8$ [M+H]⁺2600.83, found 1299.6 [M−2H]²⁻.

Example 54

Example 54 illustrates the click chemistry synthesis of a second 800CW/QC-2 conjugate (800CW/Compound 25a Click Product 2, 44).

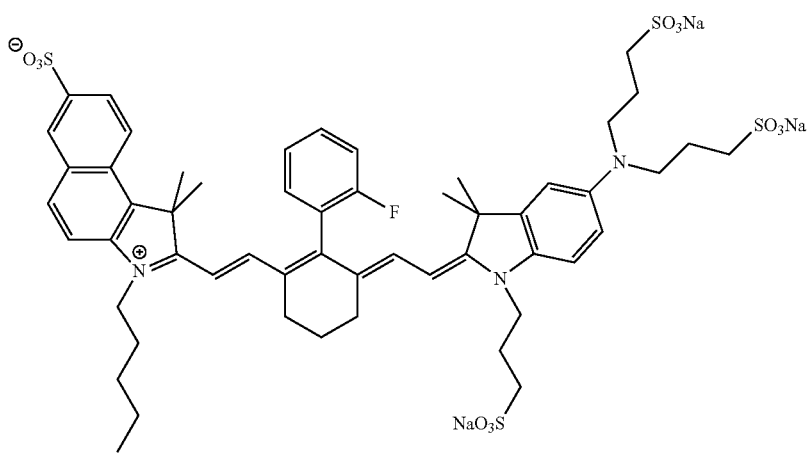

44

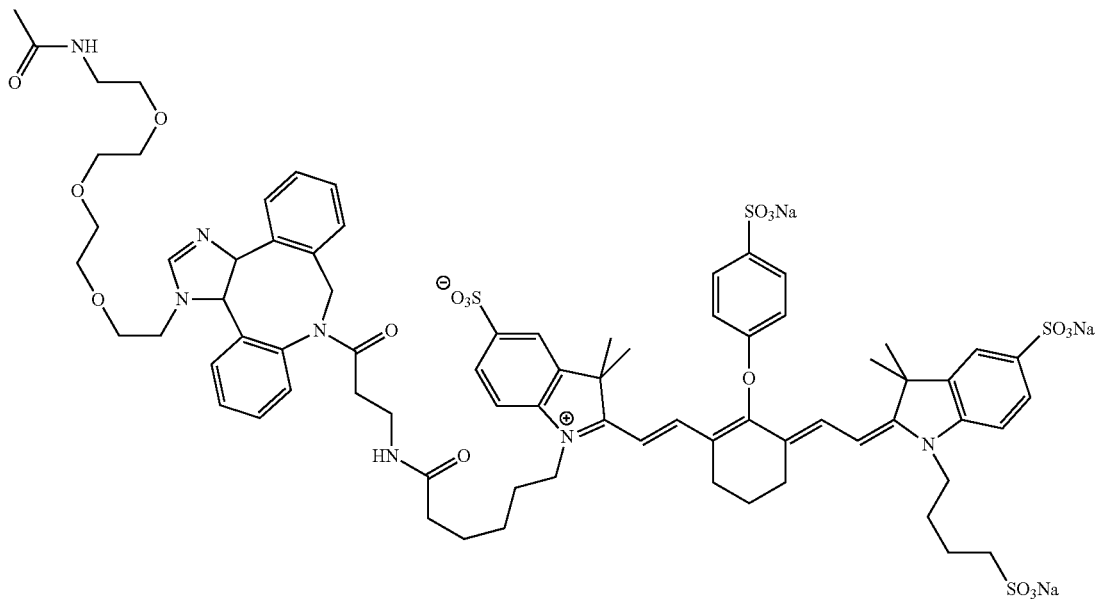

A solution of 41 (150 µg, 1.0×10⁻¹ µmol) in water (150 µL) was mixed with a solution of 800CW-DBCO (30. Example 37) (66 µg, 5.0×10⁻² µmol) in water (50 µL). The reaction mixture was agitated for 30 seconds and then allowed to proceed at ambient temperature for 2 hours. After HPLC analysis showed the complete consumption of starting material, the reaction mixture was directly purified by reverse-phase HPLC to afford the product 44 as a mixture of the two triazole cycloaddition regioisomers. UV/Vis (acetonitrile/water=1:1) $\lambda_{max}1$=778 nm, $\lambda_{max}2$=830 nm; LRMS (ES/water), m/z calculated for $C_{127}H_{151}FN_{11}O_{31}S_8$ [M+H]⁺ 2600.83, found #1300.1 [M−2H]²⁻.

Example 55

Example 55 illustrates a trityl-protected version of a sample heterocyclic dye (compound 10 from U.S. Provisional Patent Appl. No. 61/405,158) HETD (HETD-NH-(PEG)₂-NH-Trt, 45).

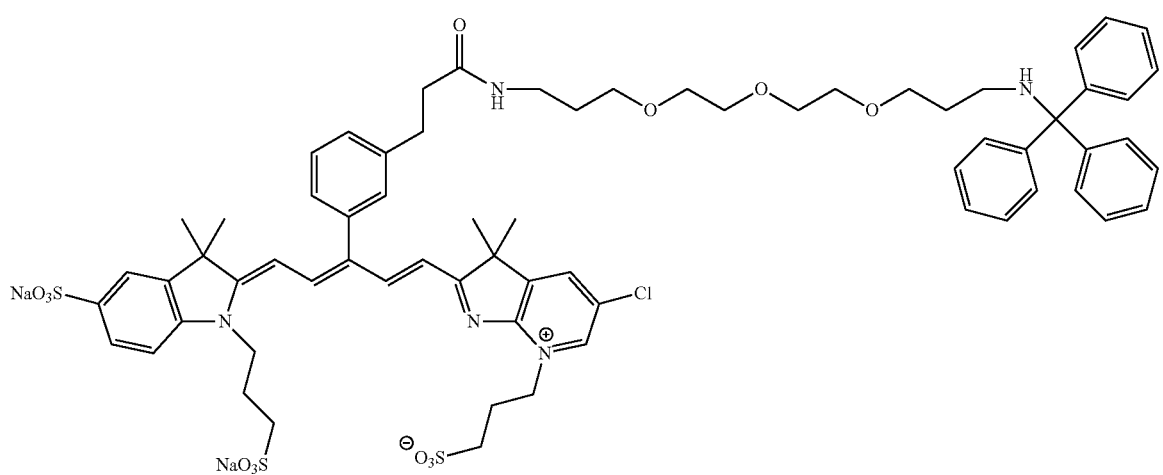

45

A solution of O-(N-trityl-3-aminopropyl)-O'-(3-aminopropyl)-diethyleneglycol (Trt-NH-PEG$_2$-NH$_2$, 1.0 mg, 2.2× $10^{-3}$ mmol) and N,N-diisopropylethylamine (0.001 mL, 5.7× $10^{-3}$ mmol) in anhydrous dimethyl sulfoxide (0.2 mL) was added to a reaction vessel containing HETD NHS ester (1.0 mg, 1.0×$10^{-3}$ mmol; compound 11 from U.S. Provisional Patent Appl. No. 61/405,158). The reaction was allowed to proceed at ambient temperature for 2 hours, with periodic vortexing at 15-minute intervals. After HPLC analysis showed complete consumption of HETD NHS ester, the reaction was precipitated into anhydrous diethyl ether. The ethereal layer was decanted and the crude product was purified by HPLC. Fractions containing the presumed HETD-NH-PEG$_2$-NH-Trt in ≥95% purity were combined and concentrated in vacuo to afford a blue film; the yield was presumed to be quantitative.

Example 56

Example 56 illustrates another derivative of HETD (HETD-NH-(PEG)$_2$-NH$_2$.2TFA, 46).

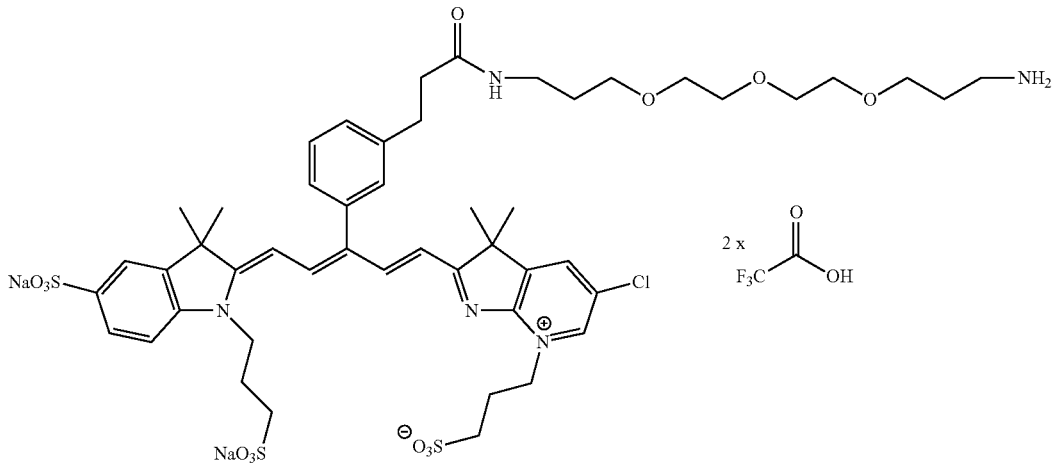

46

To a flask containing HETD-NH-PEG$_2$-NH-Trt (1.3 mg, 8.6×$10^{-4}$) was added a solution of trifluoroacetic acid in dichloromethane (TFA/CH$_2$Cl$_2$=1:3, 5.0 mL). The purple reaction was briefly swirled and allowed to proceed at ambient temperature for 30 minutes. The volatiles were removed in vacuo and the residuals were treated again with TFA/CH$_2$Cl$_2$ (1:3, 5.0 mL) for 30 minutes. After removing the volatiles in vacuo, the residuals were washed with anhydrous diethyl ether. The ethereal layer was decanted, and the product 46 was used without further purification; the yield was presumed to be quantitative. UV/Vis (methanol) $\lambda_{max}$=676 nm; LRMS (water) m/z calculated for 1064.4 [M+H]$^+$, found 1064.6, 532.9 [M+2H]$^{2+}$.

Example 57

Example 57 illustrates the synthesis of a phosphine HETD derivative (HETD-PEG-Phosphine, 47a).

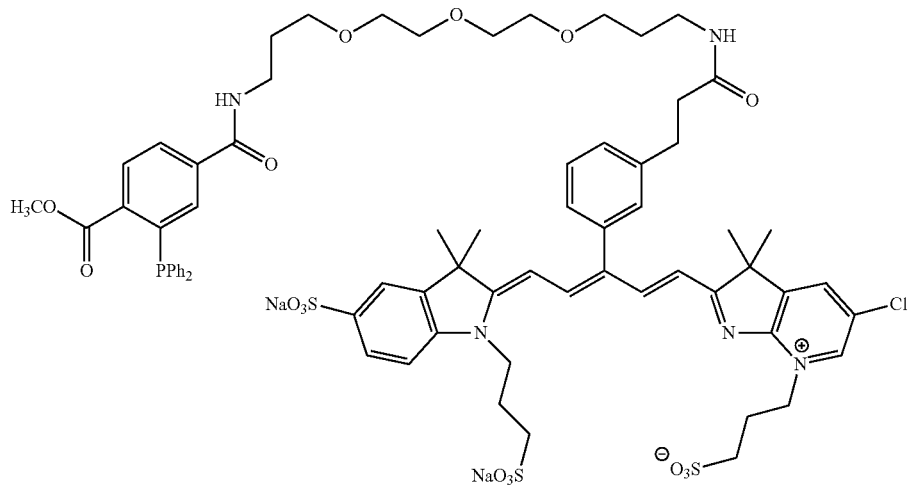

47a

To a solution of HETD-NH-(PEG)$_2$-NH$_2$.2TFA (1.3 mg, 1.0×10$^{-3}$ mmol) in anhydrous dimethyl sulfoxide (0.2 mL) was added NHS-Phosphine (1.0 mg, 2.2×10$^{-3}$ mmol, ThermoScientific/Pierce) followed by N,N-diisopropylethylamine (0.001 mL, 5.7×10$^{-3}$ mmol). The reaction was allowed to proceed at ambient temperature for 2 hours, with periodic agitation at 15-minute intervals. After HPLC analysis showed near-complete consumption of the HETD-NH-(PEG)$_2$-NH$_2$.2TFA, the reaction was precipitated into anhydrous diethyl ether. The ethereal layer was decanted and the crude product was purified by HPLC. Fractions containing the presumed HETD-PEG-Phosphine in ≥95% purity were combined and concentrated in vacuo to afford a blue solid (0.7 mg, 51% based on HETD-NH-(PEG)$_2$-NH$_2$.2TFA); UV-Vis (methanol) $\lambda_{max}$=676 nm; LRMS (water) m/z calculated for 1410.4 [M+H]$^+$, found 705.8 [M+2H]$^{2+}$.

Example 58

Example 58 illustrates a phosphine oxide HETD derivative (HETD-PEG-Phosphine Oxide, 47b).

This compound was isolated as a substantial byproduct from the synthesis of HETD-PEG-Phosphine (47a). This byproduct is nonfunctional and causes background problems. The compound is a blue solid (0.2 mg, 18% based HETD-NH-(PEG)$_2$-NH$_2$.2TFA); UV-Vis (methanol) $\lambda_{max}$=676 nm; LRMS (water) m/z calculated for 1426.4 [M+H]$^+$, found 1426.5, 713.9 [M+2H]$^{2+}$.

Example 59

Example 59 illustrates the click chemistry synthesis of an IRDye®HETD/Compound 25a conjugate (HETD-Compound 25a Click Product, 48).

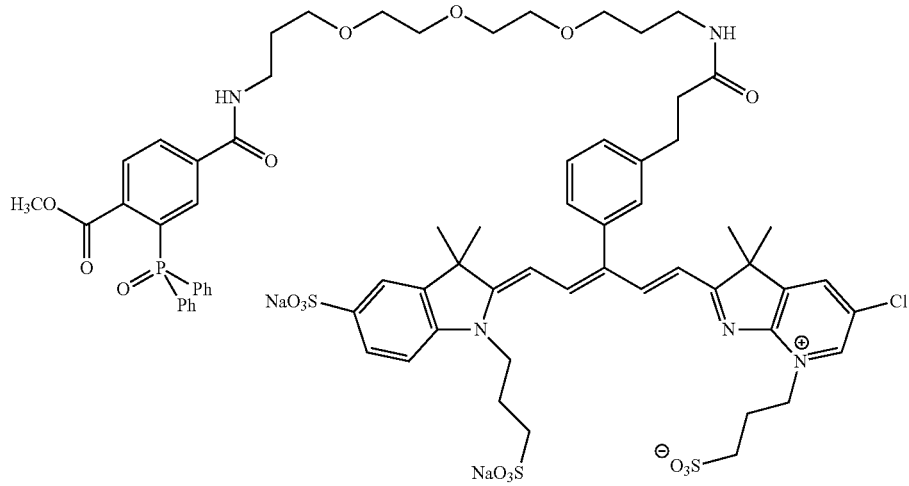

47b

48

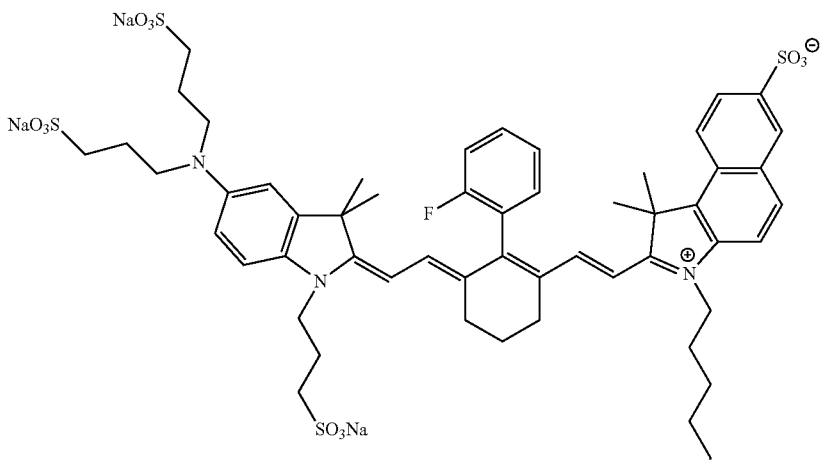

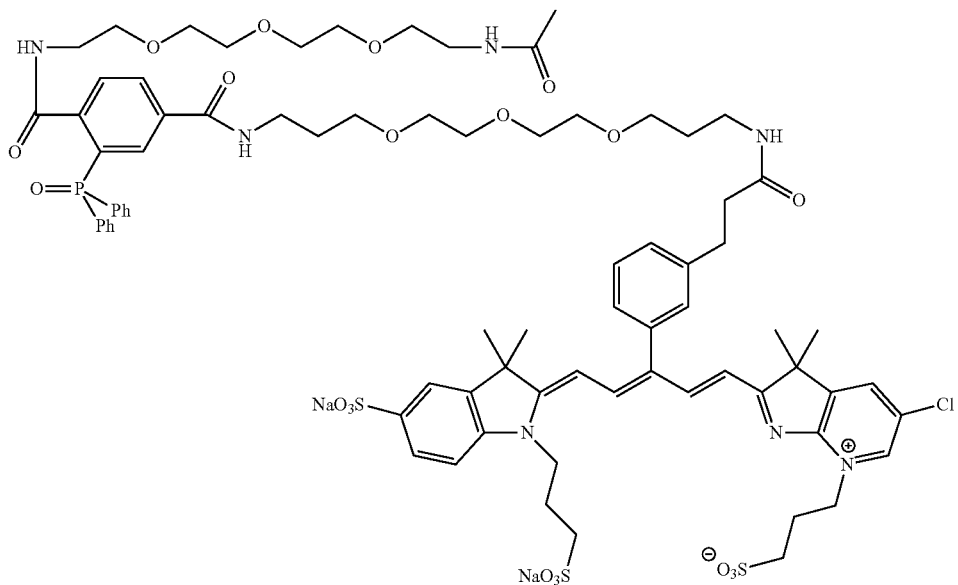

To a solution of azide 41 (150 μg, 1.1×10⁻¹ mmol) in water (150 μL) was added a solution of HETD-PEG-Phosphine (47a) (92 μg, 6.3×10⁻² μmol) in water (50 μL). The reaction was allowed to proceed at ambient temperature for 1 hour, then maintained at 40° C. for 3 hours. After HPLC analysis showed complete consumption of HETD-PEG-Phosphine, the reaction mixture was filtered and directly purified by HPLC. Fractions containing the presumed HETD-Compound 25a Click Product 48 were combined and concentrated in vacuo. The exact yield was not determined. UV/Vis (acetonitrile/water=1:1) $\lambda_{max}1$=778 nm, $\lambda_{max}2$=677 nm; LRMS (ES/water), m/z calculated for $C_{123}H_{150}ClN_9O_{33}PS_7$ [M+H]⁺2570.8, found 858.5 [M+3H]³⁺.

Example 60

Example 6 illustrates the synthesis of the fluorescence-quenching dye sodium (E)-2-((E)-2-(3-((E)-2-(5-(bis(3-sulfonatopropyl)amino)-3,3-dimethyl-1-(3-sulfonatopropyl)-3H-indolium-2-yl)vinyl)-5-carboxy-2-(2-fluorophenyl)cyclohex-2-enylidene)ethylidene)-1,1-dimethyl-3-(3-sulfonatopropyl)-2,3-dihydro-1H-benzo[e]indole-6,8-disulfonate (49).

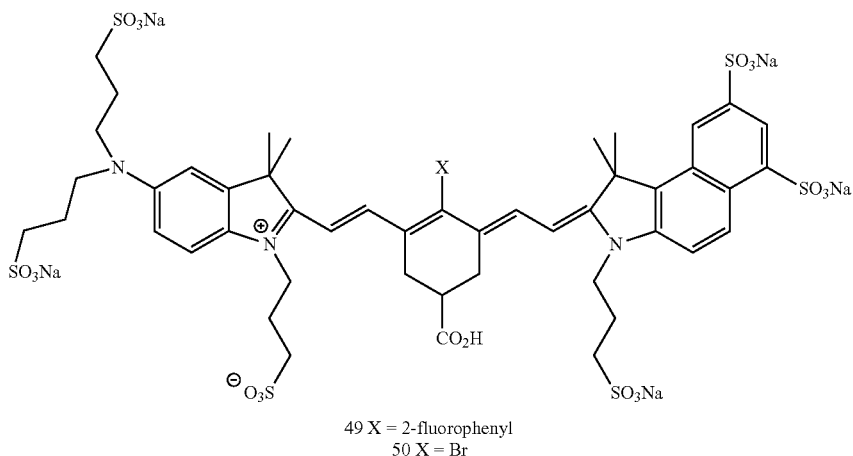

49 X = 2-fluorophenyl
50 X = Br

Compound 49 was prepared by combining 200 mg of compound 50, 31 mg of 2-fluorophenylboronic acid, 12.7 mg of Pd(PPh$_3$)$_4$, 36.1 mg of sodium acetate, 800 μL of 2-methoxyethanol, and 8 mL of water. The mixture was heated at reflux for 45 minutes under a nitrogen atmosphere. To the reaction was then added 1 mL of 10% sulfuric acid solution and reflux was continued for 90 minutes. The compound was purified by reverse-phase C18 chromatography using acetonitrile/water, yielding 13 0 mg of blue-green product. Absorbance: $\lambda_{Water}$=779 nm.

Compound 51 was prepared by combining 130 mg of compound 49, 72 mg of N,N'-disuccinimidyl carbonate, 25 μL of N,N-diisopropylethylamine, and 8 mL of DMSO. The mixture was sonicated at room temperature for 120 minutes, precipitated into diethyl ether, and then purified by reverse-phase C18 chromatography using acetonitrile/water, yielding 80 mg of blue-green product.

Example 61

Example 61 illustrates the synthesis of an NHS ester of compound 49 (51).

Example 62

Example 62 illustrates the synthesis of an IRDye 800CW/Compound 64 conjugate (IRDye 800CW-NH-(PEG)$_2$-NH-Compound 64, 15-atom linker; 52).

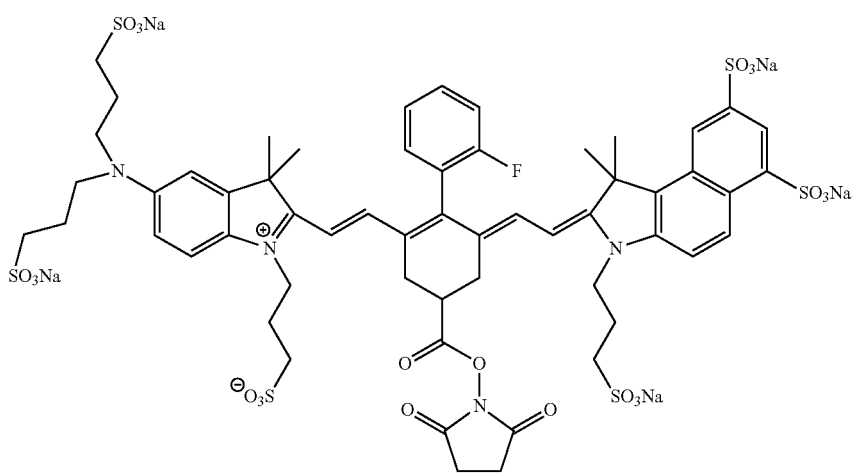

51

52

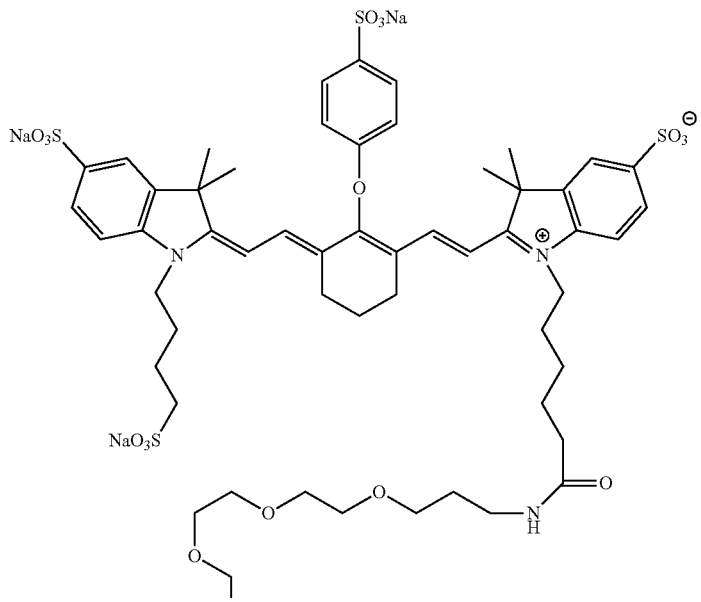

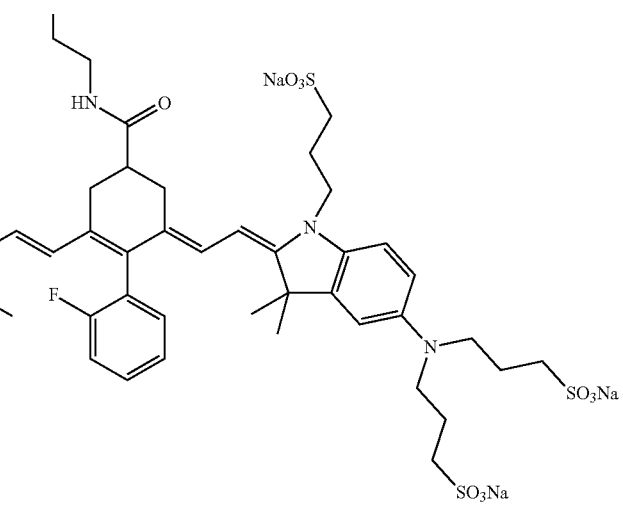

A solution of IRDye 800CW-(PEG)$_2$-NH$_2$.TFA salt (32, Example 39) (69 μg, 5.0×10$^{-2}$ μmol) and N,N-diisopropylethylamine (0.1 μL, 5.7×10$^{-1}$ μmol) in anhydrous dimethyl sulfoxide (200 μL) was added to a vessel containing compound 51 (100 μg, 7.3×10$^{-2}$ μmol). The reaction mixture was agitated for 30 seconds and then allowed to proceed at ambient temperature for 2 hours. After HPLC analysis showed the complete consumption of the IRDye 800CW-(PEG)$_2$-NH$_2$.TFA salt, the reaction mixture was precipitated into dry diethyl ether. The ethereal layer was decanted and the crude product residue was purified by reverse-phase HPLC to afford the product 52 as a teal solid. The exact yield was not determined. UV/Vis (acetonitrile/water=1:1) $\lambda_{max}1$=778 nm, $\lambda_{max}2$=830 nm; LRMS (ES/water), m/z calculated for C$_{109}$H$_{137}$FN$_7$O$_{36}$S$_{10}$ [M+H]$^+$2458.62, found 820.8 [M+3H]$^{3+}$.

Example 63

Example 63 illustrates the synthesis of another IRDye 800CW/compound 49 conjugate (IRDye 800CW-NH-dPEG$_{11}$-NH-Compound 49, 37-atom linker; 53).

53

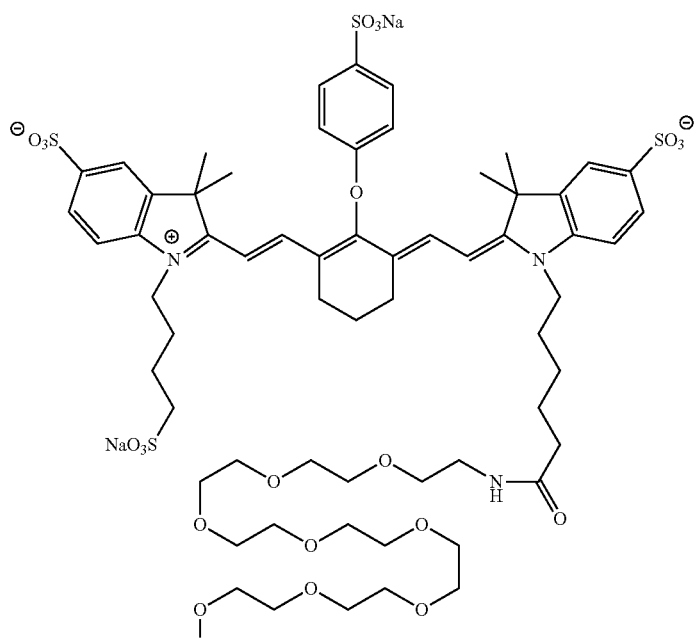

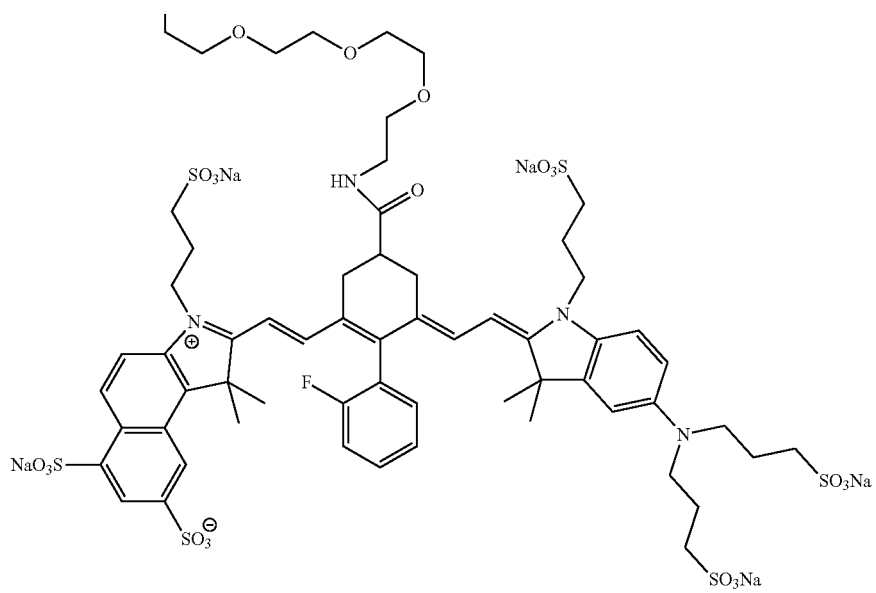

This compound was prepared in a manner similar to 39 (Example 49) from the corresponding IRDye 800CW-NH-dPEG₁₁®—NH₂.TFA, which was prepared by a method analogous to 32 (Example 39) from Boc-NH-dPEG₁₁®—NH₂ (Quanta Biodesign, Inc.). The exact yield was not determined. UV/Vis (acetonitrile/water=1:1) $\lambda_{max}1$=777 nm, $\lambda_{max}2$=829 nm; LRMS (ES/water), m/z calculated for $C_{123}H_{165}FN_7O_{44}S_{10}$ [M+H]⁺2782.80, found 928.5 [M+3H]³⁺.

Example 64

Example 64 illustrates the synthesis of a strained cycloalkyne-containing compound 49 derivative for click chemistry (Compound 49-DBCO; 54).

54

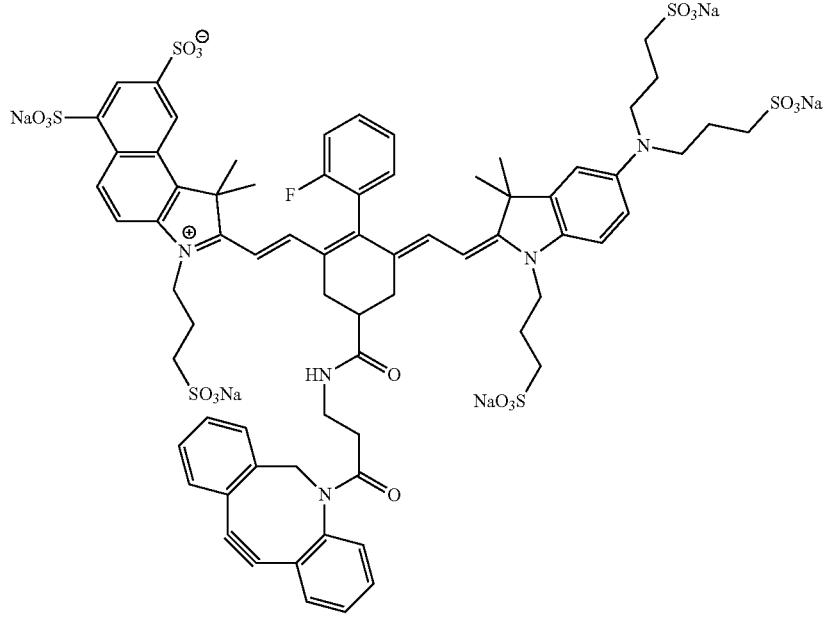

This compound was prepared in a manner similar to that used for 40 (Example 50) from the commercially available DBCO-Amine. The exact yield was not determined. UV/Vis (acetonitrile/water=1:1) $\lambda_{max}$=799 nm; LRMS (ES/water), m/z calculated for $C_{71}H_{77}FN_5O_{20}S_6$ [M+H]$^+$1530.34, found 765.9 [M+2H]$^{2+}$.

Example 65

Example 65 illustrates the synthesis of an azide-containing a compound 49 derivative for click chemistry (Compound 49-PEG-Azide, 55).

This compound was prepared in a manner similar to that used for 41 (Example 51) from commercially available 11-azido-3,6,9-trioxaundecan-1-amine. The exact yield was not determined UV/Vis (acetonitrile/water=1:1) $\lambda_{max}$=799 nm.; LRMS (ES/water), m/z calculated for $C_{61}H_{79}FN_7O_{22}S_6$ [M+H]$^+$1472.35, found 736.9 [M+2H]$^{2+}$.

Example 66

Example 66 illustrates the synthesis of an IRDye 800CW/ compound 49 conjugate (IRDye 800CW/Compound 49 Click Product 1; 56).

55

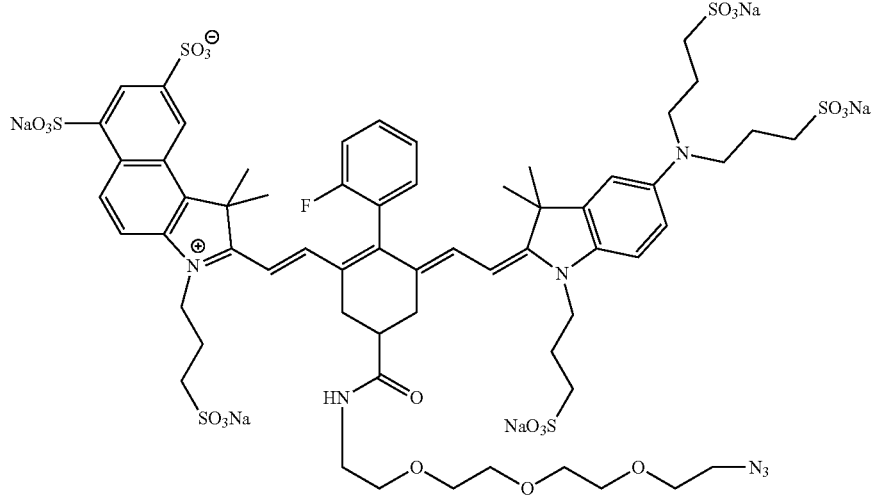

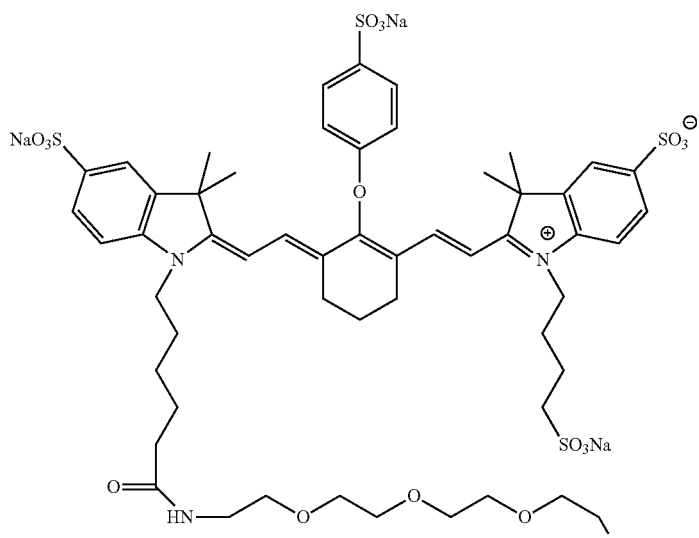

56

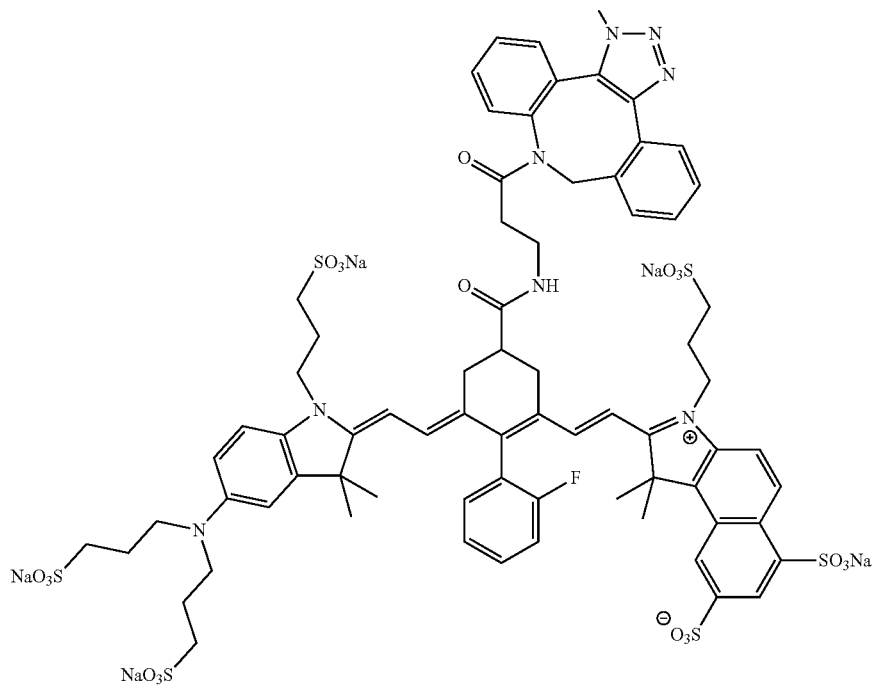

This compound was prepared in a manner similar to that used for 43 (Example 53) from cycloalkyne 54 and IRDye 800CW-PEG-Azide 29 (Example 36). The exact yield was not determined, and the compound was a mixture of the two cycloaddition regioisomers. UV/Vis (acetonitrile/water=1:1) $\lambda_{max}1$=778 nm, $\lambda_n$, $\lambda_{max}2$=830 nm; LRMS (ES/water), m/z calculated for $C_{125}H_{147}FN_{11}O_{37}S_{10}$ $[M+H]^+$2732.71, found 912.2 $[M+3H]^{3+}$, 1365.6 $[M-2H]^{2-}$, 910.4 $[M-3H]^{3-}$.

Example 67

Example 82 illustrates the synthesis of an IRDye 800CW/ compound 49 conjugate (IRDye 800CW/Compound 64 Click Product 2; 57).

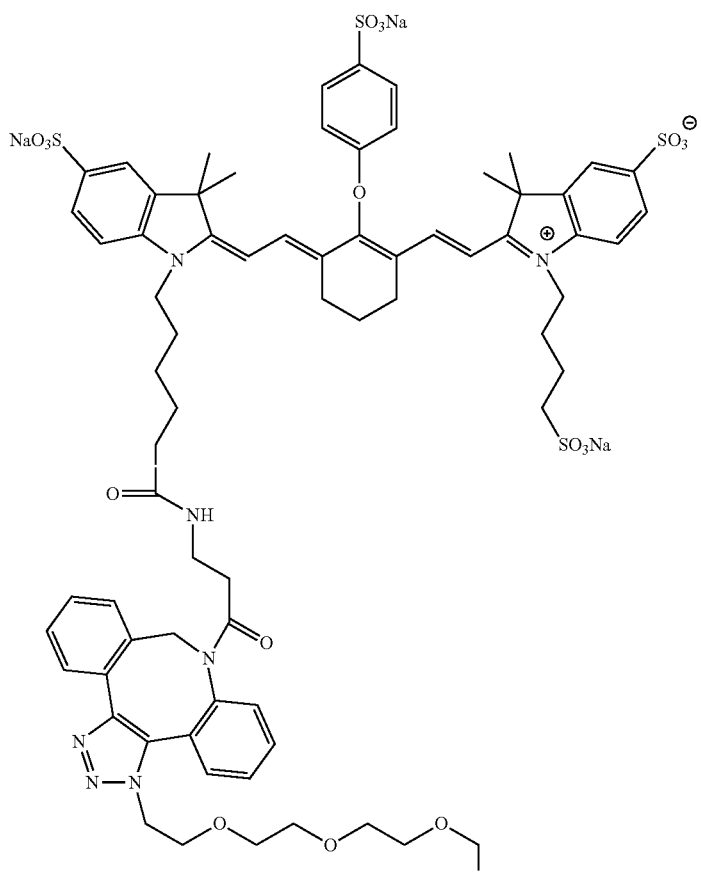

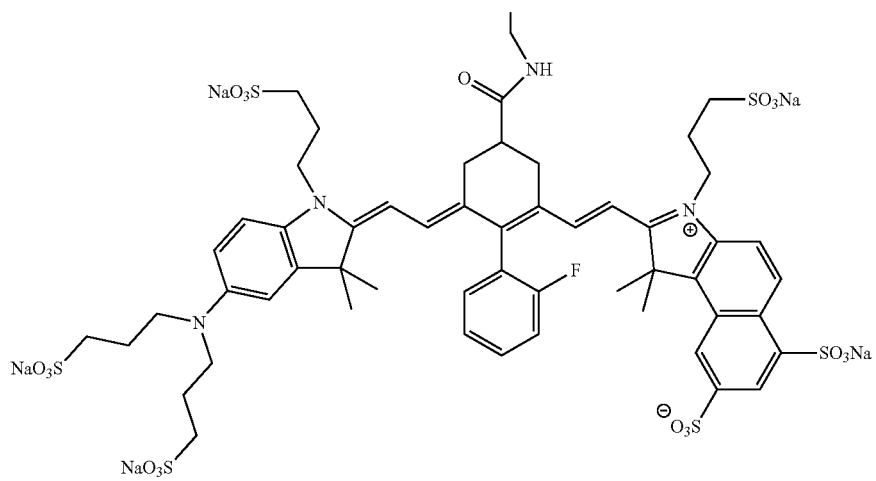

This compound was prepared in a manner similar to that used for 43 (Example 53) from Compound 64-PEG-Azide (55, Example 65) and IRDye 800CW-DBCO (29, Example 36). The exact yield was not determined, and the compound was a mixture of the two cycloaddition regioisomers. UV/Vis (acetonitrile/water=1:1) $\lambda_{max}1$=778 nm, $\lambda_{max}2$=830 nm; LRMS (ES/water), m/z calculated for $C_{125}H_{47}F_{11}O_{37}S10$ $[M+H]^+$ 2732.71, found 1367.6 $[M+2H]^{2+}$, 912.2 $[M+3H]^{3+}$, 1365.6 $[M-2H]^{2-}$, 910.4 $[M-3H]^{3-}$.

Example 68

Example 68 illustrates the synthesis of an strained cycloalkyne-containing HETD derivative for click chemistry (HETD-DBCO, 58).

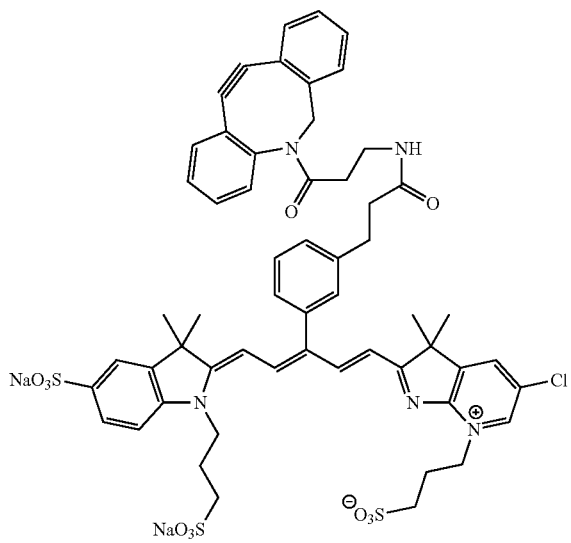

58

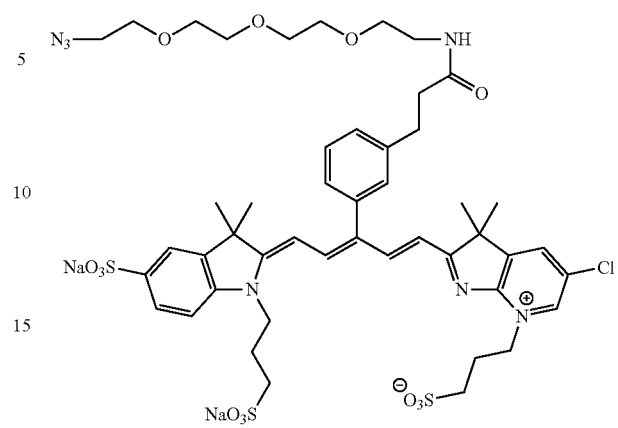

59

This compound was prepared in a manner similar to that used for compound 40 (Example 50) from the commercially available DBCO-Amine. The exact yield was not determined. UV/Vis (acetonitrile/water=1:1) $\lambda_{max}$=676 nm; UV/Vis (acetonitrile/water=1:1) $\lambda_{max}$=676 nm; LRMS (ES/water), m/z calculated for $C_{57}H_{59}ClN_5O_{11}S_3$ $[M+H]^+$1120.30, found 1120.6. 560.9 $[M+2H]^{2+}$.

This compound was prepared in a manner similar to that used for 41 (Example 55) from the commercially available 11-azido-3,6,9-trioxaundecan-1-amine. The exact yield was not determined. UV/Vis (acetonitrile/water=1:1) $\lambda_{max}$=676 nm; LRMS (ES/water), m/z calculated for $C_{47}H_{61}ClN_7O_{13}S_3$ $[M+H]^+$1062.31, found 1060.6 $[M-H]^-$, 1082.6 $[M+Na-2H]^{2-}$.

Example 69

Example 69 illustrates the synthesis of an azide-containing HETD derivative for click chemistry (HETD-PEG-Azide, 59).

Example 70

Example 70 illustrates the synthesis of a HETD/compound 49 conjugate (HETD/Compound 49 Click Product 1; 60).

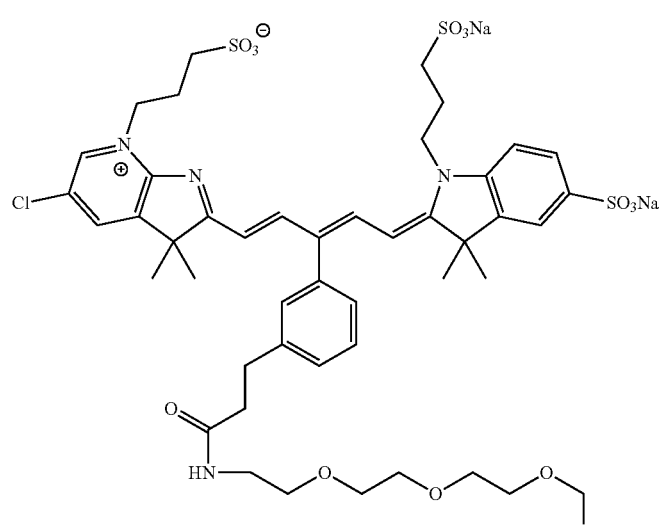

60

-continued

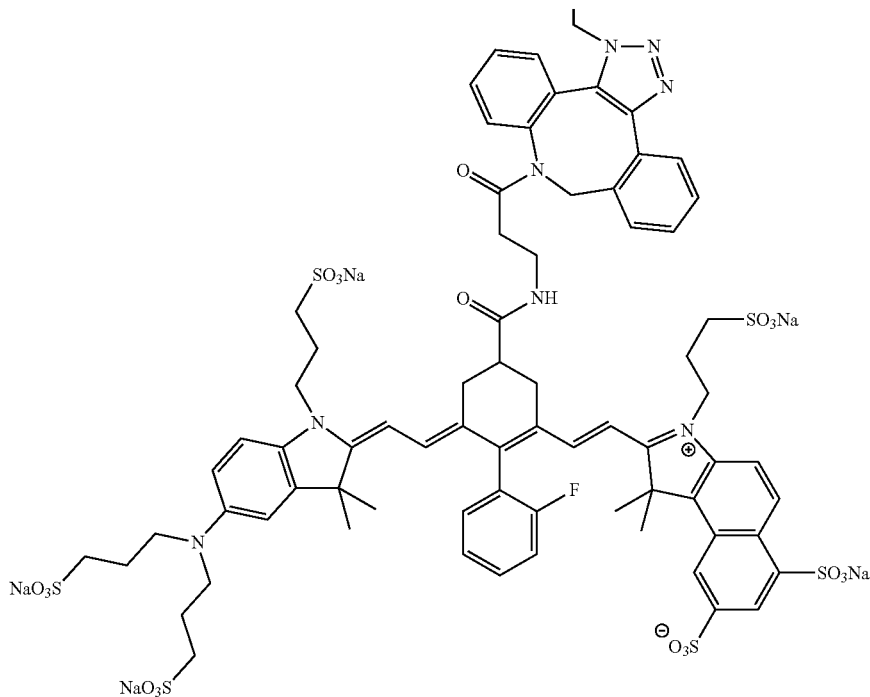

This compound was prepared in a manner similar to that used for compound 43 (Example 53) from Compound 49-DBCO (54) (Example 64) and HETD-PEG-Azide (59) (Example 69). The exact yield was not determined, and the compound was a mixture of the two cycloaddition regioisomers. UV/Vis (acetonitrile/water=1:1) $\lambda_{max}1$=679 nm, $\lambda_{max}2$=799 nm; LRMS (ES/water), m/z calculated for $C_{118}H_{137}ClFN_{12}O_{33}S_9$ $[M+H]^+$2591.65. found 1295.0 $[M-2H]^{2-}$, 863.1 $[M-3H]^{3-}$, Example 71

Example 71 illustrates the synthesis of another HETD/compound 49 conjugate (HETD/Compound 49 Click Product 2; 61).

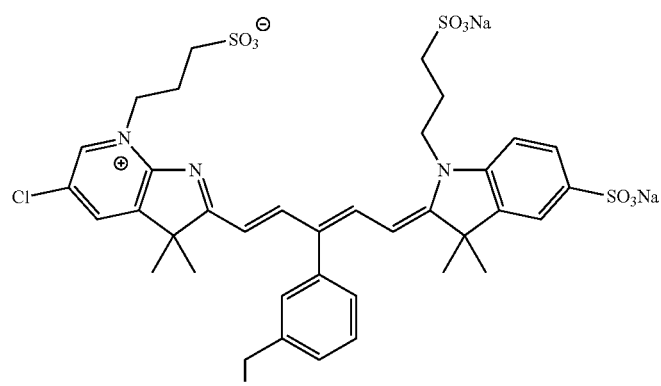

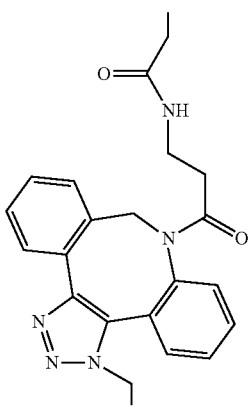

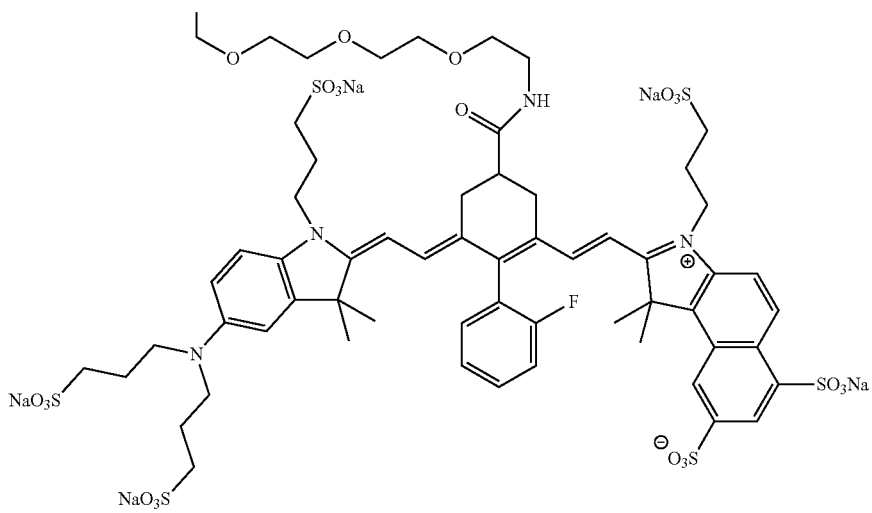

This compound was prepared in a manner similar to that used for 43 (Example 53) from Compound 49-PEG-Azide (55, Example 65) and HETD-DBCO (58, Example 68). The exact yield was not determined, and the compound was a mixture of the two cycloaddition regioisomers. UV/Vis (acetonitrile/water=1:1) $\lambda_{max}1$=679 nm, $\lambda_{max}2$=799 nm; LRMS (ES/water), m/z calculated for $C_{118}H_{137}ClFN_{12}O_{33}S_9$ $[M+H]^+$2591.65, found 1295.6 $[M-2H]^{2-}$.

Example 72

Objective: For some dye scaffolds, the final Suzuki coupling step to install a 2,4,6-trifluorophenyl polyene substituent has a low chemical yield (~10%). In this experiment, the yields and properties of additional polyene substituents were evaluated.

Design Principle: We analyzed the properties of a dye scaffold and related compounds and the corresponding substitution effects on the excitation and emission wavelengths. The small size of fluorine is unlikely to produce steric effects, therefore, we explored the electronic effects of fluorine and related substitutions. The Hammett equation (σ-value) is an important tool to understand the electronic effects of the substituents, therefore, we explored the correlation of the wavelength ($\lambda_{MeOH}$) and the σ-value (vide infra):

62a-m

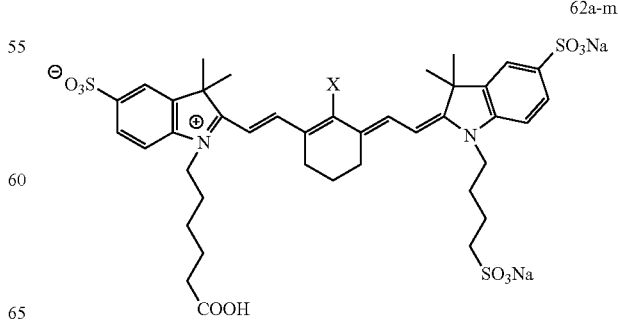

TABLE 5

Absorption (λ) and σ- Value for Related Dyes

| X | $\lambda_{MeOH}$ (nM) | σ | X | $\lambda_{MeOH}$ (nM) | σ |
|---|---|---|---|---|---|
| H, H, H (62a) | 766 | | COOH, F, F (62f) | 782 | $\sigma_{o(F)} = 0.24$<br>$\sigma_{o(F)} = 0.24$<br>$\sigma_{p(COOH)} = \cdots$ |
| F (62b) | 772 | $\sigma_{o(F)} = 0.24$ | Cl, Cl (62g) | 782 | $\sigma_{o(Cl)} = 0.2$<br>$\sigma_{o(Cl)} = 0.2$ |
| F, F (62c) | 782 | $\sigma_{o(F)} = 0.24$<br>$\sigma_{o(F)} = 0.24$ | OMe, F, F (62h) | 772 | $\sigma_{o(F)} = 0.24$<br>$\sigma_{o(F)} = 0.24$<br>$\sigma_{p(OMe)} = -0.27$ |
| F, F, F (62d) | 785 | $\sigma_{o(F)} = 0.24$<br>$\sigma_{o(F)} = 0.24$<br>$\sigma_{p(F)} = 0.06$ | O-nBu, F, F (62i) | 779 | $\sigma_{o(F)} = 0.24$<br>$\sigma_{o(F)} = 0.24$<br>$\sigma_{m(-O-nBu)} = 0.10$ |

TABLE 5-continued

Absorption (λ) and σ- Value for Related Dyes

| X | $\lambda_{MeOH}$ (nM) | σ | X | $\lambda_{MeOH}$ (nM) | σ |
|---|---|---|---|---|---|
| 62e | 789 | $\sigma_{o(F)} = 0.24$<br>$\sigma_{o(F)} = 0.24$<br>$\sigma_{p(F)} = 0.06$<br>$\sigma_{m(-O-Bu)} = 0.10$ | 62j | 790 | $\sigma_{o(F)} = 0.24$<br>$\sigma_{m(F)} = 0.34$<br>$\sigma_{m(-O-nBu)} = -0.24$ |

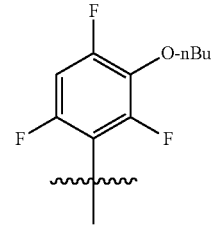

The above mentioned examples indicate that the electronic effects play a major role in the corresponding dye's optical properties and a correlation between the wavelength ($\lambda_{MeOH}$) and the σ-value can be made. Therefore, a low yielding Suzuki coupling step can be circumvented by replacing 2,4, 6-trifluoro-substitution with 2,3-difluoro substitution only, as both substitution patterns should lead to similar electronic effects. The detailed synthetic protocol and optical properties are discussed below.

To a 100-mL pressure tube with a magnetic stir-bar were added the chloro-precursor dye (62m) (208 mg, 0.218 mmol), 2,3-difluorophenyl boronic acid (84.8 mg, 0.537 mmol), tetrakis(triphenylphosphine)palladium(0) (23.2 mg, 0.0221 mmol), sodium acetate (75.3 mg, 0.918 mmol), ultra-pure water (6 mL) and 2-methoxyethanol (1 mL). The pressure tube was purged with argon for 2 min and was heated at 115° C. for 1 h. The reaction mixture was cooled down to ambient temp. and the solvent was removed under reduced pressure.

TABLE 6

Summary of Photophysical Properties

| X = | Abs Max PBS/ Methanol | $Em_{Max}$ PBS | Fl Intensity of X / Fl Intensity of 800 CW (0.1 μM solutions in 1XPBS) | | Quantum $Yield_{Smd}$ = IRDye 800 CW (QY = 0.07) |
|---|---|---|---|---|---|
| | | | Fluorimeter | Odyssey | |
| 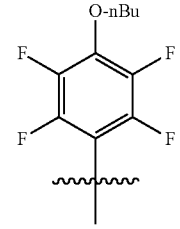 62k | 773 nm/ 781 nm | 790 nm | 100% | 104% | 0.060 |
| N/A (IRDye IRDye 800 CW) | 775 nm (in PBS only) | 790 nm | 100% | 100% | 0.07 |

Synthesis of 2,3-Difluorophenyl Dye (62k)

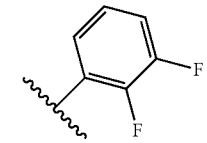 [SMILES: *c1cccc(F)c1F]

62k X = 2,3-difluorophenyl
62m X = Cl

The reaction mixture was triturated with methylene chloride (50 mL), and the product 62k was purified on C18 reverse-phase silica using water:acetonitrile as the eluent (66.5%, 99.3% HPLC purity at 780 nm); mass. spec. obs. 965.6, expected 965.2.

In an alternative version of the procedure, to a 100-mL pressure tube with a magnetic stir-bar were added the chloro dye (62m) (207 mg, 0.223 mmol), 2,3-difluorophenyl boronic acid (107 mg, 0.675 mmol), tetrakis(triphenylphosphine)-palladium(0) (24.9 mg, 0.0215 mmol), sodium acetate (55.4 mg, 0.675 mmol), ultra-pure water (6 mL) and 2-methoxy-ethanol (1 mL). The pressure tube was purged with argon for 2 min and was heated at 115° C. for 45 min. The reaction mixture was cooled down to ambient temp. and the solvent was removed under reduced pressure. The reaction mixture was triturated with methylene chloride (50 mL), and the product 62k was purified on C18 reverse-phase silica using water: acetonitrile as eluent.

Example 73

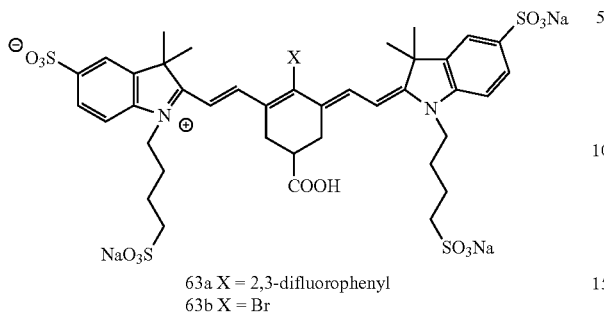

63a X = 2,3-difluorophenyl
63b X = Br

Compound 63a was prepared by adding compound 63b (434.0 mg, 0.4060 mmol; which can be prepared from compounds 2 and 6 by the method of Example 7, follow by ester hydrolysis by a conventional method) to an oven-dried pressure tube with a magnetic stir-bar with 2,3-difluorophenylboronic acid (102.0 mg, 0.6460 mmol), sodium acetate (80.0 mg, 0.646 mmol), tetrakis triphenyl phosphine palladium(0) (45.0 mg, 39.0 μmol), water (12 mL) and methoxymethanol (2 mL). The pressure tube was purged with nitrogen before heating the mixture at 115° C. for 2 h. The reaction mixture was neutralized with 1(N) hydrochloric acid (2404). After HPLC analysis showed complete consumption of the presumed mixed carbonate intermediate, the reaction mixture was concentrated in vacuo to afford a crude residue. The reaction mixture was triturated the crude dye with 25 mL of dichloromethane. The dichloromethane layer was removed and the residue was purified by reverse-phase flash chromatography to furnish the desired product63 as a green solid (306.3 mg, 75%). UV/Vis (methanol) λmax=770 nm; LRMS (ES/acetonitrile), m/z calculated for $C_{45}H_{50}F_2N_2O_{14}S_4$ [M+H]$^+$1009.3, found 1009.2.

Example 74

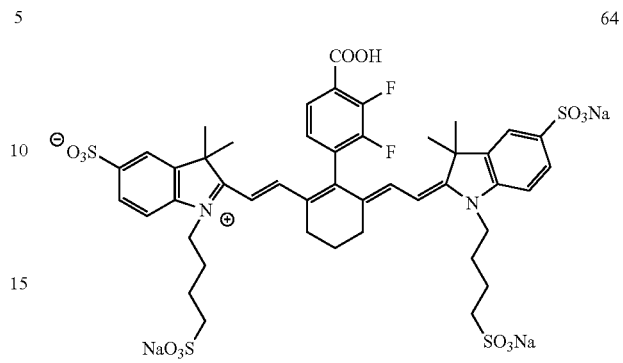

Compound 64 was prepared by adding compound 62m (387.1 mg, 0.4060 mmol) to an oven-dried pressure tube with a magnetic stir-bar with, 1-carboxyl 2,3-difluoro boronic acid (130.4 mg, 0.6460 mmol), sodium acetate (80.0 mg, 0.646 mmol), tetrakis triphenyl phosphine palladium(0) (45.0 mg, 39 μmol), water (12 mL) and methoxymethanol (2 mL). The pressure tube was purged with nitrogen before heating the mixture at 115° C. for 2 h. The reaction mixture was neutralized with 1 N hydrochloric acid (240 μL). After HPLC analysis showed complete consumption of the presumed mixed carbonate intermediate, the reaction mixture was concentrated in vacuo to afford a crude residue. The reaction mixture was triturated the crude dye with 25 mL of dichloromethane. The dichloromethane layer was removed and the residue was purified by reverse-phase flash chromatography to furnish the desired product 6 as a green solid (294 mg, 72%). UV/Vis (methanol) $\lambda_{max=}$772 nm; LRMS (ES/acetonitrile), m/z calculated for $C_{45}H_{50}F_2N_2O_{14}S4$ [M+H]$^+$ 1009.6, found 1009.4.

Example 75

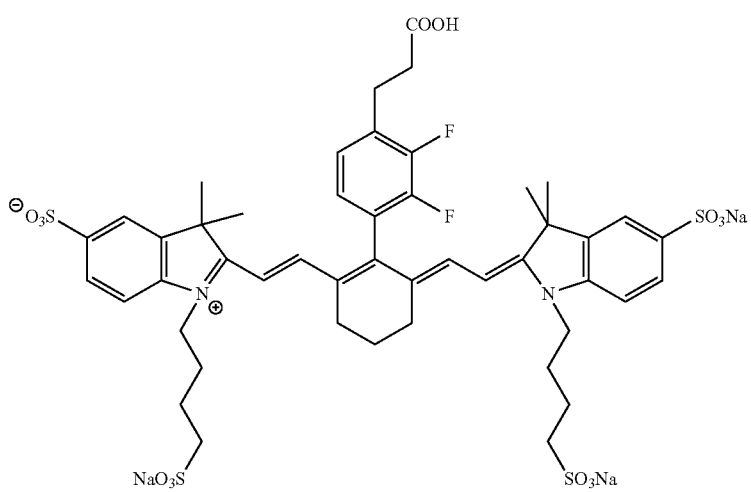

Compound 65 was prepared by adding compound 62 m (387.1 mg, 0.4060 mmol) to an oven-dried pressure tube with a magnetic stir-bar with boronic acid (148.6 mg, 0.6460 mmol), sodium acetate (80.0 mg, 0.646 mmol), tetrakis triphenyl phosphine palladium(0) (45.0 mg, 39 mmol), water (12 mL) and methoxymethanol (2 mL). The pressure tube was purged with nitrogen before heating the mixture at 115° C. for 2 h. The reaction mixture was neutralized with 1 N hydrochloric acid (240 µL). After HPLC analysis showed complete consumption of the presumed mixed carbonate intermediate, the reaction mixture was concentrated in vacuo to afford a crude residue. The reaction mixture was triturated the crude dye with 25 mL of dichloromethane. The dichloromethane layer was removed and the residue was purified by reverse-phase flash chromatography to furnish the desired product 6 as a green solid (319.9 mg, 76%). UV/Vis (methanol) $\lambda_{max=}$776 nm; LRMS (ES/acetonitrile), m/z calculated for C47H54F2N2O14S4 [M+H]$^+$ 1038.4, found 1038.4.

Example 76

62%). UV/Vis (methanol) $\lambda_{max}$=773 nm; LRMS (ES/acetonitrile), m/z calculated for C51H61F2N3O15S4 [M+H]$^+$ 1123.1, found 1123.3.

Example 77

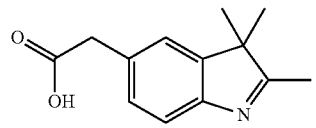

67

5-Carboxymethyl-2,3,3-trimethylindoline (67) is prepared either by the methods of Southwick et al., *Org. Prep. Proceed. Int.*, 20, 274-84, (1989) or alternatively by the method of U.S. Pat. No. 6,133,445.

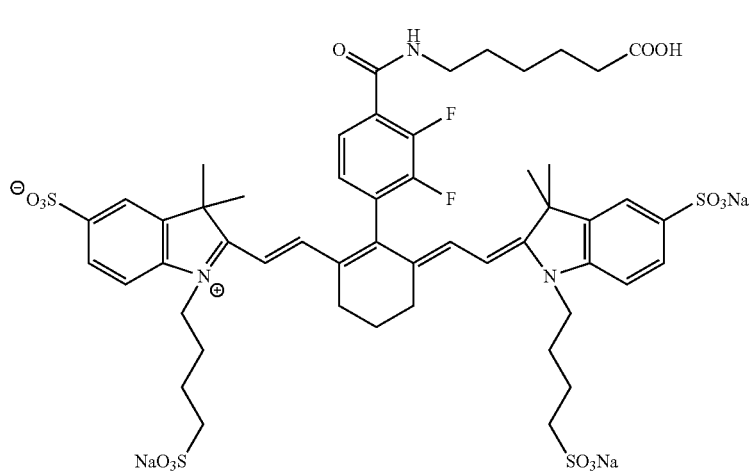

66

Compound 66 was prepared by adding compound 64 (430 mg, 0.40 mmol) to an oven-dried round-bottomed flask containing magnetic stir-bar and septum under nitrogen, followed by anhydrous DMSO (10 mL) and diisopropylethylamine (206 mg, 2.40 mmol). The flask was placed in a sonicator for 5 min followed by addition of N,N'-disuccinimidyl carbonate (612 mg, 2.40 mmol). The reaction mixture was stirred for 2 h at ambient temperature. After HPLC analysis showed complete consumption of the starting material, a solution of methyl 6-amino hexanoate (63.8 mg, 0.44 mmol) in anhydrous DMSO (1 mL) was added, and the reaction mixture was stirred for an additional 2 h. The reaction mixture was concentrated in vacuo to afford a crude residue. The residue was dissolved in water (5 mL) and a 1 N hydrochloric acid (250 µL) was added dropwise. The reaction mixture was stirred at ambient temperature for 2 h. The solution was concentrated under reduced pressure and the resulting green residue was purified by reverse-phase flash chromatography to furnish the desired product as a green solid (278.5 mg, Example 78

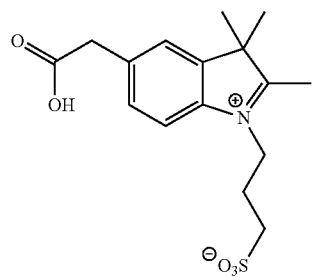

68

Compound 68 is prepared analogously to compound 1 except with 5-carboxymethyl-2,3,3-trimethylindoline (compound 67) as the starting material.

Example 79

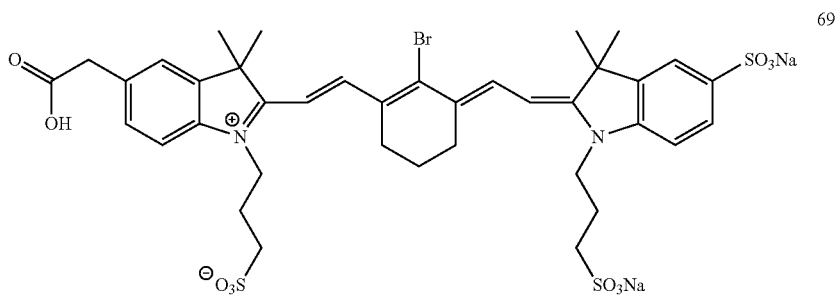

Compound 69 is prepared analogously to compound 7 except that compound 68, compound 5, and compound 1 are starting materials.

Example 80

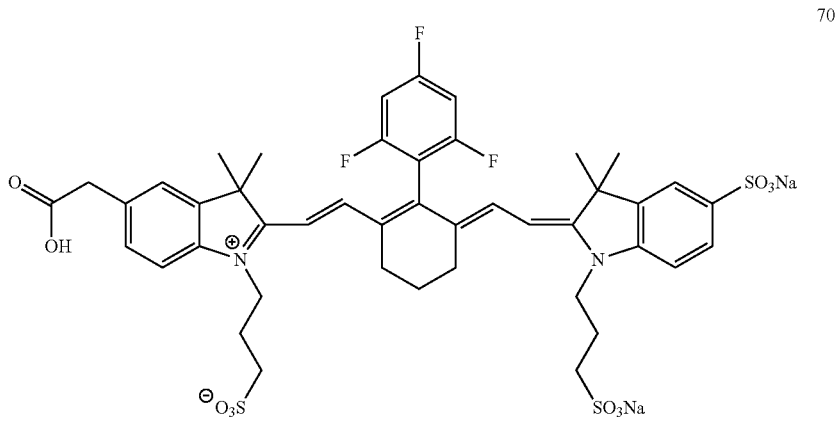

Compound 70 is prepared analogously to compound 11 except that compound 69 and 2,4,6-trifluorophenylboronic acid are used as starting materials.

Example 81

Comparison of Dye Emission Maxima and Quenching

Solutions of dye-linker standards and dye-linker-quencher samples were diluted into PBS buffer (pH 7.4) to give a dye-specific absorbance less than 0.2 AU. The fluorescence spectra of each dilution were then taken at a consistent excitation wavelength (670 nm for HETD and 770 nm for IRDye 800CW). The emission spectra were collected from 680-1000 nm for the HETD samples and 780-1000 nm for the IRDye 800CW samples.

| Quencher Version | Sample Name | Example Number | Emission Maximum | Percent Quenching |
|---|---|---|---|---|
| Compound 25a | HETD-PHOS-OX (ref) (47b) | Example 58 | 3020520 | |
| | HETD-Compound 25a -Click 1 (48) | Example 59 | 1054060 | 65.1 |
| | IRDye 800CW-PEG2-NH2 (ref) (32) | Example 39 | 1343900 | |
| | IRDye 800CW-PEG2-Compound 25a (38) | Example 48 | 385983 | 71.3 |
| | IRDye 800CW-C6-Compound 25a (37) | Example 47 | 519267 | 61.4 |
| | IRDye 800CW-PEG11-NH2 (ref) | N/A | 1272820 | |
| | IRDye 800CW-PEG11-Compound 25a (39) | Example 49 | 438981 | 65.5 |
| | IRDye 800CW-PEG-N3 (ref) (29) | Example 36 | 1245060 | |
| | IRDye 800CW-Compound 25a -Click 1 (43) | Example 53 | 550761 | 55.8 |
| | IRDye 800CW-DBCO (ref) (30) | Example 37 | 1203780 | |
| | IRDye 800CW-Compound 25a -Click 2 (44) | Example 54 | 424840 | 64.7 |
| Compound 49 | HETD-PHOS-OX (ref) (47b) | Example 58 | 3020520 | |
| | HETD-Compound 49-Click 1 (75) | Example 85 | 278958 | 90.8 |

| Quencher Version | Sample Name | Example Number | Emission Maximum | Percent Quenching |
|---|---|---|---|---|
| | HETD-Compound 49-Click 2 (76) | Example 86 | 499225 | 83.5 |
| | IRDye 800CW-PEG2-NH2 (ref) (32) | Example 39 | 1343900 | |
| | IRDye 800CW-PEG2-Compound 49 (52) | Example 62 | 58878 | 95.6 |
| | IRDye 800CW-PEG11-NH2 (ref) | N/A | 1272820 | |
| | IRDye 800CW-PEG11-Compound 49 (53) | Example 63 | 128324 | 89.9 |
| | IRDye 800CW-PEG-N3 (ref) (29) | Example 36 | 1245060 | |
| | IRDye 800CW-Compound 49-Click 1 (56) | Example 66 | 43472 | 96.5 |
| | IRDye 800CW-DBCO (ref) (30) | Example 37 | 1203780 | |
| | IRDye 800CW-Compound 49-Click 2 (57) | Example 67 | 67930 | 94.4 |

All publications, patents and patent applications and cited in this specification including Attorney Docket Number 020031-011910PC, filed on even date herewith are herein incorporated by reference as if each individual publication, patent or patent application were specifically and individually indicated to be incorporated by reference. Although the foregoing invention has been described in some detail by way of illustration and example for purposes of clarity of understanding, it will be readily apparent to those of ordinary skill in the art that, in light of the teachings of this application, that certain changes and modifications may be made thereto without departing from the spirit or scope of the appended claims.

Additional background regarding click chemistry is included in the references that are shown below:
1. Ghosh, A. K.; Duong, T. T.; McKee, S. P.; Thompson, W. J. "N,N'-disuccinimidyl carbonate: a useful reagent for alkoxycarbonylation of amines." *Tetrahedron Lett.* 1992, 33, 2781-2784.
2. Ghosh, A. K.; McKee, S. P.; Duong, T. T.; Thompson, W. J. "An efficient synthesis of functionalized urethanes from azides." *Chem. Commun.* 1992, 1308-13010.
3. Højfeldt, J. W.; Blakskjær, P.; Gothelf, K. V. "A Cleavable Amino-Thiol Linker for Reversible Linking of Amines to DNA." *J. Org. Chem.* 2006, 71, 9556-9559.
4. Bertozzi, C. R.; Bednarski, M. D. "The synthesis of heterobifunctional linkers for the conjugation of ligands to molecular probes." *J. Org. Chem.* 1991, 56, 4326-4329.
5. Schwabacher, A. W.; Lane, J. W.; Scheisher, M. W.; Leigh, K. M.; Johnson, C. W. "Desymmetrization Reactions: Efficient Preparation of Unsymmetrically Substituted Linker Molecules." *J. Org. Chem.* 1998, 63, 1727-1729.
6. Website: http://www.baseclick.eu and references therein.
7. Chan, T. R.; Higraf, R.; Sharpless, K. B.; Fokin, V. V. "Polytriazoles as Copper(I)—Stabilizing Ligands in Catalysis." *Org. Lett.* 2004, 6, 2853-2855.
8. El-Sagheer, A. H.; Brown, T. "Click Chemistry with DNA." *Chem. Soc. Rev.* 2010, 39, 1388-1405.
9. C. W. Tomoe, C. Christensen, M. Meldal, *J. Org. Chem.* 2002, 67, 3057-3064; V. V. Rostovtsev, L. G. Green, V. V. Fokin, K. B. Sharpless, *Angew. Chem.* 2002, 114, 2708-2711; Angew. Chem. Int. Ed. 2002, 41, 2596-2599.
10. C. J. Burrows, J. G. Muller, *Chem. Rev.* 1998, 98, 1109-1151.
11. T. R. Chan, R. Hilgraf, K. B. Sharpless, V. V. Fokin, *Org. Lett.* 2004, 6, 2853-2855.
12. J. Gierlich, G. A. Burley, P. M. E. Gramlich, D. M. Hammond, T. Carell, *Org. Lett.* 2006, 8, 3639-3642. F. Seela, V. R. Sirivolu, Chem. *Biodiversity* 2006, 3, 509-514.
13. P. M. E. Gramlich, S. Warncke, J. Gierlich, T. Carell, *Angew. Chem.* 2008, 120, 3491-3493; *Angew. Chem. Int. Ed.* 2008, 47, 3442-3444.

What is claimed is:
1. A near-infrared (NIR) compound of the formula:

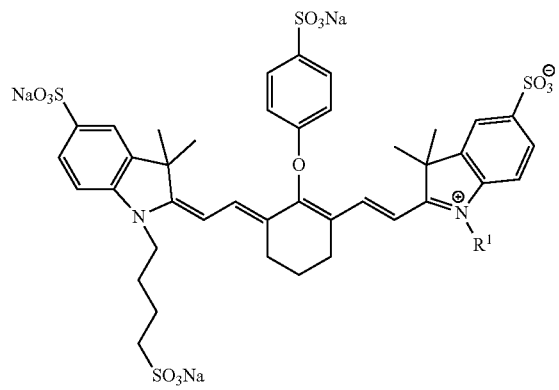

wherein $R^1$ is LYZ;
L is an optional member selected from the group consisting of a bond, a $C_1$-$C_{20}$ alkylene, and a $C_1$-$C_{20}$ alkenylene; wherein the alkylene or alkenylene is optionally interrupted by at least one heteroatom;
Y is an optional member selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;
$R^{15}$ is a member selected from the group consisting of alkyl and alkoxycarbonylalkyl, wherein the alkyl is optionally interrupted by at least one heteroatom;
Z is $R^{16}$;
or alternatively, —Y—Z is a member selected from the group consisting of —N(Z)$_2$, —N(Z)C(O)Z, and —C(O)N(Z)$_2$, and the two Z groups may optionally be linked to form a cycloalkynyl group; and
$R^{16}$ is member selected from the group consisting of azido, alkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester, DBCO, DBCO-1, TPPME, BARAC, DIFO, BCN, DIBO, TMDIBO and DIFO3, wherein the compound has emission in the near-infrared.

2. The compound of claim 1, wherein $R^{16}$ is member selected from the group consisting of azido, alkynyl, a pegylated azido, and a pegylated alkynyl.

3. The compound of claim 2, wherein $R^{16}$ is azido.

4. The compound of claim 2, wherein $R^{16}$ is alkynyl.

5. The compound of claim 1, wherein $R^{16}$ is member selected from the group consisting of DBCO, DBCO-1, TPPME, BARAC, DIFO, BCN, DIBO, TMDIBO and DIFO3.

6. The compound of claim 5, wherein $R^{16}$ is DBCO or DBCO-1.

7. The compound of claim 5, wherein $R^{16}$ is DBCO.

8. The compound of claim 1, wherein said compound has the formula:

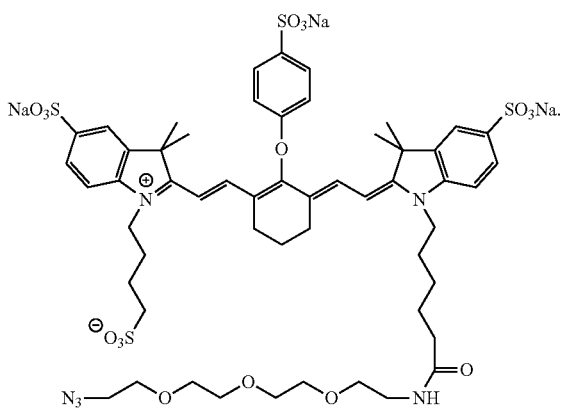

9. The compound of claim 1, wherein said compound has the formula:

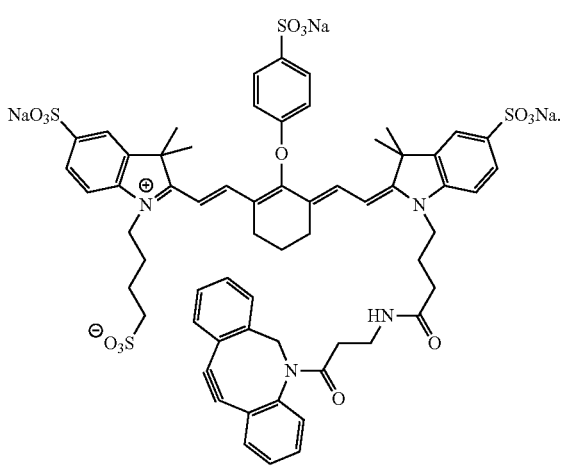

10. A method for imaging, said method comprising: administering a compound having the formula:

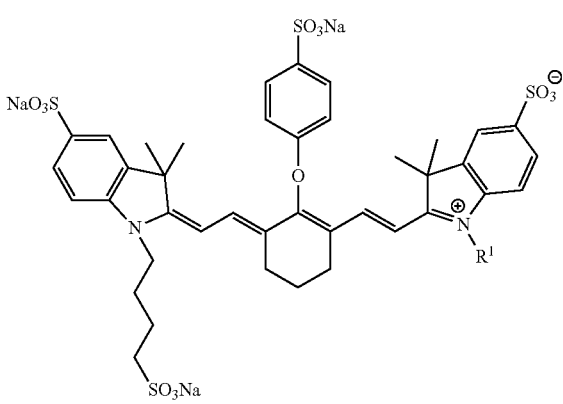

wherien $R^1$ is LYZ;

L is an optional member selected from the group consisting of a bond, a $C_1$-$C_{20}$ alkylene, and a $C_1$-$C_{20}$ alkenylene; wherein the alkylene or alkenylene is optionally interrupted by at least one heteroatom;

Y is an optional member independently selected from the group consisting of a bond, —O—, —S—, —NH—, —NHC(O)—, —C(O)NH—, —NR$^{15}$—, —NR$^{15}$C(O)—, —C(O)NR$^{15}$—, —N(Z)—, —N(Z)C(O)—, and —C(O)N(Z)—;

$R^{15}$ is a member selected from the group consisting of alkyl and alkoxycarbonylalkyl, wherein the alkyl is optionally interrupted by at least one heteroatom;

Z is -L-$R^{16}$;

or alternatively, —Y—Z is a member selected from the group consisting of —N(Z)$_2$, —N(Z)C(O)Z, and —C(O)N(Z)$_2$, and the two Z groups may optionally be linked to form a cycloalkynyl group;

$R^{16}$ is member selected from the group consisting of azido, alkynyl, a pegylated azido, a pegylated alkynyl, a pegylated cycloalkynyl, a pegylated spirocycloalkynyl, an o-diarylphosphino aryl ester, and an ortho substituted phosphine oxide aryl ester, DBCO, DBCO-1, TPPME, BARAC, DIFO, BCN, DIBO, TMDIBO and DIFO3, detecting said compound in a tissue or organism.

11. The method of imaging of claim 10, wherein said method further comprises detecting said compound in a living organism.

12. The method of imaging of claim 10, wherein the method comprises a step of imaging a tumor, tissue, or organ.

13. The method of imaging of claim 12, wherein the tumor, tissue, or organ is selected from the group consisting of vascular endothelial tissue, an abnormal vascular wall of a tumor, a solid tumor, a tumor of the head, a tumor of the neck, a tumor of the gastrointestinal tract, a tumor of the liver, a tumor of the breast, a tumor of the prostate, a tumor of the ovary, a tumor of the uterus, a tumor of the testicle, a tumor of the lung, a nonsolid tumor, a malignant hematopoietic cell, a malignant lymphoid cell, a lesion in the vascular system, a diseased bone marrow, neuronal tissue, diseased neuronal tissue, and diseased cells in which the disease is an autoimmune disease or an inflammatory disease.

14. The method of claim 10, wherein the compound is used as a detectable tracer element in a biological or non-biological fluid.

15. The method of claim 10, wherein the compound is used to enhance visualization of chorioretinal diseases, vascular disorders, retinopathies, neovascularization, or ocular tumors; and wherein the method comprises direct microscopic imaging.

16. The method of claim 10, wherein the compound is used to enhance visualization of skin diseases or skin tumors; and wherein the method comprises direct microscopic imaging.

17. The method of claim 10, wherein the compound is used to enhance visualization of a gastrointestinal disease, a gastrointestinal tumors, an oral disease, an oral tumor, a bronchial disease, a bronchial tumor, a cervical disease, cervical tumor, a urinary disease, or a urinary tumor; and wherein the method comprises endoscopy.

18. The method of claim 10, wherein $R^{16}$ is member selected from the group consisting of azido, alkynyl, a pegylated azido, and a pegylated alkynyl.

19. The method of claim 10, wherein $R^{16}$ is azido.

20. The method of claim 10, wherein $R^{16}$ is alkynyl.

21. The method of claim 10, wherein $R^{16}$ is member selected from the group consisting of DBCO, DBCO-1, TPPME, BARAC, DIFO, BCN, DIBO, TMDIBO and DIFO3.

22. The method of claim 10, wherein $R^{16}$ is member selected from the group consisting of DBCO, and DBCO-1.

23. The method of claim 10, wherein $R^{16}$ is DBCO.
24. The method of claim 10, wherein said compound has the formula:
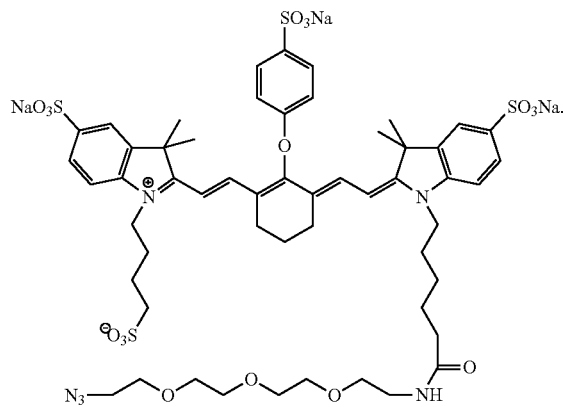
25. The method of claim 10, wherein said compound has the formula:
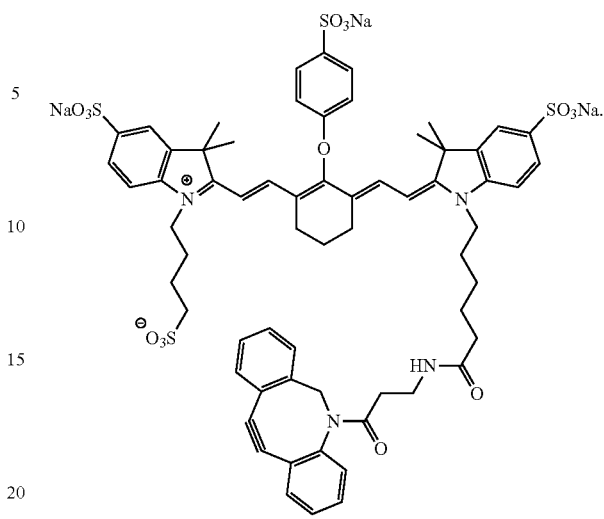
* * * * *